US010961189B2

(12) United States Patent
Khan

(10) Patent No.: US 10,961,189 B2
(45) Date of Patent: Mar. 30, 2021

(54) SPIRO-LACTAM NMDA RECEPTOR MODULATORS AND USES THEREOF

(71) Applicant: Aptinyx Inc., Evanston, IL (US)

(72) Inventor: M. Amin Khan, Evanston, IL (US)

(73) Assignee: Aptinyx Inc., Evanston, IL (US)

(*) Notice: Subject to any disclaimer, the term of this patent is extended or adjusted under 35 U.S.C. 154(b) by 0 days.

(21) Appl. No.: 16/321,901

(22) PCT Filed: Aug. 1, 2017

(86) PCT No.: PCT/US2017/044813
§ 371 (c)(1),
(2) Date: Jan. 30, 2019

(87) PCT Pub. No.: WO2018/026763
PCT Pub. Date: Feb. 8, 2018

(65) Prior Publication Data
US 2019/0161442 A1 May 30, 2019

Related U.S. Application Data

(60) Provisional application No. 62/523,413, filed on Jun. 22, 2017, provisional application No. 62/369,465, filed on Aug. 1, 2016.

(51) Int. Cl.
| *C07D 205/12* | (2006.01) |
| *C07D 205/08* | (2006.01) |
| *A61P 25/28* | (2006.01) |
| *A61P 25/22* | (2006.01) |
| *A61P 25/18* | (2006.01) |
| *A61P 25/24* | (2006.01) |
| *A61P 25/06* | (2006.01) |

(52) U.S. Cl.
CPC ............ *C07D 205/12* (2013.01); *A61P 25/06* (2018.01); *A61P 25/18* (2018.01); *A61P 25/22* (2018.01); *A61P 25/24* (2018.01); *A61P 25/28* (2018.01); *C07D 205/08* (2013.01)

(58) Field of Classification Search
CPC .................................................. C07D 205/12
See application file for complete search history.

(56) References Cited

U.S. PATENT DOCUMENTS

| 4,904,681 A | 2/1990 | Cordi et al. |
| 4,959,493 A | 9/1990 | Ohfume et al. |
| 5,061,721 A | 10/1991 | Cordi et al. |
| 5,086,072 A | 2/1992 | Trullas et al. |
| 5,166,136 A | 11/1992 | Ward et al. |
| 5,168,103 A | 12/1992 | Kinney et al. |
| 5,350,769 A | 9/1994 | Kasai et al. |
| 5,523,323 A | 6/1996 | Maccecchini |
| 5,605,911 A | 2/1997 | Olney et al. |
| 5,648,259 A | 7/1997 | Mallet et al. |
| 5,741,778 A | 4/1998 | Martin et al. |
| 5,763,393 A | 6/1998 | Moskal et al. |
| 5,804,550 A | 9/1998 | Bourguignon |
| 5,902,815 A | 5/1999 | Olney et al. |
| 5,952,389 A | 9/1999 | Fogel |
| 5,959,075 A | 9/1999 | Lok et al. |
| 6,007,841 A | 12/1999 | Caruso |
| 6,025,471 A | 2/2000 | Deghenghi |
| 6,107,271 A | 8/2000 | Moskal et al. |
| 6,147,230 A | 11/2000 | Shimamoto et al. |
| 6,197,820 B1 | 3/2001 | Sontheimer et al. |
| 6,521,414 B2 | 2/2003 | Melcher et al. |
| 6,541,453 B2 | 4/2003 | Oldham et al. |
| 6,635,270 B2 | 10/2003 | Hong et al. |
| 6,667,317 B2 | 12/2003 | Chenard et al. |
| 6,821,985 B2 | 11/2004 | Chenard et al. |
| 6,828,318 B2 | 12/2004 | Snape et al. |
| 7,273,889 B2 | 9/2007 | Mermelstein et al. |
| 7,884,080 B2 | 2/2011 | Aslanian et al. |
| 8,097,634 B2 | 1/2012 | Ackermann et al. |
| 8,492,340 B2 | 7/2013 | Moskal |
| 9,504,670 B2 | 11/2016 | Lowe, III et al. |
| 9,512,133 B2 | 12/2016 | Khan et al. |
| 9,512,134 B2 | 12/2016 | Lowe, III et al. |
| 9,579,304 B2 | 2/2017 | Lowe, III et al. |
| 9,708,335 B2 | 7/2017 | Lowe, III et al. |
| 9,738,650 B2 | 8/2017 | Lowe, III et al. |
| 9,758,525 B2 | 9/2017 | Lowe, III et al. |
| 9,802,946 B2 | 10/2017 | Khan et al. |
| 9,828,384 B2 | 11/2017 | Lowe, III et al. |

(Continued)

FOREIGN PATENT DOCUMENTS

| CN | 101066945 A | 11/2007 |
| CN | 101125817 A | 2/2008 |

(Continued)

OTHER PUBLICATIONS

Nagamori, et al. Document No. 163:374386, retrieved from STN; entered in STN on Aug. 27, 2015.*
McMaster, et al. Document No. 157:133191, retrieved from STN; entered in STN on Jun. 3, 2012.*
Liu, et al. Document No. 120:244445, retrieved from STN; entered in STN on May 14, 1994.*
Ikeda, et al. Document No. 101:54757, retrieved from STN; entered in STN on Aug. 18, 1984.*
Golub, et al. Science vol. 286 Oct. 15, 1999 pp. 531-536.*
FDA mulls drug to slow late-stage Alzheimer's [online] retrieved from the internet; Sep. 24, 2003; URL: http://www.cnn.com/2003/HEALTH/conditions/09/24/alzheinners.drug.ap/index.html.*
Lala, et al. Cancer and Metastasis Reviews 17, 1998, pp. 91-106.*
Abbott AV et al., 'The Formalin Test: Scoring Properties of the First and Second Phases of the Pain Response in Rats,' Pain, Jan. 1995 (Jan. 1995), 60(1):91-102.

(Continued)

*Primary Examiner* — Shawquia Jackson
(74) *Attorney, Agent, or Firm* — Goodwin Procter LLP

(57) ABSTRACT

Disclosed are compounds having potency in the modulation of NMDA receptor activity. Such compounds can be used in the treatment of conditions such as depression and related disorders. Orally delivered formulations and other pharmaceutically acceptable delivery forms of the compounds, including intravenous formulations, are also disclosed.

25 Claims, No Drawings

(56) References Cited

U.S. PATENT DOCUMENTS

| | | | |
|---|---|---|---|
| 9,925,169 | B2 | 3/2018 | Khan |
| 9,932,347 | B2 | 4/2018 | Khan |
| 10,052,308 | B2 | 8/2018 | Lowe, III et al. |
| 10,150,769 | B2 | 12/2018 | Khan |
| 10,195,179 | B2 | 2/2019 | Khan |
| 10,196,401 | B2 | 2/2019 | Khan |
| 2002/0103335 | A1 | 8/2002 | Oldham et al. |
| 2003/0022253 | A1 | 1/2003 | Moskal |
| 2003/0064921 | A1 | 4/2003 | Millhauser et al. |
| 2003/0175734 | A1 | 9/2003 | Kroes et al. |
| 2005/0037433 | A1 | 2/2005 | Nakanishi et al. |
| 2005/0118286 | A1 | 6/2005 | Suffin et al. |
| 2006/0063707 | A1 | 3/2006 | Baudry et al. |
| 2006/0241046 | A1 | 10/2006 | Olivera et al. |
| 2007/0087404 | A1 | 4/2007 | Stahl et al. |
| 2007/0208001 | A1 | 9/2007 | Zhuo et al. |
| 2009/0221544 | A1 | 9/2009 | Stein et al. |
| 2010/0102616 | A1 | 4/2010 | Yamasaki et al. |
| 2011/0306586 | A1 | 12/2011 | Khan et al. |
| 2012/0295852 | A1 | 11/2012 | Moskal |
| 2013/0005662 | A1 | 1/2013 | Moskal |
| 2013/0035292 | A1 | 2/2013 | Moskal et al. |
| 2013/0053325 | A1 | 2/2013 | Moskal et al. |
| 2013/0310323 | A1 | 11/2013 | Moskal |
| 2013/0316954 | A1 | 11/2013 | Moskal |
| 2014/0107037 | A1 | 4/2014 | Moskal |
| 2015/0051262 | A1 | 2/2015 | Khan et al. |
| 2015/0105364 | A1 | 4/2015 | Khan et al. |
| 2015/0336969 | A1 | 11/2015 | Khan et al. |
| 2015/0368252 | A1 | 12/2015 | Lowe, III et al. |
| 2015/0368253 | A1 | 12/2015 | Lowe, III et al. |
| 2015/0368254 | A1 | 12/2015 | Lowe, III et al. |
| 2015/0376195 | A1 | 12/2015 | Lowe, III et al. |
| 2016/0122359 | A1 | 5/2016 | Lowe, III et al. |
| 2016/0289240 | A1 | 10/2016 | Lowe, III et al. |
| 2016/0368926 | A1 | 12/2016 | Lowe, III et al. |
| 2017/0231956 | A1 | 8/2017 | Lowe, III et al. |
| 2017/0333395 | A1 | 11/2017 | Khan |
| 2017/0334922 | A1 | 11/2017 | Khan |
| 2018/0092879 | A1 | 4/2018 | Khan |
| 2018/0093994 | A1 | 4/2018 | Khan |
| 2018/0127430 | A1 | 5/2018 | Lowe, III et al. |
| 2018/0155354 | A1 | 6/2018 | Lowe, III et al. |
| 2018/0179217 | A1 | 6/2018 | Lowe, III et al. |
| 2018/0179218 | A1 | 6/2018 | Lowe, III et al. |
| 2018/0215767 | A1 | 8/2018 | Lowe, III et al. |
| 2018/0244680 | A1 | 8/2018 | Lowe, III et al. |
| 2018/0250267 | A1 | 9/2018 | Lowe, III et al. |
| 2018/0291023 | A1 | 10/2018 | Khan |
| 2019/0077807 | A1 | 3/2019 | Khan et al. |
| 2019/0161442 | A1 | 5/2019 | Khan |
| 2019/0175588 | A1 | 6/2019 | Khan |
| 2019/0177334 | A1 | 6/2019 | Khan |
| 2019/0194200 | A1 | 6/2019 | Khan |

FOREIGN PATENT DOCUMENTS

| | | |
|---|---|---|
| CN | 103974712 A | 8/2014 |
| CN | 104321071 A | 1/2015 |
| EP | 0180398 A1 | 5/1986 |
| EP | 2542254 A1 | 1/2013 |
| EP | 2771021 | 5/2013 |
| JP | 2013519683 A | 5/2013 |
| JP | 2014520072 A | 8/2014 |
| RU | 2039035 C1 | 7/1995 |
| WO | WO-1996/032105 A1 | 10/1996 |
| WO | WO-1997/043306 A1 | 11/1997 |
| WO | WO-1999/024584 A1 | 5/1999 |
| WO | WO-1999/051985 A1 | 10/1999 |
| WO | WO-2000/028090 A2 | 5/2000 |
| WO | WO-2001/36685 A2 | 5/2001 |
| WO | WO-2001/96606 A2 | 12/2001 |
| WO | WO-2001/98367 A2 | 12/2001 |
| WO | WO-2002/47535 A2 | 6/2002 |
| WO | WO-2002/072609 A2 | 9/2002 |
| WO | WO-2003/010540 A1 | 2/2003 |
| WO | WO-2004/005293 A2 | 1/2004 |
| WO | WO-2005/020973 A2 | 3/2005 |
| WO | WO-2005/035535 A1 | 4/2005 |
| WO | WO-2007/088041 A1 | 8/2007 |
| WO | WO-2007/103719 A2 | 9/2007 |
| WO | WO-2009/039390 A2 | 3/2009 |
| WO | WO-2009/105718 A1 | 8/2009 |
| WO | WO-2009/156396 A1 | 12/2009 |
| WO | WO-2010/015545 A1 | 2/2010 |
| WO | WO-2010/018213 A2 | 2/2010 |
| WO | WO-2010/033757 A1 | 3/2010 |
| WO | WO-2010/065709 A2 | 6/2010 |
| WO | WO-2010/102616 A1 | 9/2010 |
| WO | WO-2011/003064 A2 | 1/2011 |
| WO | WO-2011/044089 A2 | 4/2011 |
| WO | WO-2011/100585 A1 | 8/2011 |
| WO | WO-2012/021712 A1 | 2/2012 |
| WO | WO-2012/149389 A2 | 11/2012 |
| WO | WO-2013/001448 A1 | 1/2013 |
| WO | WO-2013/014448 A1 | 1/2013 |
| WO | WO-2013/063120 A2 | 5/2013 |
| WO | WO-2014/011590 A2 | 1/2014 |
| WO | WO-2014/120783 A1 | 8/2014 |
| WO | WO-2014/120784 A1 | 8/2014 |
| WO | WO-2014/120789 A1 | 8/2014 |
| WO | WO-2014/120800 A1 | 8/2014 |
| WO | WO-2014120786 A1 | 8/2014 |
| WO | WO-2017/201283 A1 | 11/2017 |
| WO | WO-2017/201285 A1 | 11/2017 |
| WO | WO-2018/026763 A1 | 2/2018 |
| WO | WO-2018/026779 A1 | 2/2018 |
| WO | WO-2018/026782 A1 | 2/2018 |
| WO | WO-2018/026792 A1 | 2/2018 |
| WO | WO-2018/026798 A1 | 2/2018 |

OTHER PUBLICATIONS

Abramets, II, 'Neurophysiological and Neurochemical Aspects of the Effects of Antidepressants and Mood Stabilizers,' Neurophysiol, Jan. 2008 (Jan. 2008), 40(1):64-78.

Alonso E et al., 'Spiro-Beta-Lactams as Beta-Turn Mimetics. Design, Synthesis, and NMR Conformational Analysis,' J Org Chem, Sep. 21, 2001 (Sep. 21, 2001), 66(19):6333-8.

Anonymous, Database Accession No. 1031928-30-9, Database Registry [Online] Chemical Abstracts Service, Columbus, Ohio, US; Jul. 1, 2008 (Jul. 1, 2008), XP002668992.

Anonymous, Database Accession No. 1053605-89-2, Database Registry [Online] Chemical Abstracts Service, Columbus, Ohio, US; Sep. 28, 2008 (Sep. 28, 2008), XP002668993.

Anonymous, NCBI Submission NM_000149, 'Homo sapiens Fucosyltransferase 3 (galactoside 3(4)-L-fucosyltransferase, Lewis Blood Group)(FUT3), Transcript Variant 1, mRNA,' 1990 (1990), Retrieved from the internet; <<URL:http://www.ncbi.nlm.nih.gov/nuccore/148277008>>, pp. 1-5.

Anonymous, NCBI Submission NM_001276, Homo sapiens Chitinase 3-like 1 (cartilage glycoprotein-39)(CHI3L1), mRNA,' 1989 (1989), Retrieved from the internet; <URL:http://www.ncbi.nlm.nih.gov/nuccore/144226250>, pp. 1-5.

Anonymous, NCBI Submission NM_030979.1, 'Homo sapiens poly(A) Binding Protein, Cytoplasmic 3 (PABPC3), mRNA,' 2003 (2003), Retrieved from the internet; <URL:http://www.ncbi.nlm.nih.gov/nuccore/13569957>, pp. 1.

Anonymous, NCBI Submission NM_173216, 'Homo sapiens ST6 beta-galactosamide alpha-2,6-sialyltransferase 1 (ST6GAL1), transcript variant 1, mRNA,' 1989 (1989), Retrieved from the internet; <URL:http://www.ncbi.nlm.nih.gov/nuccore/27765090>, pp. 1-5.

Bennett GJ and Xie Y-K, 'A Peripheral Mononeuropathy in Rat That Produces Disorders of Pain Sensation Like Those Seen in Man,' Pain, Apr. 1988 (Apr. 1988), 33(1):87-107.

Bittermann H and Gmeiner P, 'Chirospecific Synthesis of Spirocyclic beta-Lactams and Their Characterization as Potent Type II beta-Turn Inducing Peptide Mimetics,' J Org Chem, Jan. 6, 2006 (Jan. 6, 2006), 71(1):97-102.

(56) References Cited

OTHER PUBLICATIONS

Bittermann H et al., 'A Highly Practical RCM Approach Towards a Molecular Building Kit of Spirocyclic Reverse Turn Mimics,' Chem Eur J, Aug. 16, 2006 (Aug. 16, 2006), 12(24):6315-22.
Burch RM et al., 'GLYX-13, An NMDA Receptor Glycine Site Functional Partial Agonist, Does Not Elicit Psychotomimetic Side Effects in Normal Human Volunteers at Doses Expected to be Therapeutic in Treatment-Resistant Major Depressive Disorder,' NCDEU, Jun. 16, 2010 (Jun. 16, 2010), Naurex, Inc., Evanston, IL (Publ), pp. 1 (Poster #unknown).
Burgdorf JS et al., 'Neurobiology of 50-kHz Ultrasonic Vocalizations in Rats: Electrode, Lesion, and Pharmacology Studies,' Behav Brain Res, Mar. 19, 2007 (Mar. 19, 2007) (ePub), 182(2):274-83.
Burgdorf JS et al., The Antidepressant and Anxiolytic Properties of GLYX-13: A Novel NMDA Receptor Glycine Site Functional Partial Agonist, ACNP 2010 Meeting Dec. 6, 2010 (Dec. 6 2010),. pp. 1 (Poster #198).
Burgdorf JS et al., 'The Effects of Selective Breeding for Differential Rates of 50-kHz Ultrasonic Vocalizations on Emotional Behavior in Rats,' Dev Psychobiol, Jan. 2009 (Jan. 2009), 51(1):34-46.
Burgdorf JS et al., 'The N-Methyl-D-Aspartate Receptor Modulator GLYX-13 Enhances Learning and Memory, in Young Adult and Learning Impaired Aging Rats,' Neurobiol Aging, May 14, 2009 (May 14, 2009) (ePub), 32(4):698-706.
Burgdorf JS et al., "Uncovering the Molecular Basis of Positive Affect Using Rough-and-Tumble Play in Rats: A Role for the NMDA Receptor and Implications for Depression," Neuroscience, Jul. 14, 2010, (Jul. 14, 2010) (ePub), 168(3):769-77.
Burgdorf JS et al., "Uncovering the Molecular Basis of Positive Affect Using Rough-and-Tumble Play in Rats: A Role for the NMDA Receptor and Implications for Depression," Neuroscience 38th Annual Meeting, Washington DC, Nov. 17, 2008 (Nov. 17, 2008), pp. 1-2 (Poster #393.1/UU11) [Electronically available Sep. 2008].
Careri M et al., 'Pentcopper(II) 12-Metallacrown-4 Complexes with alpha- and beta-Aminohydroxamic Acids in Aqueous Solution: A Reinvestigation,' J Inorg Chem, Jan. 15, 2003 (Jan. 15, 2003), 93(3-4):174-80.
Coates C et al., 'Product Class 9: Beta-Lactams,' *Science of Synthesis*, Georg Thieme Verlag KG, Stuttgart, DE (Pub), 2000 (2000), 21:609-46.
Cremonesi G et al., 'Enantiomerically Pure Polyheterocyclic Spiro-beta-Lactams from trans-4-Hydroxy-L-proline,' J Org Chem, Mar. 19, 2010 (Mar. 19, 2010), 75(6):2010-7.
Dalla Croce P and La Rosa C, 'Stereoselective Synthesis of N-Phenylsulfonyl Substituted Spiro-beta-Lactams,' Tetrahedron: Asymmetry, Mar. 26, 1999 (Mar. 26, 1999), 10(6):1193-9.
Dalla Croce P et al., 'Reaction of Mesoionic Compounds Deriving from Cyclic N-Acyl-alpha-amino Acids with N-(Phenylmethylene)benzenesulfonamide,' Tetrahedron, Jan. 1, 1999 (Jan. 1, 1999), 55(1):201-10.
Del Pozo C et al., 'Diastereo- and Enantioselective Synthesis of Novel beta-Lactam-Containing 1,4-Benzodiazepines Through a Ketene-Imine Cycloaddition Reaction,' Eur J Org Chem, Jan. 19, 2004 (Jan. 19, 2004), 2004(3):535-45.
Duman RS, 'Pathophysiology of Depression: The Concept of Synaptic Plasticity,' Eur Psychiatry, Jul. 2002 (Jul. 2002), 17(Suppl 3):306-10.
Erick M Carreira and Lisbet Kvaerno, Classics in Stereoselective Synthesis, (1st ed. 2009), Wiley-VCH Verlag GmbH & Co. KGaA, Weinham, DE (Publ), pp. 19-102 ISBN: 978-3-527-32452-1.
European Patent Office, Supplementary European Search Report (Form 1503) for EP 09 81 5233 (Fink D), completed at Munich DE on Feb. 8, 2012 (Feb. 8, 2012) pp. 1-3.
European Patent Office, Supplementary European Search Report (Form 1503) for EP 10 82 2514 (Fink D), completed at Munich DE on Feb. 1, 2013 (Feb. 1, 2013) pp. 1-2.
Export Data for 3 hydroxy 2 5 sulfonyl oxo2 5 diazaspiro, Apr. 22, 2016, Feb. 3, 2016, Jan. 30, 2016 and Mar. 26, 2015.

Forni A, 'Two Diastereoisomers of 2-(Benzenesulfonyl)-5-benzoyl-1-oxo-3-phenyl-2,5-diazaspiro[3.4]octan-7-yl acetate,' Acta Crystallographica Sec C: Crystal Structure Commun, Sep. 1998 (Sep. 1998), C54(9):1320-2.
Foster AC and Fagg GE, 'Neurobiology: Taking Apart NMDA Receptors,' Nature, Oct. 1, 1987 (Oct. 1, 1987), 329(6138):395-6.
Golik U, 'Synthesis of Malonimide Derivatives as Potential Penicillin Analogs,' J Heterocycl Chem, Feb. 1972 (Feb. 1972), 9(1):21-4.
Grigg R et al., 'X=Y-ZH Systems as Potential 1,3-Dipoles. Part 46. Cascade 1,3-Dipolar Cycloaddition Reactions of Cephalosporin Imines,' Tetrahedron, Nov. 1995 (Nov. 1995), 51(48):13347-56.
Haring R et al., 'Binding Studies and Photoaffinity Labeling Identify Two Classes of Phencyclidine Receptors in Rat Brain,' Biochemistry, Sep. 8, 1987 (Sep. 8, 1987), 26(18):5854-61.
Haring R et al., 'Glycine-Like Modulation of N-Methyl-D-Aspartate Receptors by a Monoclonal Antibody that Enhances Long-Term Potentiation,' J Neurochem, Jul. 1991 (Jul. 1991), 57(1):323-32.
Haring R et al., 'Identification of Polypeptides of the Phencyclidine Receptor of Rat Hippocampus by Photoaffinity Labeling with [H3]Azidophencyclidine,' Biochemistry, Feb. 11, 1986 (Feb. 11, 1986), 25(3):612-20.
Haring R et al., 'Multiple Mode of Binding of Phencyclidines: High Affinity Association Between Phencyclidine Receptors in Rat Brain and a Monovalent Ion-Sensitive Polypeptide,' Biochem Biophys Res Commun, Jan. 30, 1987 (Jan. 30, 1987), 142(2):501-10.
Holderbach R et al., 'Enhanced Long-Term Synaptic Depression in an Animal Model of Depression,' Biol Psychiatry, Dec. 4, 2006 (Dec. 4, 2006) (ePub), 62(1):92-100.
International Search Report and Written Opinion for International Application No. PCT/US2017/033323, dated Jul. 17, 2017, 12 pages.
International Search Report and Written Opinion for International Application No. PCT/US2017/033326, dated Jul. 10, 2017, 12 pages.
International Search Report and Written Opinion for International Application No. PCT/US2017/044813, dated Oct. 19, 2017, 13 pages.
International Search Report and Written Opinion for International Application No. PCT/US2017/044838, dated Oct. 19, 2017, 11 pages.
International Search Report and Written Opinion for International Application No. PCT/US2017/044841, dated Oct. 23, 2017, 11 pages.
International Search Report and Written Opinion for International Application No. PCT/US2017/044861, dated Oct. 19, 2017, 11 pages.
International Search Report and Written Opinion for International Application No. PCT/US2017/044871, dated Oct. 19, 2017, 13 pages.
International Searching Authority, International Search Report (ISA/210) for Application No. PCT/US08/77045, (Young LW), completed on Mar. 28, 2009 (Mar. 28, 2009) and dated Apr. 29, 2009 (dated Apr. 29, 2009), pp. 1-3.
International Searching Authority, International Search Report (ISA/210) for Application No. PCT/US09/57401, (Young LW), completed Dec. 6, 2009 (Dec. 6, 2009) and dated Dec. 24, 2009 (dated Dec. 24, 2009), pp. 1-2.
International Searching Authority, International Search Report (ISA/210) for Application No. PCT/US09/66536, (Kang YJ), completed Aug. 9, 2010 (Aug. 9, 2010) and dated Aug. 9, 2010 (dated Aug. 9, 2010), pp. 1-5.
International Searching Authority, International Search Report (ISA/210) for Application No. PCT/US2014/013619, (Wolf C), completed Mar. 6, 2014 (Mar. 6, 2014) and dated Mar. 20, 2014 (dated Mar. 20, 2014), pp. 1-3.
International Searching Authority, International Search Report (ISA/210) for Application No. PCT/US2014/013621, (Wolf C), completed Feb. 27, 2014 (Feb. 27, 2014) and dated Mar. 13, 2014 (dated Mar. 13, 2014), pp. 1-2.

(56) References Cited

OTHER PUBLICATIONS

International Searching Authority, International Search Report (ISA/210) for Application No. PCT/US2014/013623, (Wolf C), completed Mar. 3, 2014 (Mar. 3, 2014) and dated Mar. 13, 2014 (dated Mar. 13, 2014), pp. 1-3.
International Searching Authority, International Search Report (ISA/210) for Application No. PCT/US2014/013626, (Rudolf M), completed Mar. 10, 2014 (Mar. 10, 2014) and dated Mar. 18, 2014 (dated Mar. 18, 2014), pp. 1-4.
International Searching Authority, International Search Report (ISA/210) for Application No. PCT/US2014/013639, (Wolf C), completed Feb. 28, 2014 (Feb. 28, 2014) and dated Mar. 13, 2014 (dated Mar. 13, 2014), pp. 1-3.
International Searching Authority, Written Opinion of Application No. PCT/US2008/077045 (ISA/237), (Young LW), completed Mar. 28, 2009 (Mar. 28, 2009) and dated Mar. 24, 2010 (dated Mar. 24, 2010), pp. 1-8.
International Searching Authority, Written Opinion of Application No. PCT/US2009/057401 (ISA/237), (Young LW), completed Dec. 6, 2009 (Dec. 6, 2009) and dated Mar. 22, 2011 (dated Mar. 22, 2011), pp. 1-6.
International Searching Authority, Written Opinion of Application No. PCT/US2009/066536 (ISA/237), (Kang YJ), completed Aug. 9, 2010 (Aug. 9, 2010) and dated Jun. 7, 2011 (dated Jun. 7, 2011), pp. 1-8.
International Searching Authority, Written Opinion of Application No. PCT/US2014/013619 (ISA/237), (Wolf C), completed Mar. 6, 2014 (Mar. 6, 2014) and dated Aug. 4, 2015 (dated Aug. 4, 2015), pp. 1-4.
International Searching Authority, Written Opinion of Application No. PCT/US2014/013621 (ISA/237), (Wolf C), completed Feb. 27, 2014 (Feb. 27, 2014) and dated Aug. 4, 2015 (dated Aug. 4, 2015), pp. 1-6.
International Searching Authority, Written Opinion of Application No. PCT/US2014/013623 (ISA/237), (Wolf C), completed Mar. 3, 2014 (Mar. 6, 2014) and dated Aug. 4, 2015 (dated Aug. 4, 2015), pp. 1-4.
International Searching Authority, Written Opinion of Application No. PCT/US2014/013626 (ISA/237), (Rudolf M, completed Mar. 10, 2014 (Mar. 10, 2014) and dated Aug. 4, 2015 (dated Aug. 4, 2015), pp. 1-6.
International Searching Authority, Written Opinion of Application No. PCT/US2014/013639 (ISA/237), (Wolf C), completed Feb. 28, 2014 (Feb. 28, 2014) and dated Aug. 4, 2015 (dated Aug. 4, 2015), pp. 1-4.
Johnson JA et al., 'The Preparation of a Double Metallahelicate Containing 28 Copper Atoms,' Angew Chem Int Ed Engl, Feb. 3, 2003 (Feb. 3, 2003), 42(5):546-9.
Johnson KM and Jones SM, 'Neuropharmacolgy of Phencyclidine: Basic Mechanisms and Therapeutic Potential,' Annu Rev Pharmacol Toxicol, 1990 (1990), 30:707-50.
Khasanov AB et al., 'Novel Asymmetric Approach to Proline-Derived Spiro-beta-Lactams,' J Org Chem., Aug. 20, 2004 (Aug. 20, 2004), 69(17):5766-9.
Kloog Y et al., 'Kinetic Characterization of the Phencyclidine-N-Methyl-d-asparate Receptor Interaction: Evidence for a Steric Blockade of the Channel,' Biochemistry, Feb. 9, 1988 (Feb. 9, 1988), 27(3):843-8.
Kloog Y et al., 'Mode of Binding of [3H]dibenzocycloalkenimine (MK-801) to the N-methyl-D-Aspartate (NMDA) Receptor and its Therapeutic Implication,' FEBS Letts, Mar. 28, 1988 (Mar. 28, 1988), 230(1-2):167-70.
Koller M and Urwyler S, 'Novel N-Methyl-D-aspartate Receptor Antagonists: A Review of Compounds Patented Since 2006,' Expert Opin Ther Pat, Nov. 8, 2010 (Nov. 8, 2010) (epub), 20(12):1683-702.
Kroes RA et al., 'Development of a Novel Glycobiologic Therapy for Glioblastoma,' Neuro-oncol, Oct. 2006 (Oct. 2006), 8(4):397-8, (Abstract #CB-14).

Kroes RA et al., 'Development of a Novel Glycobiology-Based Therapeutic for Glioblastoma,' J Neurochem, Nov. 10, 2006 (Nov. 10, 2006), 99(Suppl. 1):17 (Abstract #50).
Krystall JH et al., 'NMDA Agonists and Antagonists as Probes of Glutamatergic Dysfunction and Pharmacotherapies in Neuropsychiatric Disorders,' Harvard Rev Psychiatry, Sep.-Oct. 1999 (Sep-Oct. 1999), 7(3):125-43.
Leander JD et al., 'Lack of Ketamine-Like Discriminative Effects of GLYX-13: A Novel NMDA Receptor Glycine Site Functional Partial Agonist with Antidepressant-Like Preclinical Effects,' ACNP 49th Annual Meeting, Dec. 2010 (Dec. 2010), Miami Beach, FL, Naurex, Inc., Evanston, IL (Pub) (Poster #218).
Li G-Q et al., 'N-Heterocyclic Carbene Catalyzed Ring Expansion of 4-Formyl-beta-lactams: Synthesis of Succinimide Derivatives,' Org Lett, Aug. 9, 2007 (Aug. 9, 2007) (ePub), 9(18):3519-21.
Lynch G et al., 'Synaptic Pasticity in Early Aging,' Ageing Res Rev, Aug. 28, 2006 (Aug. 28, 2006) (ePub), 5(3):255-80.
Macias A et al., 'Diastereoselective [2+2]-Cycloaddition Reactions of Unsymmetrical Cyclic Ketenes with Imines: Synthesis of Modified Prolines and Theoretical Study of the Reaction Mechanism,' J Org Chem, Oct. 1, 2004 (Oct. 1, 2004) Sep. 10, 2005 (Sep. 10, 2005)(ePub), 69(21):7004-12.
Macias A et al., 'Unusual Rearrangement of Spiro-beta-Lactams to 1,4-diazabicyclo[4,4,0]decanes and 1,4-diazabicyclo[4,3,0]nonanes. Synthesis of Conformationally Restricted Sigma-Receptor Ligands,' Tetrahedron Lett, Jun. 2004 (Jun. 2004), 45(24):4657-60.
Marcias A et al., 'Synthesis of Enantiopure Pyrrolidine-Derived Peptidomimetics and Oligo-beta-Peptides via Nucleophilic Ring-Opening of beta-Lactams,' J Org Chem, Sep. 29, 2006 (Sep. 29, 2006), 71(20):7721-30.
Mayer ML and Miller RJ, 'Excitatory Amino Acid Receptors, Second Messengers and Regulation of Intracellular Ca2+ in Mammalian Neurons,' Trends Pharmacol Sci, Jun. 1990 (Jun. 1990), 11(6):254-60.
McLeod MN et al., 'Chromium Potentiation of Antidepressant Pharmacotherapy for Dysthymic Disorder in 5 Patients,' J Clin Psychiatry, Apr. 1999 (Apr. 1999), 60(4):237-40.
Mishra H et al., 'Three-Dimensional Quantitative Structure-Activity Relationship and Comparative Molecular Field Analysis of Dipeptide Hydroxamic Acid Helicobacter pylori Urease Inhibitors,' Antimicrob Agents Chemother, Aug. 2002 (Aug. 2002), 46(8):2613-8.
Monahan JB et al., 'D-Cycloserine, a Positive Modulator of the N-Methyl-d-Asparate Receptor, Enhances Performance of Learning in Rats,' Pharmacol Biochem Behav, Nov. 1989 (Nov. 1989), 34(3):649-53.
Moskal JR and Burgdorf JS, 'The Antidepressant and Anxiolytic Properties of GLYX-13: A Novel NMDA Receptor Glycine Site Functional Partial Agonist,' ACNP 29th Annual Meeting, Dec. 7, 2009 (Dec. 7, 2009), Hollywood, FL, Naurex, Inc. Evanston, IL (Pub) (Poster #059).
Moskal JR and Schaffner AE, 'Monoclonal Antibodies to the Dentate Gyrus: Immunocytochemical Characterization and Flow Cytometric Analysis of Hippocampal Neurons Bearing a Unique Cell-Surface Antigen,' J Neurosci, Jul. 1986 (Jul. 1986), 6(7):2045-53.
Moskal JR et al., 'A Novel Approach to Unlocking the Therapeutic Potential of the NMDA Receptor,' Vital Signs e-Magazine, Sep. 2010 (Sep. 2010), pp. 1-2.
Moskal JR et al., 'GLYX-13: A Monoclonal Antibody-Derived Peptide that Acts as an N-Methyl-D-Aspartate Receptor Modulator,' Neuropharmacol, Jul. 26, 2005 (Jul. 26, 2005) (ePub), 49(7):1077-87.
Moskal JR et al., 'The Use of Antibody Engineering to Create Novel Drugs that Target N-Methyl-D-Aspartate Receptors,' Curr Drug Targets, Sep. 2001 (Sep. 2001), 2(3):331-45.
Moskal JR, 'The Anti-depressant and Anxiolytic Properties of GLYX-13: A Glycine-site Functional Partial Agonist (GFPA), a Novel Mechanism for Modulating NMDA,' ACNP 48th Annual Meeting, Dec. 7, 2009 (Dec. 7, 2009), Hollywood, FL, pp. 1-2 (Abstract).

(56) References Cited

OTHER PUBLICATIONS

Myers SM and Johnson CP, 'Management of Children with Autism Spectrum Disorders,' Pediatrics, Oct. 29, 2007 (Oct. 29, 2007) (ePub), 120(5):1162-82.
Narahashi T et al., 'Mechanisms of Action of Cognitive Enhancers on Neuroreceptors,' Biol Pharm Bull, Nov. 2004 (Nov. 2004), 27(11):1701-6.
Overman LE and Osawa T, 'A Convenient Synthesis of 4-Unsubstituted beta-Lactams,' J Am Chem Soc, Mar. 1985 (Mar. 1985), 107(6):1698-701.
Parac-Vogt TN et al., 'Pentacopper(II) Complexes of alpha-Aminohydroxamic Acids: Uranyl-Induced Conversion of a 12-Metallacrown-4 to a 15-Metallacrown-5,' J Inorg Biochem, Nov. 21, 2004 (Nov. 21, 2004) (ePub), 99(2):497-504.
Patani et al., "Bioisosterism: A Rational Approach in Drug Design," Chem. Rev., Jan. 1, 1997, 96(8):3147-3176.
Pittenger C et al., 'The NMDA Receptor as a Therapeutic Target in Major Depressive Disorder,' CNS Neurol Disord Targets, Apr. 2007 (Apr. 2007), 6(2):101-15.
Raghavan B et al., 'Allosteric Modulation of the Dopamine D2 Receptor by Pro-Leu-Gly-NH2 Peptidomimetics Constrained in Either a Polyproline II Helix or a Type II beta-Turn Conformation,' J Med Chem, Apr. 9, 2009 (Apr. 9, 2009), 52(7):2043-51.
Ransom RW and Stec NL, 'Cooperative Modulation of [3H]MK-801 Binding to the N-Methyl- d-Asparate Receptor-Ion Channel Complex by I-Glumate, Glycine, and Polyamines,' J Neurochem, Sep. 1988 (Sep. 1988), 51(3):830-6.
Rasmusson GH et al., '6-Substituted Penicillin Derivatives,' Tetrahedron Lett, 1973 (1973), 14(2):145-8.
Rautio J et al., 'Prodrugs: Design and Clinical Applications,' Nat Rev Drug Discov, Mar. 2008 (Mar. 2008), 7(3):255-70.
Schell MJ, 'The N-methyl D-aspartate Receptor Glycine Site and D-serine Metabolism: An Evolutionary Perspective,' Philos Trans R Soc Lond B Biol Sci, Jun. 29, 2004 (Jun. 29, 2004), 359(1446):943-64.
Shankar GM and Walsh DM, 'Alzheimer's Disease: Synaptic Dysfunction and A-beta,' Mol Neurodegener, Nov. 23, 2009 (Nov. 23, 2009), 4:48-61.
Siemion IZ et al., 'Conformational Preferences of the Sequential Fragments of the Hinge Region of the Human IgA1 Immunoglobulin Molecule,' Biophys Chem, Aug. 1988 (Aug. 1988), 31(1-2):35-44.
Simplicio AL et a;., 'Prodrugs for Amines,' Molecules, Mar. 2008 (Mar. 2008), 13(3):519-47.
Singapore Search Report and Written Opinion Issued for corresponding Singapore application No. 11201505860X, dated Apr. 18, 2016.
Singapore Search Report and Written Opinion Issued for corresponding Singapore application No. 11201505862T, dated Apr. 18, 2016.
Singapore Search Report and Written Opinion Issued for corresponding Singapore application No. 11201505934X, dated Apr. 27, 2016.
Singapore Search Report and Written Opinion Issued for corresponding Singapore application No. 11201505937S, dated May 5, 2016.
Singapore Search Report and Written Opinion Issued for corresponding Singapore application No. 11201505942Y, dated Mar. 22, 2016.
Stanton PK et al., 'Inhibition of the Production and Maintenance of Long-Term Potentiation in Rat Hippocampal Slices by a Monoclonal Antibody,' Proc Natl Acad Sci USA, Mar. 1987 (Mar. 1987), 84(6):1684-8.
Stanton PK et al., 'Neuroprotection by a Novel NMDAR Functional Glycine Site Partial Agonist, GLYX-13,' Neuroreport, Aug. 26, 2009 (Aug. 26, 2009), 20(13):1193-7.
Tanwar MK et al., 'Gene Expression Microarray Analysis Reveals YLK-40 to be a Potential Serum Marker for Malignant Character in Human Glioma,' Cancer Res, Aug. 1, 2002 (Aug. 1, 2002), 62(15):4364-8.

Thompson LT et al., 'Hippocampus-Dependent Learning Facilitated by a Monoclonal Antibody or D-Cycloserine,' Nature, Oct. 15, 1992 (Oct. 15, 1992), 359(6396):638-41.
Turturro A et al., 'Growth Curves and Survival Characteristics of the Animals Used in the Biomarkers of Aging Program,' J Gerentol A Biol Sci Med Sci, Nov. 1999 (Nov. 1999), 54A(11):B492-B501.
Various, *The NMDA Receptor*, (2nd ed. 1994), GL Collingridge and JC Watkins Eds., Oxford. University Press, Inc., New York, New York US (Publ), pp. 1-479 ISBN: 0-19-262371-0.
Wood PL et al., 'Antinociceptive Action of GLYX-13: An N-Methyl-D-aspartate Receptor Glycine Site Partial Agonist,' Neuroreport, Jul. 2, 2008 (Jul. 2, 2008), 19(10):1061-3.
Wood PL, 'The NMDA Receptor Complex: A Long and Winding Road to Therapeutics,' IDrugs, Mar. 2005 (Mar. 2005), 8(3):229-35.
Wood SG et al., 'Tetrapeptide Inhibitors of the IgA1 Proteinases from Type I Neisseria gonorrhoeae,' J Med Chem, Oct. 1989 (Oct. 1989), 32(10):2407-11.
Zhang X-L et al., 'A NMDA Receptor Glycine Site Partial Agonist, GLYX-13, Simultaneously Enhances LTP and Reduces LTD at Schaffer Collateral-CA1 Synapses in Hippocampus,' Neuropharmacology, Aug. 29, 2008 (Aug. 29, 2008), 55(7):1238-50.
U.S. Appl. No. 13/051,237, NMDA Receptor Modulators and Uses Thereof, filed Mar. 18, 2011, Abandoned, US 2011-0306586 Published on Dec. 15, 2011.
U.S. Appl. No. 14/050,641, NMDA Receptor Modulators and Uses Thereof, filed Oct. 10, 2013, Patented, U.S. Pat. No. 9,512,133 Issued Dec. 6, 2016.
U.S. Appl. No. 14/580,803, NMDA Receptor Modulators and Uses Thereof, filed Dec. 23, 2014, Patented, U.S. Pat. No. 9,802,946 Issued Oct. 31, 2017.
U.S. Appl. No. 15/785,603, NMDA Receptor Modulators and Uses Thereof, filed Oct. 17, 2017, Published, US 2019-0077807 Published on Mar. 14, 2019.
U.S. Appl. No. 16/006,125, Spiro-Lactam NMDA Modulators and Methods of Using Same, filed Jun. 12, 2018, Patented, U.S. Pat. No. 10,150,769 Issued on Dec. 11, 2018.
U.S. Appl. No. 16/197,584, Spiro-Lactam NMDA Modulators and Methods of Using Same, filed Nov. 21, 2018, Pending.
U.S. Appl. No. 16/322,604, Spiro-Lactam NMDA Modulators and Methods of Using Same, filed Feb. 1, 2019, Pending, US 2019-0194200 Published on Jun. 27, 2019.
U.S. Appl. No. 14/764,395, Spiro-Lactam NMDA Receptor Modulators and Uses Thereof, filed Jul. 29, 2015, Patented, U.S. Pat. No. 9,512,134 Issued Dec. 6, 2016.
U.S. Appl. No. 14/932,579, Spiro-Lactam NMDA Receptor Modulators and Uses Thereof, filed Nov. 4, 2015, Patented, U.S. Pat. No. 9,504,670 Issued Nov. 29, 2016.
U.S. Appl. No. 15/049,577, Spiro-Lactam NMDA Receptor Modulators and Uses Thereof, filed Feb. 22, 2016, Patented, U.S. Pat. No. 9,579,304 Issued Feb. 28, 2017.
U.S. Appl. No. 15/337,605, Spiro-Lactam NMDA Receptor Modulators and Uses Thereof, filed Oct. 28, 2016, patented, U.S. Pat. No. 10,052,308 Issued on Aug. 21, 2018.
U.S. Appl. No. 15/969,186, Spiro-Lactam NMDA Receptor Modulators and Uses Thereof, filed May 2, 2018, Published, US 2018-0250267 Published on Sep. 6, 2018.
U.S. Appl. No. 15/969,200, Spiro-Lactam NMDA Receptor Modulators and Uses Thereof, filed May 2, 2018, Published, US 2018-0250268 Published on Sep. 6, 2018.
U.S. Appl. No. 14/764,402, Spiro-Lactam NMDA Receptor Modulators and Uses Thereof, filed Jul. 29, 2015, Patented, U.S. Pat. No. 9,828,384 Issued Nov. 28, 2017.
U.S. Appl. No. 15/671,409, Spiro-Lactam NMDA Receptor Modulators and Uses Thereof, filed Aug. 8, 2017, Published, US 2018-0179218 Published on Jun. 28, 2018.
U.S. Appl. No. 15/938,040, Spiro-Lactam NMDA Receptor Modulators and Uses Thereof, filed Mar. 28, 2018, Published, US 2018-0215767 Published on Aug. 2, 2018.
U.S. Appl. No. 15/968,976, Spiro-Lactam NMDA Receptor Modulators and Uses Thereof, filed May 2, 2018, Published, US 2018-0244680 Published on Aug. 30, 2018.

(56) References Cited

OTHER PUBLICATIONS

U.S. Appl. No. 14/764,411, Spiro-Lactam NMDA Receptor Modulators and Uses Thereof, filed Jul. 29, 2015, Patented, U.S. Pat. No. 9,758,525 Issued Sep. 12, 2017.
U.S. Appl. No. 15/667,014, Spiro-Lactam NMDA Receptor Modulators and Uses Thereof, filed Aug. 2, 2017, Published, US 2018-0179217 Published on Jun. 28, 2018.
U.S. Appl. No. 14/764,419, Spiro-Lactam NMDA Receptor Modulators and Uses Thereof, filed Jul. 29, 2015, Published, U.S. Pat. No. 9,738,650 Issued Aug. 22, 2017.
U.S. Appl. No. 15/653,738, Spiro-Lactam NMDA Receptor Modulators and Uses Thereof, filed Jul. 19, 2017, Patented, U.S. Pat. No. 10,253,032 Issued Apr. 9, 2019.
U.S. Appl. No. 14/764,426, Spiro-Lactam NMDA Receptor Modulators and Uses Thereof, filed Jul. 29, 2015, Patented, U.S. Pat. No. 9,708,335 Issued Jul. 18, 2017.
U.S. Appl. No. 15/625,163, Spiro-Lactam NMDA Receptor Modulators and Uses Thereof, filed Jun. 16, 2017, Published, US 2018-0127430 Published on May 10, 2018.
U.S. Appl. No. 16/321,903, Spiro-Lactam NMDA Receptor Modulators and Uses Thereof, filed Jan. 30, 2019, Pending, US 2019-0175588 Published on Jun. 13, 2019.
U.S. Appl. No. 16/321,905, Spiro-Lactam NMDA Receptor Modulators and Uses Thereof, filed Jan. 30, 2019, Pending, US 2019-0177334 Published on Jun. 13, 2019.
U.S. Appl. No. 16/321,906, Spiro-Lactam and Bis-Spiro-Lactam NMDA Receptor Modulators and Uses Thereof, filed Jan. 30, 2019, Pending.
U.S. Appl. No. 15/638,669, Spiro-Lactam NMDA Receptor Modulators and Uses Thereof, filed Jun. 30, 2017, Patented, U.S. Pat. No. 9,932,347 Issued Apr. 3, 2018.
U.S. Appl. No. 15/830,378, Spiro-Lactam NMDA Receptor Modulators and Uses Thereof, filed Dec. 4, 2017, Patented, U.S. Pat. No. 10,196,401 Issued on Feb. 5, 2019.
U.S. Appl. No. 15/636,888, Spiro-Lactam NMDA Receptor Modulators and Uses Thereof, filed Jun. 29, 2017, Patented, U.S. Pat. No. 9,925,169 Issued Mar. 27, 2018.
U.S. Appl. No. 15/830,383, Spiro-Lactam NMDA Receptor Modulators and Uses Thereof, filed Dec. 4, 2017, Patented, U.S. Pat. No. 10,195,179 Issued on Feb. 5, 2019.

* cited by examiner

SPIRO-LACTAM NMDA RECEPTOR MODULATORS AND USES THEREOF

CROSS REFERENCE TO RELATED APPLICATIONS

This application is a national stage application under 35 U.S.C. § 371 of International Application No. PCT/US2017/044813, filed on Aug. 1, 2017, which application claims priority to and the benefit of U.S. Provisional Patent Application No. 62/523,413, filed on Jun. 22, 2017, and U.S. Provisional Patent Application No. 62/369,465, filed on Aug. 1, 2016; the contents of each of which are hereby incorporated by reference herein in their entirety.

BACKGROUND

An N-methyl-d-aspartate ("NMDA") receptor is a postsynaptic, ionotropic receptor that is responsive to, inter alia, the excitatory amino acids glutamate and glycine and the synthetic compound NMDA. The NMDA receptor controls the flow of both divalent and monovalent ions into the postsynaptic neural cell through a receptor associated channel (Foster et al., Nature 1987, 329:395-396; Mayer et al., Trends in Pharmacol. Sci. 1990, 11:254-260). The NMDA receptor has been implicated during development in specifying neuronal architecture and synaptic connectivity, and may be involved in experience-dependent synaptic modifications. In addition, NMDA receptors are also thought to be involved in long term potentiation and central nervous system disorders.

The NMDA receptor plays a major role in the synaptic plasticity that underlies many higher cognitive functions, such as memory acquisition, retention and learning, as well as in certain cognitive pathways and in the perception of pain (Collingridge et al., The NMDA Receptor, Oxford University Press, 1994). In addition, certain properties of NMDA receptors suggest that they may be involved in the information-processing in the brain that underlies consciousness itself.

The NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level of intracellular calcium which activates a biochemical cascade resulting in protein degradation and cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's and Parkinson's related conditions such as dyskinesia and L-dopa induced dyskinesia and Alzheimer's diseases. Activation of the NMDA receptor has been shown to be responsible for post-stroke convulsions, and, in certain models of epilepsy, activation of the NMDA receptor has been shown to be necessary for the generation of seizures. Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The first two types of subunits discovered so far form a large extracellular region, which probably contains most of the allosteric binding sites, several transmembrane regions looped and folded so as to form a pore or channel, which is permeable to $Ca^{++}$, and a carboxyl terminal region. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

A need continues to exist in the art for novel and more specific and/or potent compounds that are capable of modulating NMDA receptors, and provide pharmaceutical benefits. In addition, a need continues to exist in the medical arts for orally deliverable forms of such compounds.

SUMMARY

The present disclosure includes compounds that can be NMDA modulators. More specifically, the present disclosure provides a compound having the formula:

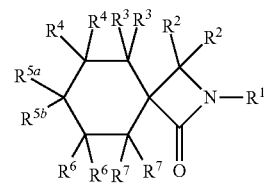

or a stereoisomer and/or a pharmaceutically acceptable salt thereof, where:

$R^1$ is selected from the group consisting of H, —$C_1$-$C_4$alkyl, —$C_1$-$C_4$alkyl-phenyl, —C(O)—$R^{31}$, —C(O)—O—$R^{32}$, phenyl, and —CH($R^8$)—C(O)—$R^9$; wherein phenyl is optionally substituted by one, two or three substituents each independently selected from —$C_1$-$C_4$alkyl, —$C_1$-$C_4$alkoxy, hydroxyl, and halogen;

$R^2$ is independently selected for each occurrence from the group consisting of H, —$C_1$-$C_4$alkyl, and —$C_1$-$C_4$haloalkyl;

$R^3$, $R^4$, $R^6$, and $R^7$ are each independently selected for each occurrence from the group consisting of H, hydroxyl, halogen, cyano, —$C_1$-$C_4$alkyl, and —$C_1$-$C_4$haloalkyl; or $R^3$ and $R^4$ taken together with the adjacent carbons to which they are attached form a 3-membered carbocyclic ring which is optionally substituted by one or two substituents independently selected from the group consisting of halogen, hydroxyl, —$C_1$-$C_3$alkyl, —$C_1$-$C_3$alkoxy, —C(O)N$R^aR^b$, and —N$R^aR^b$;

$R^{5a}$ is selected from the group consisting of H, hydroxyl, halogen, cyano, —$C_1$-$C_4$alkoxy, —O—$C_1$-$C_4$ alkyl-phenyl, —$C_1$-$C_4$alkyl, —C(O)—$C_1$-$C_4$alkyl, —N$R^a$—C(O)—$C_1$-$C_4$alkyl, —N$R^a$—C(O)—O—$C_1$-$C_4$alkyl, —N$R^aR^b$, and —N$R^a$CH($R^{10}$)—C(O)—$R^{11}$; wherein $C_1$-$C_4$alkyl is optionally substituted by one, two or three substituents each independently selected from —COOH, —C(O)NH$_2$, —N$R^aR^b$, —SH, —C(O)—

$C_1$-$C_4$alkyl, —C(O)—O—$C_1$-$C_4$alkyl, —O—C(O)—$C_1$-$C_4$alkyl, —$C_1$-$C_4$alkoxy, phenyl, hydroxyl, and halogen; and phenyl, independently for each occurrence is optionally substituted by one, two or three substituents each independently selected from —$C_1$-$C_4$alkyl, —$C_1$-$C_4$haloalkyl, —$C_1$-$C_4$alkoxy, —$NR^aR^b$, hydroxyl, cyano, and halogen;

$R^{5b}$ is selected from the group consisting of H, halogen, cyano, —$C_1$-$C_4$alkyl, and —$C_1$-$C_4$haloalkyl; or $R^{5a}$ and $R^{5b}$ taken together form an oxo group;

$R^8$ and $R^{10}$ are independently selected from the group consisting of H and —$C_1$-$C_4$alkyl, wherein $C_1$-$C_4$alkyl is optionally substituted by one, two or three substituents each independently selected from —$C(O)NR^aR^b$, —$NR^a$—C(O)—$C_1$-$C_4$alkyl, —$NR^aR^b$, —SH, —C(O)—$C_1$-$C_4$alkyl, —C(O)—O—$C_1$-$C_4$alkyl, —O—C(O)—$C_1$-$C_4$alkyl, —$C_1$-$C_4$alkoxy, —COOH, hydroxyl, and halogen;

$R^9$ and $R^{11}$ are independently selected from the group consisting of hydroxyl, —$C_1$-$C_4$alkoxy, and —$NR^aR^b$;

$R^{31}$ is selected from the group consisting of hydrogen, —$C_1$-$C_6$alkyl, —$C_1$-$C_6$haloalkyl, —$C_3$-$C_6$cycloalkyl, and phenyl;

$R^{32}$ is selected from the group consisting of hydrogen, —$C_1$-$C_6$alkyl, —$C_1$-$C_6$haloalkyl, —$C_3$-$C_6$cycloalkyl, benzyl, and phenyl; and $R^a$ and $R^b$ are each independently selected for each occurrence from the group consisting of H, —$C_1$-$C_4$alkyl, —$C_1$-$C_4$alkyl-phenyl, —$C_1$-$C_4$alkyl-$C_3$-$C_7$cycloalkyl, —$C_1$-$C_4$alkyl-heterocycloalkyl, and —$C_1$-$C_4$alkyl-heteroaryl, wherein heterocycloalkyl and heteroaryl include 1, 2, or 3 ring atoms independently selected from N, O and S, and phenyl is optionally substituted by one, two or three substituents selected from halogen, hydroxyl, —C(O)$NH_2$, —C(O)NH($C_1$-$C_4$alkyl), —C(O)N($C_1$-$C_4$alkyl)$_2$, —$C_1$-$C_3$alkyl and —$C_1$-$C_3$alkoxy; or $R^a$ and $R^b$ taken together with the nitrogen to which they are attached form a 4-6-membered heterocycloalkyl or a 5-8-membered heteroaryl.

In various embodiments, the present disclosure provides a compound having the formula:

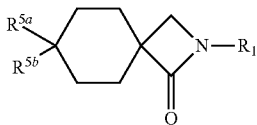

or a stereoisomer and/or a pharmaceutically acceptable salt thereof, where:

$R^1$ is selected from the group consisting of H, —$C_1$-$C_4$alkyl, —$C_1$-$C_4$alkyl-phenyl, and —CH($R^8$)—C(O)—$R^9$; wherein phenyl is optionally substituted by one, two or three substituents each independently selected from —$C_1$-$C_4$alkyl, $C_1$-$C_4$alkoxy, hydroxyl, and halogen; and $R^{5a}$ is selected from the group consisting of H, hydroxyl, halogen, cyano, —$C_1$-$C_4$alkoxy, —O—$C_1$-$C_4$ alkyl-phenyl, —$C_1$-$C_4$alkyl, —C(O)—$C_1$-$C_4$alkyl, —$NR^a$—C(O)—$C_1$-$C_4$alkyl, —$NR^a$—C(O)—O—$C_1$-$C_4$alkyl, —$NR^aR^b$, and —$NR^a$CH($R^{10}$)—C(O)—$R^{11}$; wherein $C_1$-$C_4$alkyl is optionally substituted by one, two or three substituents each independently selected from —COOH, —C(O)$NH_2$, —$NR^aR^b$, —SH, —C(O)—$C_1$-$C_4$alkyl, —C(O)—O—$C_1$-$C_4$alkyl, —O—C(O)—$C_1$-$C_4$alkyl, —$C_1$-$C_4$alkoxy, hydroxyl, and halogen; and phenyl is optionally substituted by one, two or three substituents each independently selected from —$C_1$-$C_4$alkyl, —$C_1$-$C_4$haloalkyl, —$C_1$-$C_4$alkoxy, —$NR^aR^b$, hydroxyl, and halogen;

$R^{5b}$ is selected from the group consisting of H, halogen, —$C_1$-$C_4$alkyl, and —$C_1$-$C_4$haloalkyl; or $R^{5a}$ and $R^{5b}$ taken together form an oxo group;

$R^8$ and $R^{10}$ are selected independently from the group consisting of H and —$C_1$-$C_4$alkyl, wherein $C_1$-$C_4$alkyl is optionally substituted by one, two or three substituents each independently selected from —$C(O)NR^aR^b$, —$NR^a$—C(O)—$C_1$-$C_4$alkyl, —$NR^aR^b$, —SH, —C(O)—$C_1$-$C_4$alkyl, —C(O)—O—$C_1$-$C_4$alkyl, —O—C(O)—$C_1$-$C_4$alkyl, $C_1$-$C_4$alkoxy, —COOH, hydroxyl, and halogen;

$R^9$ and $R^{11}$ are selected independently from the group consisting of hydroxyl, $C_1$-$C_4$alkoxy, and —$NR^aR^b$; and $R^a$ and $R^b$ are each independently selected for each occurrence from the group consisting of H, —$C_1$-$C_4$alkyl, —$C_1$-$C_4$alkyl-phenyl, —$C_1$-$C_4$alkyl-$C_3$-$C_7$cycloalkyl, —$C_1$-$C_4$alkyl-heterocycloalkyl, and —$C_1$-$C_4$alkyl-heteroaryl, wherein heterocycloalkyl and heteroaryl include 1, 2, or 3 ring atoms independently selected from N, O and S, and phenyl is optionally substituted by one, two or three substituents selected from halogen, hydroxyl, —C(O)$NH_2$, —C(O)NH($C_1$-$C_4$alkyl), —C(O)N($C_1$-$C_4$alkyl)$_2$, —$C_1$-$C_3$alkyl and —$C_1$-$C_3$alkoxy; or $R^a$ and $R^b$ taken together with the nitrogen to which they are attached form a 4-6-membered heterocycloalkyl or a 5-8-membered heteroaryl.

In some embodiments, the present disclosure provides a compound having the formula:

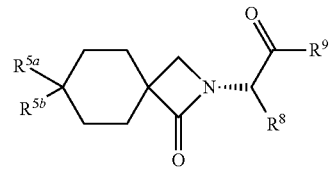

or a stereoisomer and/or a pharmaceutically acceptable salt thereof, where:

$R^{5a}$ is selected from the group consisting of H, hydroxyl, halogen, —$CH_3$, —C(O)—$C_1$-$C_4$alkyl, —O—$CH_2$-Ph, —$NH_2$, —NH—$C_1$-$C_4$alkyl, —NH—C(O)—$C_1$-$C_4$alkyl, —NH—C(O)—O—$C_1$-$C_4$alkyl, and —$NR^a$CH($R^{10}$)—C(O)—$R^{11}$; wherein $C_1$-$C_4$alkyl is optionally substituted by one or two substituents each independently selected from —C(O)$NH_2$, —$NH_2$, —SH, —OC(O)$CH_3$, hydroxyl, and halogen;

$R^{5b}$ is H or halogen;

$R^8$ and $R^{10}$ are selected independently from the group consisting of H and $C_1$-$C_4$alkyl, wherein the $C_1$-$C_4$alkyl may be optionally substituted by one, two or three substituents each independently selected from —$C(O)NR^aR^b$, —$NR^a$—C(O)—$C_1$-$C_4$alkyl, —$NR^aR^b$, —SH, —C(O)—$C_1$-$C_4$alkyl, —C(O)—O—$C_1$-$C_4$alkyl, —O—C(O)—$C_1$-$C_4$alkyl, $C_1$-$C_4$alkoxy, —COOH, hydroxyl, and halogen; and $R^9$ and $R^{11}$ are selected independently from the group consisting of hydroxyl, $C_1$-$C_4$alkoxy, and —$NR^aR^b$; and $R^a$ and $R^b$ are each independently selected for each occurrence from the group consisting of H, —$C_1$-$C_4$alkyl, —$C_1$-$C_4$alkyl-phenyl, —$C_1$-$C_4$alkyl-$C_3$-$C_7$cycloalkyl, —$C_1$-$C_4$alkyl-heterocycloalkyl, and —$C_1$-$C_4$alkyl-heteroaryl, wherein heterocycloalkyl and heteroaryl include 1, 2, or 3 ring atoms independently selected from N, O and S, and phenyl is optionally substituted by one, two or three substituents selected from halogen, hydroxyl, —C(O)NH$_2$, —C(O)NH(C$_1$-C$_4$alkyl), —C(O)N(C$_1$-C$_4$alkyl)$_2$, —C$_1$-C$_3$alkyl and —C$_1$-C$_3$alkoxy; or $R^a$ and $R^b$ taken together with the nitrogen to which they are attached form a 4-6-membered heterocycloalkyl or a 5-8-membered heteroaryl.

Also provided herein are pharmaceutical compositions comprising a disclosed compound, and a pharmaceutically acceptable excipient. Such compositions can be suitable for administration to a patient orally, parenterally, topically, intravaginally, intrarectally, sublingually, ocularly, transdermally, or nasally.

In various embodiments, the compounds described herein bind to NMDA receptors expressing certain NR2 subtypes. In some embodiments, the compounds described herein bind to one NR2 subtype and not another. It is appreciated that disclosed compounds may bind to another protein target and/or another NMDA receptor type.

In another aspect, a method of treating a condition selected from the group consisting of autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder, phobia, post-traumatic stress syndrome, a behavior disorder, an impulse control disorder, a substance abuse disorder, a sleep disorder, a memory disorder, a learning disorder, urinary incontinence, multiple system atrophy, progressive supra-nuclear palsy, Friedrich's ataxia, Down's syndrome, fragile X syndrome, tuberous sclerosis, olivio-ponto-cerebellar atrophy, Rett syndrome, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, Tourette's syndrome, epilepsy, infantile spasms, cerebral ischemia, stroke, a brain tumor, traumatic brain injury, cardiac arrest, myelopathy, spinal cord injury, peripheral neuropathy, fibromyalgia, acute neuropathic pain, and chronic neuropathic pain, in a patient in need thereof is provided. Such methods may comprise administering to the patient a pharmaceutically effective amount of a disclosed compound or pharmaceutically acceptable salts, stereoisomers, N-oxides, and hydrates thereof.

In some embodiments, a disclosed method includes treating neuropathic pain, wherein the neuropathic pain is selected from the group consisting of herpes, HIV, traumatic nerve injury, stroke, post-ischemia, chronic back pain, postherpetic neuralgia, fibromyalgia, reflex sympathetic dystrophy, complex regional pain syndrome, spinal cord injury, sciatica, phantom limb pain, diabetic neuropathy, and cancer chemotherapeutic-induced neuropathic pain.

In some embodiments, a disclosed method includes treating depression. For example, depression may include one or more of major depressive disorder, dysthymic disorder, psychotic depression, postpartum depression, seasonal affective disorder, bipolar disorder, mood disorder, or depression caused by a chronic medical condition. In other embodiments, a disclosed method may treat schizophrenia. Such schizophrenia may be, for example, paranoid type schizophrenia, disorganized type schizophrenia, catatonic type schizophrenia, undifferentiated type schizophrenia, residual type schizophrenia, post-schizophrenic depression, or simple schizophrenia.

DETAILED DESCRIPTION

This disclosure is generally directed to compounds that are capable of modulating NMDA receptors, for example, NMDA receptor antagonists, agonists, or partial agonists, and compositions and/or methods of using the disclosed compounds. It should be appreciated that the disclosed compounds may modulate other protein targets and/or specific NMDA receptor subtype.

The term "alkyl," as used herein, refers to a saturated straight-chain or branched hydrocarbon, such as a straight-chain or branched group of 1-6, 1-4, or 1-3 carbon atoms, referred to herein as $C_1$-$C_6$ alkyl, $C_1$-$C_4$ alkyl, and $C_1$-$C_3$ alkyl, respectively. For example, "$C_1$-$C_6$ alkyl" refers to a straight-chain or branched saturated hydrocarbon containing 1-6 carbon atoms. Examples of a $C_1$-$C_6$ alkyl group include, but are not limited to, methyl, ethyl, propyl, butyl, pentyl, hexyl, isopropyl, isobutyl, sec-butyl, tert-butyl, isopentyl, and neopentyl. In another example, "$C_1$-$C_4$ alkyl" refers to a straight-chain or branched saturated hydrocarbon containing 1-4 carbon atoms. Examples of a $C_1$-$C_4$ alkyl group include, but are not limited to, methyl, ethyl, propyl, butyl, isopropyl, isobutyl, sec-butyl and tert-butyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl.

The term "alkoxy," as used herein, refers to an alkyl group attached to an oxygen atom (alkyl-O—). Alkoxy groups can have 1-6 or 2-6 carbon atoms and are referred to herein as $C_1$-$C_6$ alkoxy and $C_2$-$C_6$ alkoxy, respectively. Exemplary alkoxy groups include, but are not limited to, methoxy, ethoxy, propyloxy, isopropoxy, and tert-butoxy.

The term "haloalkyl" as used herein refers to an alkyl group, in which one or more hydrogen atoms of the alkyl group are replaced with one or more independently selected halogens. A haloalkyl group can have 1 to 10 carbon atoms (i.e., $C_1$-$C_{10}$ haloalkyl group), for example, 1 to 6 carbon atoms (i.e., $C_1$-$C_6$ haloalkyl group). Examples of haloalkyl groups include —$CF_3$, —$C_2F_5$, —$CHF_2$, —$CH_2F$, —$CCl_3$, —$CHCl_2$, —$CH_2Cl_1$, —$CH_2CH_2Cl_1$, —$CHFCH_2Cl_1$, and —$C_2Cl_5$. Perhaloalkyl groups, i.e., alkyl groups where all of the hydrogen atoms are replaced with halogen atoms (e.g., —$CF_3$ and —$C_2F_5$), are included within the definition of "haloalkyl."

The term "carbonyl," as used herein, refers to the radical —C(O)— or C=O.

The term "cyano," as used herein, refers to the radical —CN.

The phrase, "carbocyclic ring," as used herein, refers to a hydrocarbon ring system in which all the ring atoms are carbon. Exemplary carbocyclic rings including cycloalkyls and phenyl.

The term "cycloalkyl," as used herein, refers to a monocyclic saturated or partially unsaturated hydrocarbon ring (carbocyclic) system, for example, where each ring is either completely saturated or contains one or more units of unsaturation, but where no ring is aromatic. A cycloalkyl can have 3-6 or 4-6 carbon atoms in its ring system, referred to herein as $C_3$-$C_6$ cycloalkyl or $C_4$-$C_6$ cycloalkyl, respectively. Exemplary cycloalkyl groups include, but are not limited to, cyclohexyl, cyclohexenyl, cyclopentyl, cyclopentenyl, cyclobutyl, and cyclopropyl.

The terms "halo" and "halogen," as used herein, refer to fluoro (F), chloro (Cl), bromo (Br), and/or iodo (I).

The term "heteroatom," as used herein, refers to an atom of any element other than carbon or hydrogen and includes, for example, nitrogen (N), oxygen (O), silicon (Si), sulfur (S), phosphorus (P), and selenium (Se).

The term "heterocycloalkyl," as used herein, is art-recognized and refer to saturated or partially unsaturated 3- to 8-membered ring structures, whose ring system include one, two or three heteroatoms, such as nitrogen, oxygen, and/or sulfur. A heterocycloalkyl can be fused to one or more phenyl, partially unsaturated, or saturated rings. Examples of heterocycloalkyls include, but are not limited to, pyrrolidinyl, piperidinyl, morpholinyl, thiomorpholinyl, and piperazinyl.

The term "heteroaryl," as used herein, refers to a monocyclic aromatic 5- to 8-membered ring system containing one or more heteroatoms, for example, one to three heteroatoms, such as nitrogen, oxygen, and sulfur. Where possible, a heteroaryl can be linked to the adjacent radical though carbon or nitrogen. Examples of heteroaryls include, but are not limited to, furan, thiophene, pyrrole, thiazole, oxazole, isothiazole, isoxazole, imidazole, pyrazole, triazole, pyridine, and pyrimidine.

The terms "hydroxy" and "hydroxyl," as used herein, refer to the radical —OH.

The term "oxo," as used herein, refers to the radical =O (double bonded oxygen).

The term "amino acid," as used herein, includes any one of the following alpha amino acids: isoleucine, alanine, leucine, asparagine, lysine, aspartate, methionine, cysteine, phenylalanine, glutamate, threonine, glutamine, tryptophan, glycine, valine, proline, arginine, serine, histidine, and tyrosine. An amino acid also can include other art-recognized amino acids such as beta amino acids.

The term "compound," as used herein, refers to the compound itself and its pharmaceutically acceptable salts, hydrates, esters and N-oxides including its various stereoisomers and its isotopically-labelled forms, unless otherwise understood from the context of the description or expressly limited to one particular form of the compound, i.e., the compound itself, a specific stereoisomer and/or isotopically-labelled compound, or a pharmaceutically acceptable salt, a hydrate, an ester, or an N-oxide thereof. It should be understood that a compound can refer to a pharmaceutically acceptable salt, or a hydrate, an ester or an N-oxide of a stereoisomer of the compound and/or an isotopically-labelled compound.

The term "moiety," as used herein, refers to a portion of a compound or molecule.

The compounds of the disclosure can contain one or more chiral centers and/or double bonds and therefore, can exist as stereoisomers, such as geometric isomers, and enantiomers or diastereomers. The term "stereoisomers," when used herein, consists of all geometric isomers, enantiomers and/or diastereomers of the compound. For example, when a compound is shown with specific chiral center(s), the compound depicted without such chirality at that and other chiral centers of the compound are within the scope of the present disclosure, i.e., the compound depicted in two-dimensions with "flat" or "straight" bonds rather than in three dimensions, for example, with solid or dashed wedge bonds. Stereospecific compounds may be designated by the symbols "R" or "S," depending on the configuration of substituents around the stereogenic carbon atom. The present disclosure encompasses all the various stereoisomers of these compounds and mixtures thereof. Mixtures of enantiomers or diastereomers can be designated "(±)" in nomenclature, but a skilled artisan will recognize that a structure can denote a chiral center implicitly. It is understood that graphical depictions of chemical structures, e.g., generic chemical structures, encompass all stereoisomeric forms of the specified compounds, unless indicated otherwise.

Individual enantiomers and diastereomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns, or (4) kinetic resolution using stereoselective chemical or enzymatic reagents. Racemic mixtures also can be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. See, for example, Carreira and Kvaerno, Classics in Stereoselective Synthesis, Wiley-VCH: Weinheim, 2009.

Geometric isomers, resulting from the arrangement of substituents around a carbon-carbon double bond or arrangement of substituents around a cycloalkyl or heterocycloalkyl, can also exist in the compounds of the present disclosure. The symbol  denotes a bond that may be a single, double or triple bond as described herein. Substituents around a carbon-carbon double bond are designated as being in the "Z" or "E" configuration, where the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The disclosure also embraces isotopically-labeled compounds which are identical to those compounds recited herein, except that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $^{2}$H ("D"), $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound described herein can have one or more H atoms replaced with deuterium.

Certain isotopically-labeled compounds (e.g., those labeled with $^{3}$H and $^{14}$C) can be useful in compound and/or substrate tissue distribution assays. Tritiated (i.e., $^{3}$H) and carbon-14 (i.e., $^{14}$C) isotopes can be particularly preferred for their ease of preparation and detectability. Further, substitution with heavier isotopes such as deuterium (i.e., $^{2}$H) can afford certain therapeutic advantages resulting from greater metabolic stability (e.g., increased in vivo half-life or reduced dosage requirements) and hence can be preferred in some circumstances. Isotopically-labeled compounds can generally be prepared by following procedures analogous to those disclosed herein, for example, in the Examples section, by substituting an isotopically-labeled reagent for a non-isotopically-labeled reagent.

The phrases "pharmaceutically acceptable" and "pharmacologically acceptable," as used herein, refer to compounds, molecular entities, compositions, materials, and/or dosage forms that do not produce an adverse, allergic or other untoward reaction when administered to an animal, or a human, as appropriate. For human administration, preparations should meet sterility, pyrogenicity, general safety and purity standards as required by FDA Office of Biologics standards.

The phrases "pharmaceutically acceptable carrier" and "pharmaceutically acceptable excipient," as used herein, refer to any and all solvents, dispersion media, coatings, isotonic and absorption delaying agents, and the like, that are compatible with pharmaceutical administration. Pharmaceutical acceptable carriers can include phosphate buffered saline solution, water, emulsions (e.g., such as an oil/water or water/oil emulsions), and various types of wetting agents. The compositions also can include stabilizers and preservatives.

The phrase "pharmaceutical composition," as used herein, refers to a composition comprising at least one compound as disclosed herein formulated together with one or more pharmaceutically acceptable carriers. The pharmaceutical compositions can also contain other active compounds providing supplemental, additional, or enhanced therapeutic functions.

The terms "individual," "patient," and "subject," as used herein, are used interchangeably and include any animal, including mammals, preferably mice, rats, other rodents, rabbits, dogs, cats, swine, cattle, sheep, horses, or primates, and more preferably, humans. The compounds described in the disclosure can be administered to a mammal, such as a human, but can also be administered to other mammals such as an animal in need of veterinary treatment, for example, domestic animals (e.g., dogs, cats, and the like), farm animals (e.g., cows, sheep, pigs, horses, and the like) and laboratory animals (e.g., rats, mice, guinea pigs, and the like). The mammal treated in the methods described in the disclosure is preferably a mammal in which treatment, for example, of pain or depression, is desired.

The term "treating," as used herein, includes any effect, for example, lessening, reducing, modulating, ameliorating, or eliminating, that results in the improvement of the condition, disease, disorder, and the like, including one or more symptoms thereof. Treating can be curing, improving, or at least partially ameliorating the disorder.

The term "disorder" refers to and is used interchangeably with, the terms "disease," "condition," or "illness," unless otherwise indicated.

The term "modulation," as used herein, refers to and includes antagonism (e.g., inhibition), agonism, partial antagonism, and/or partial agonism.

The phrase "therapeutically effective amount," as used herein, refers to the amount of a compound (e.g., a disclosed compound) that will elicit the biological or medical response of a tissue, system, animal or human that is being sought by the researcher, veterinarian, medical doctor or other clinician. The compounds described in the disclosure can be administered in therapeutically effective amounts to treat a disease. A therapeutically effective amount of a compound can be the quantity required to achieve a desired therapeutic and/or prophylactic effect, such as an amount which results in lessening of a symptom of a disease such as depression.

The phrase "pharmaceutically acceptable salt(s)," as used herein, refers to salt(s) of acidic or basic groups that can be present in compounds of the disclosure and/or used in the compositions of the disclosure. A pharmaceutically acceptable salt (e.g., acid or base) of a compound of the present disclosure, upon administration to a patient, is capable of providing a compound of this invention or an active metabolite or residue thereof.

Compounds included in the present compositions that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

Compounds included in the present compositions that include a basic or acidic moiety can also form pharmaceutically acceptable salts with various amino acids. The compounds of the disclosure can contain both acidic and basic groups; for example, one amino and one carboxylic acid group. In such a case, the compound can exist as an acid addition salt, a zwitterion, or a base salt.

The compounds disclosed herein can exist in a solvated form as well as an unsolvated form with pharmaceutically acceptable solvents such as water, ethanol, and the like, and it is intended that the disclosure embrace both solvated and unsolvated forms. In some embodiments, the compound is amorphous. In certain embodiments, the compound is a single polymorph. In various embodiments, the compound is a mixture of polymorphs. In particular embodiments, the compound is in a crystalline form.

The term "prodrug," as used herein, refers to compounds that are transformed in vivo to yield a disclosed compound or a pharmaceutically acceptable salt, hydrate or solvate of the compound. The transformation can occur by various mechanisms (such as by esterase, amidase, phosphatase, oxidative and/or reductive metabolism) in various locations (such as in the intestinal lumen or upon transit into the intestine, blood, or liver). Prodrugs are well known in the art (see e.g., see Rautio, Kumpulainen et al., Nature Reviews Drug Discovery 2008, 7, 255). For example, if a compound described herein or a pharmaceutically acceptable salt, hydrate or solvate of the compound contains a carboxylic acid functional group, a prodrug can be an ester formed by the replacement of the hydrogen atom of the carboxylic acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as 0-dimethylaminoethyl), carbamoyl-$(C_1-C_2)$alkyl, N,N-di$(C_1-C_2)$alkylcarbamoyl-$(C_1-C_2)$alkyl, piperidino-$(C_2-C_3)$alkyl, pyrrolidino-$(C_2-C_3)$alkyl or morpholino$(C_2-C_3)$alkyl.

Similarly, if a compound described herein contains an alcohol functional group, a prodrug can be formed by the replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, $—P(O)(O(C_1-C_6)$alkyl$)_2$ or glycosyl (the radical resulting from the removal of a hydroxyl group of the hemiacetal form of a carbohydrate).

If a compound described herein incorporates an amine functional group, a prodrug can be formed, for example, by creation of an amide or carbamate, an N-acyloxyalkyl derivative, an (oxodioxolenyl) methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. See, for example, Simplicio, et al., *Molecules* 2008, 13, 519 and references therein.

Unless defined otherwise, all technical and scientific terms used herein have the same meaning as commonly understood by one of ordinary skill in the art to which this disclosure pertains.

Throughout the description, where compositions and kits are described as having, including, or comprising specific components, or where processes and methods are described as having, including, or comprising specific steps, it is contemplated that, additionally, there are compositions and kits of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present disclosure, whether explicit or implicit herein. For example, where reference is made to a particular compound, that compound can be used in various embodiments of compositions of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments can be variously combined or separated without parting from the present teachings and disclosure(s). For example, it will be appreciated that all features described and depicted herein can be applicable to all aspects of the disclosure(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also include the specific quantitative value itself, unless specifically stated otherwise. As used herein, the term "about" refers to a ±10% variation from the nominal value unless otherwise indicated or inferred.

Where a percentage is provided with respect to an amount of a component or material in a composition, the percentage should be understood to be a percentage based on weight, unless otherwise stated or understood from the context.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present disclosure remain operable. Moreover, two or more steps or actions can be conducted simultaneously.

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

The use of any and all examples, or exemplary language herein, for example, "such as" or "including," is intended merely to illustrate better the present disclosure and does not pose a limitation on the scope of the disclosure unless claimed. No language in the specification should be construed as indicating any non-claimed element as essential to the practice of the present disclosure.

Further, if a variable is not accompanied by a definition, then the variable is defined as found elsewhere in the disclosure unless understood to be different from the context. In addition, the definition of each variable and/or substituent, for example, $C_1$-$C_6$ alkyl, $R^2$, $R^b$, w and the like, when it occurs more than once in any structure or compound, can be independent of its definition elsewhere in the same structure or compound.

Definitions of the variables and/or substituents in formulae and/or compounds herein encompass multiple chemical groups. The present disclosure includes embodiments where, for example, i) the definition of a variable and/or substituent is a single chemical group selected from those chemical groups set forth herein, ii) the definition is a collection of two or more of the chemical groups selected from those set forth herein, and iii) the compound is defined by a combination of variables and/or substituents in which the variables and/or substituents are defined by (i) or (ii).

Various aspects of the disclosure are set forth herein under headings and/or in sections for clarity; however, it is understood that all aspects, embodiments, or features of the disclosure described in one particular section are not to be limited to that particular section but rather can apply to any aspect, embodiment, or feature of the present disclosure.

Compounds

Disclosed compounds include a compound having the formula

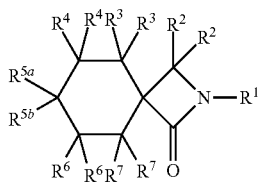

or a stereoisomer and/or a pharmaceutically acceptable salt thereof, where:
$R^1$ is selected from the group consisting of H, —$C_1$-$C_4$alkyl, —$C_1$-$C_4$alkyl-phenyl, —C(O)—$R^{31}$, —C(O)—O—$R^{32}$, phenyl, and —CH($R^8$)—C(O)—$R^9$; wherein phenyl is optionally substituted by one, two or three substituents each independently selected from —$C_1$-$C_4$alkyl, —$C_1$-$C_4$alkoxy, hydroxyl, and halogen;

$R^2$ is independently selected for each occurrence from the group consisting of H, —$C_1$-$C_4$alkyl, and —$C_1$-$C_4$haloalkyl;

$R^3$, $R^4$, $R^6$, and $R^7$ are each independently selected for each occurrence from the group consisting of H, hydroxyl, halogen, cyano, —$C_1$-$C_4$alkyl, and —$C_1$-$C_4$haloalkyl; or $R^3$ and $R^4$ taken together with the adjacent carbons to which they are attached form a 3-membered carbocyclic ring which is optionally substituted by one or two substituents independently selected from the group consisting of halogen, hydroxyl, —$C_1$-$C_3$alkyl, —$C_1$-$C_3$alkoxy, —C(O)N$R^aR^b$, and —N$R^aR^b$;

$R^{5a}$ is selected from the group consisting of H, hydroxyl, halogen, cyano, —$C_1$-$C_4$alkoxy, —O—$C_1$-$C_4$ alkyl-phenyl, —$C_1$-$C_4$alkyl, —C(O)—$C_1$-$C_4$alkyl, —N$R^a$—C(O)—$C_1$-$C_4$alkyl, —N$R^a$—C(O)—O—$C_1$-$C_4$alkyl, —N$R^aR^b$, and —N$R^a$CH($R^{10}$)—C(O)—$R^{11}$; wherein $C_1$-$C_4$alkyl is optionally substituted by one, two or three substituents each independently selected from —COOH, —C(O)N$H_2$, —N$R^aR^b$, —SH, —C(O)—$C_1$-$C_4$alkyl, —C(O)—O—$C_1$-$C_4$alkyl, —O—C(O)—$C_1$-$C_4$alkyl, —$C_1$-$C_4$alkoxy, phenyl, hydroxyl, and halogen; and phenyl, independently for each occurrence is optionally substituted by one, two or three substituents each independently selected from —$C_1$-$C_4$alkyl, —$C_1$-$C_4$haloalkyl, —$C_1$-$C_4$alkoxy, —N$R^aR^b$, hydroxyl, cyano, and halogen;

$R^{5b}$ is selected from the group consisting of H, halogen, cyano, —$C_1$-$C_4$alkyl, and —$C_1$-$C_4$haloalkyl; or $R^{5a}$ and $R^{5b}$ taken together form an oxo group;

$R^8$ and $R^{10}$ are independently selected from the group consisting of H and —$C_1$-$C_4$alkyl, wherein $C_1$-$C_4$alkyl is optionally substituted by one, two or three substituents each independently selected from —C(O)N$R^aR^b$, —N$R^a$—C(O)—$C_1$-$C_4$alkyl, —N$R^aR^b$, —SH, —C(O)—$C_1$-$C_4$alkyl, —C(O)—O—$C_1$-$C_4$alkyl, —O—C(O)—$C_1$-$C_4$alkyl, —$C_1$-$C_4$alkoxy, —COOH, hydroxyl, and halogen;

$R^9$ and $R^{11}$ are independently selected from the group consisting of hydroxyl, —$C_1$-$C_4$alkoxy, and —N$R^aR^b$;

$R^{31}$ is selected from the group consisting of hydrogen, —$C_1$-$C_6$alkyl, —$C_1$-$C_6$haloalkyl, —$C_3$-$C_6$cycloalkyl, and phenyl;

$R^{32}$ is selected from the group consisting of hydrogen, —$C_1$-$C_6$alkyl, —$C_1$-$C_6$haloalkyl, —$C_3$-$C_6$cycloalkyl, benzyl, and phenyl; and $R^a$ and $R^b$ are each independently selected for each occurrence from the group consisting of H, —$C_1$-$C_4$alkyl, —$C_1$-$C_4$alkyl-phenyl, —$C_1$-$C_4$alkyl-$C_3$-$C_7$cycloalkyl, —$C_1$-$C_4$alkyl-heterocycloalkyl, and —$C_1$-$C_4$alkyl-heteroaryl, wherein heterocycloalkyl and heteroaryl include 1, 2, or 3 ring atoms independently selected from N, O and S, and phenyl is optionally substituted by one, two or three substituents selected from halogen, hydroxyl, —C(O)N$H_2$, —C(O)NH($C_1$-$C_4$alkyl), —C(O)N($C_1$-$C_4$alkyl)$_2$, —$C_1$-$C_3$alkyl and —$C_1$-$C_3$alkoxy; or $R^a$ and $R^b$ taken together with the nitrogen to which they are attached form a 4-6-membered heterocycloalkyl or a 5-8-membered heteroaryl.

In certain embodiments, each of $R^3$, $R^4$, $R^6$, and $R^7$ is H.
In certain embodiments, $R^2$ is independently selected for each occurrence from the group consisting of H and methyl.
In some embodiments, $R^2$ is H.

In certain embodiments, R$^1$ is selected from the group consisting of:

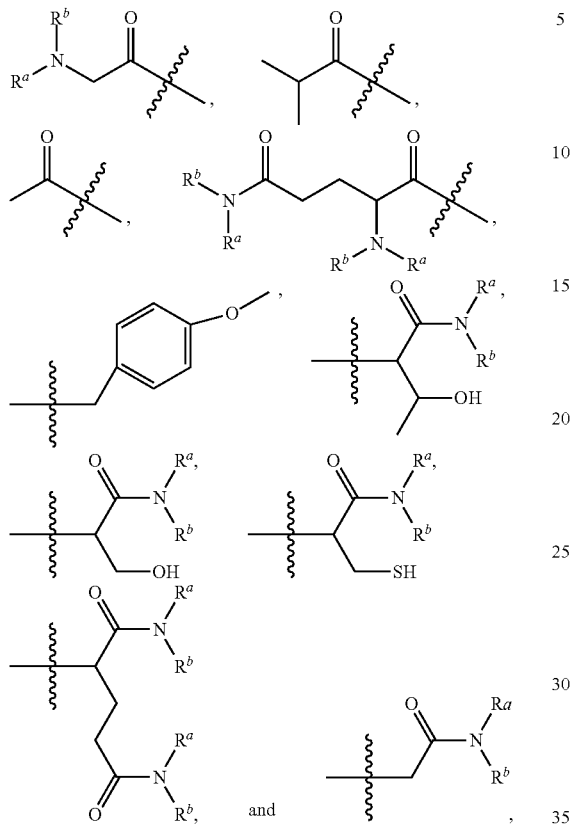

where R$^a$ and R$^b$ are each independently selected for each occurrence from the group consisting of hydrogen and —C$_1$-C$_4$alkyl.

In some embodiments, R$^1$ is selected from the group consisting of H, 4-methoxybenzyl, and —CH(R$^8$)—C(O)—R$^9$; where R$^8$ is selected from the group consisting of H and C$_1$-C$_4$alkyl, where C$_1$-C$_4$alkyl is optionally substituted by one, two or three substituents each independently selected from —C(O)NR$^a$R$^b$, —NR$^a$—C(O)—C$_1$-C$_4$alkyl, —NR$^a$R$^b$, —SH, —C(O)—C$_1$-C$_4$alkyl, —COOH, —C(O)—O—C$_1$-C$_4$alkyl, —O—C(O)—C$_1$-C$_4$alkyl, —C$_1$-C$_4$alkoxy, hydroxyl, and halogen; and R$^9$ is selected from the group consisting of hydroxyl, —C$_1$-C$_4$alkoxy, and —NR$^a$R$^b$.

In various embodiments, R$^8$ is selected from the group consisting of H and —C$_1$-C$_4$alkyl, wherein C$_1$-C$_4$alkyl is optionally substituted by one or two substituents each independently selected from —C(O)NHR$^a$, —NH—C(O)—C$_1$-C$_4$alkyl, —NR$^a$R$^b$, —SH, —C(O)—C$_1$-C$_4$alkyl, —COOH, —C(O)—O—C$_1$-C$_4$alkyl, —O—C(O)—C$_1$-C$_4$alkyl, —C$_1$-C$_4$alkoxy, hydroxyl, and halogen.

In some embodiments, R$^8$ is selected from the group consisting of H and —C$_1$-C$_4$alkyl, where C$_1$-C$_4$alkyl is optionally substituted by one or two substituents each independently selected from —C(O)NH$_2$, —COOH, —NH$_2$, —SH, —O—C(O)—C$_1$-C$_4$alkyl, —C$_1$-C$_4$alkoxy, and hydroxyl.

In certain embodiments, R$^8$ is —C$_1$-C$_4$alkyl, which is optionally substituted by one substituent selected from —C(O)NH2, —NH2, —SH, —OC(O)CH3, and hydroxyl.

In certain embodiments, R$^8$ is selected from the group consisting of H, methyl,

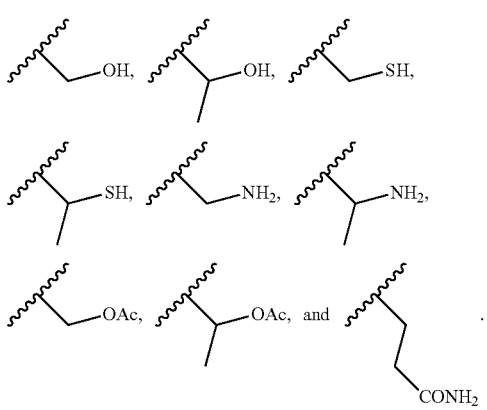

In some embodiments, R$^8$ is selected from the group consisting of H, methyl,

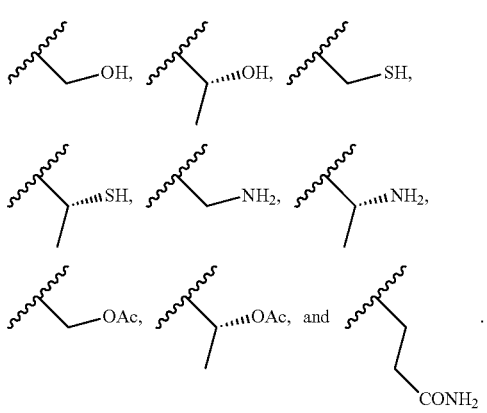

In some embodiments, R$^8$ is

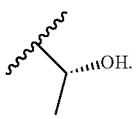

In some embodiments, R$^9$ is —NR$^a$R$^b$.

In certain embodiments, R$^9$ is selected from the group consisting of NH$_2$,

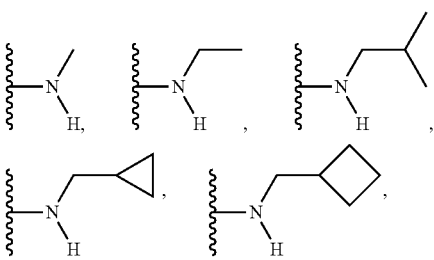

-continued

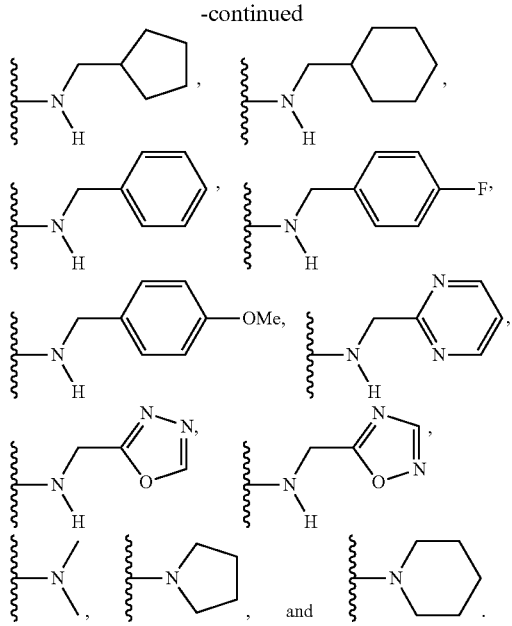

In various embodiments, $R^9$ is $NH_2$.

In some embodiments, $R^{5b}$ is selected from the group consisting of H and halogen.

In certain embodiments, $R^{5b}$ is selected from the group consisting of H and F.

In particular embodiments, $R^{5b}$ is H.

In some embodiments, $R^{5a}$ is selected from the group consisting of H, hydroxyl, halogen, $C_1$-$C_4$alkoxy-phenyl, —$C_1$-$C_4$alkyl, —$NR^a$—C(O)—$C_1$-$C_4$alkyl, —$NR^a$—C(O)—O—$C_1$-$C_4$alkyl, —$NR^aR^b$, and —$NR^aCH(R^{10})$—C(O)—$R^{11}$, where $C_1$-$C_4$alkyl is optionally substituted by one or two substituents each independently selected from —C(O)$NH_2$, —$NR^aR^b$, —SH, —C(O)—$C_1$-$C_4$alkyl, —C(O)—O—$C_1$-$C_4$alkyl, —O—C(O)—$C_1$-$C_4$alkyl, hydroxyl, phenyl and halogen, and where phenyl, independently for each occurrence, is optionally substituted by one or two substituents each independently selected from —$C_1$-$C_4$alkyl, —$C_1$-$C_4$haloalkyl, —$C_1$-$C_4$alkoxy, hydroxyl, cyano and halogen.

In some embodiments, $R^{5a}$ is selected from the group consisting of H, hydroxyl, halogen, —$C_1$-$C_4$alkyl, —O—$CH_2$-Ph, —NH—C(O)—$C_1$-$C_4$alkyl, —NH—C(O)—O—$C_1$-$C_4$alkyl, —$NHR^b$, and —$NR^aCH(R^{10})$—C(O)—$R^{11}$, where $C_1$-$C_4$alkyl is optionally substituted by one or two substituents each independently selected from —C(O)$NH_2$, —$NR^aR^b$, —SH, —O—C(O)—$C_1$-$C_4$alkyl, hydroxyl, and halogen.

In some embodiments, $R^{5a}$ is selected from the group consisting of H, hydroxyl, halogen, methyl, —O—$CH_2$-Ph, —$NH_2$, —NH—$C_1$-$C_4$alkyl, —NH—C(O)—$C_1$-$C_4$alkyl, —NH—C(O)—O—$C_1$-$C_4$alkyl, and —$NR^aCH(R^{10})$—C(O)—$R^{11}$; where $C_1$-$C_4$alkyl is optionally substituted by one or two substituents each independently selected from —C(O)$NH_2$, —$NH_2$, —SH, —OC(O)$CH_3$, hydroxyl, and halogen; $R^{10}$ is selected from the group consisting of H and $C_1$-$C_4$alkyl, where $C_1$-$C_4$alkyl is optionally substituted by one or two substituents each independently selected from —C(O)$NR^aR^b$, —$NR^a$—C(O)—$C_1$-$C_4$alkyl, —$NR^aR^b$, —SH, —C(O)—$C_1$-$C_4$alkyl, —C(O)—O—$C_1$-$C_4$alkyl, —O—C(O)—$C_1$-$C_4$alkyl, —$C_1$-$C_4$alkoxy, —COOH, hydroxyl, and halogen; and $R^{11}$ is selected from the group consisting of hydroxyl, —$C_1$-$C_4$alkoxy, and —$NR^aR^b$.

In some embodiments, $R^{5b}$ is H; and $R^{5a}$ is selected from the group consisting of hydroxyl, halogen, methyl, —O—$CH_2$-Ph, —$NH_2$,

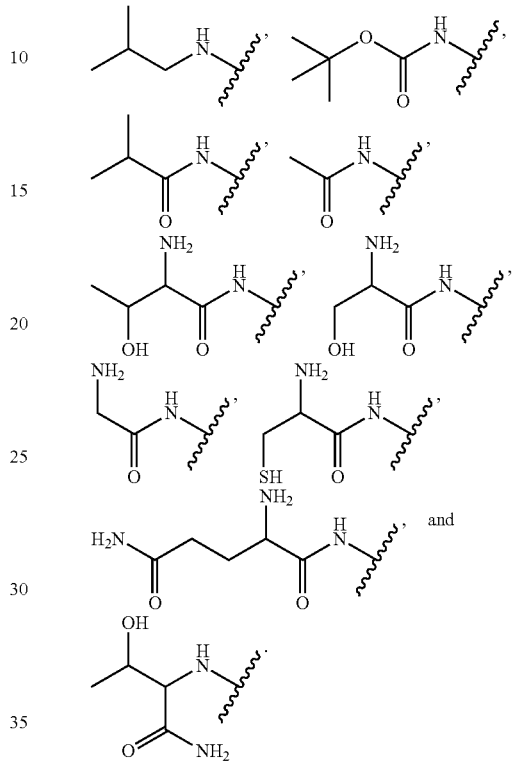

In some embodiments, $R^{5b}$ is H; and $R^{5a}$ is selected from the group consisting of hydroxyl, halogen, methyl, —O—$CH_2$-Ph, —$NH_2$,

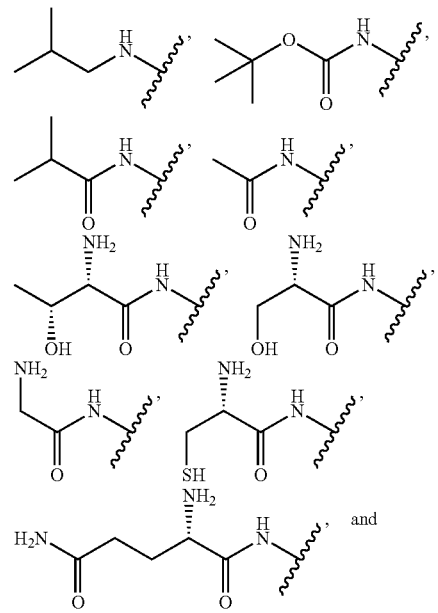

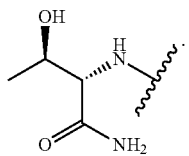

In some embodiments, $R^{5a}$ is selected from the group consisting of H, hydroxyl, halogen, —$C_1$-$C_4$alkoxy-phenyl, —$C_1$-$C_4$alkyl, —$NR^a$—C(O)—$C_1$-$C_4$alkyl, —$NR^a$—C(O)—O—$C_1$-$C_4$alkyl, —$NR^aR^b$, and —$NR^aCH(R^{10})$—C(O)—$R^{11}$, where $C_1$-$C_4$alkyl is optionally substituted by one or two substituents each independently selected from —C(O)NH$_2$, —$NR^aR^b$, —SH, —C(O)—$C_1$-$C_4$alkyl, —C(O)—O—$C_1$-$C_4$alkyl, —O—C(O)—$C_1$-$C_4$alkyl, hydroxyl, and halogen; $R^{10}$ is selected from the group consisting of H and $C_1$-$C_4$alkyl, wherein $C_1$-$C_4$alkyl is optionally substituted by one or two substituents each independently selected from —C(O)$NR^aR^b$, —$NR^a$—C(O)—$C_1$-$C_4$alkyl, —$NR^aR^b$, —SH, —C(O)—$C_1$-$C_4$alkyl, —C(O)—O—$C_1$-$C_4$alkyl, —O—C(O)—$C_1$-$C_4$alkyl, —$C_1$-$C_4$alkoxy, hydroxyl, and halogen; $R^{11}$ is selected from the group consisting of hydroxyl, —$C_1$-$C_4$alkoxy, and —$NR^aR^b$; $R^{5b}$ is H; and $R^1$ is H.

In some embodiments, $R^{5a}$ is selected from the group consisting of hydroxyl, halogen, methyl, —O—CH$_2$-Ph, NH$_2$,

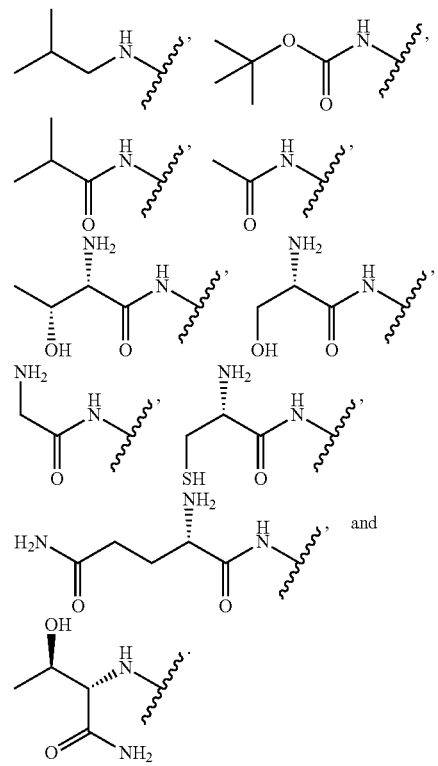

In some embodiments, $R^{5a}$ is selected from the group consisting of hydroxyl, halogen, methyl, —O—CH$_2$-Ph, NH$_2$, In certain embodiments, $R^1$ and/or $R^{5a}$ independently can be an amino acid or a derivative of an amino acid, for example, an alpha "amino amide" represented by H$_2$N—CH(amino acid side chain)-C(O)NH$_2$. In certain embodiments, the nitrogen atom of the amino group of the amino acid or the amino acid derivative is a ring nitrogen in a chemical formula described herein. In such embodiments, the carboxylic acid of the amino acid or the amide group of an amino amide (amino acid derivative) is not within the ring structure, i.e., not a ring atom. In certain embodiments, the carboxylic acid group of the amino acid or the amino acid derivative forms an amide bond with a ring nitrogen in a chemical formula disclosed herein, thereby providing an amino amide, where the amino group of the amino amide is not within the ring structure, i.e., not a ring atom. In various embodiments, the amino acid or the derivative of an amino acid can be bonded to a ring carbon via its amino group, amide group, carboxylic acid group, or its methylene or higher order alkylene group, as appropriate and understood by a skilled artisan. In certain embodiments, $R^1$ and/or $R^{5a}$ independently can be an alpha amino acid, an alpha amino acid derivative, and/or another amino acid or amino acid derivative such as a beta amino acid or a beta amino acid derivative, for example, a beta amino amide.

Disclosed compounds can include a compound having the formula:

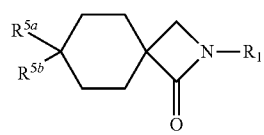

or a stereoisomer and/or a pharmaceutically acceptable salt thereof, where:

$R^1$ is selected from the group consisting of H, —$C_1$-$C_4$alkyl, —$C_1$-$C_4$alkyl-phenyl, and —CH($R^8$)—C(O)—$R^9$; wherein phenyl is optionally substituted by one, two or three substituents each independently selected from —$C_1$-$C_4$alkyl, $C_1$-$C_4$alkoxy, hydroxyl, and halogen; and $R^{5a}$ is selected from the group consisting of H, hydroxyl, halogen, cyano, —$C_1$-$C_4$alkoxy, —O—$C_1$-$C_4$ alkyl-phenyl, —$C_1$-$C_4$alkyl, —C(O)—$C_1$-$C_4$alkyl, —$NR^a$—C(O)—$C_1$-$C_4$alkyl, —$NR^a$—C(O)—O—$C_1$-$C_4$alkyl, —$NR^aR^b$, and —$NR^a$CH($R^{10}$)—C(O)—$R^{11}$; wherein $C_1$-$C_4$alkyl is optionally substituted by one, two or three substituents each independently selected from —COOH, —C(O)$NH_2$, —$NR^aR^b$, —SH, —C(O)—$C_1$-$C_4$alkyl, —C(O)—O—$C_1$-$C_4$alkyl, —O—C(O)—$C_1$-$C_4$alkyl, —$C_1$-$C_4$alkoxy, hydroxyl, and halogen; and phenyl is optionally substituted by one, two or three substituents each independently selected from —$C_1$-$C_4$alkyl, —$C_1$-$C_4$haloalkyl, —$C_1$-$C_4$alkoxy, —$NR^aR^b$, hydroxyl, and halogen;

$R^{5b}$ is selected from the group consisting of H, halogen, —$C_1$-$C_4$alkyl, and —$C_1$-$C_4$haloalkyl; or $R^{5a}$ and $R^{5b}$ taken together form an oxo group;

$R^8$ and $R^{10}$ are selected independently from the group consisting of H and —$C_1$-$C_4$alkyl, wherein $C_1$-$C_4$alkyl is optionally substituted by one, two or three substituents each independently selected from —C(O)$NR^aR^b$, —$NR^a$—C(O)—$C_1$-$C_4$alkyl, —$NR^aR^b$, —SH, —C(O)—$C_1$-$C_4$alkyl, —C(O)—O—$C_1$-$C_4$alkyl, —O—C(O)—$C_1$-$C_4$alkyl, $C_1$-$C_4$alkoxy, —COOH, hydroxyl, and halogen;

$R^9$ and $R^{11}$ are independently selected from the group consisting of hydroxyl, $C_1$-$C_4$alkoxy, and —$NR^aR^b$; and $R^a$ and $R^b$ are each independently selected for each occurrence from the group consisting of H, —$C_1$-$C_4$alkyl, —$C_1$-$C_4$alkyl-phenyl, —$C_1$-$C_4$alkyl-$C_3$-$C_7$cycloalkyl, —$C_1$-$C_4$alkyl-heterocycloalkyl, and —$C_1$-$C_4$alkyl-heteroaryl, wherein heterocycloalkyl and heteroaryl include 1, 2, or 3 ring atoms independently selected from N, O and S, and phenyl is optionally substituted by one, two or three substituents selected from halogen, hydroxyl, —C(O)$NH_2$, —C(O)NH($C_1$-$C_4$alkyl), —C(O)N($C_1$-$C_4$alkyl)$_2$, —$C_1$-$C_3$alkyl and —$C_1$-$C_3$alkoxy; or $R^a$ and $R^b$ taken together with the nitrogen to which they are attached form a 4-6-membered heterocycloalkyl or a 5-8-membered heteroaryl.

In some embodiments, $R^1$ is H or —CH($R^8$)—C(O)—$R^9$; $R^8$ is selected from the group consisting of H and —$C_1$-$C_4$alkyl, where $C_1$-$C_4$alkyl is optionally substituted by one or two substituents each independently selected from —C(O)$NH_2$, —$NH_2$, —SH, —O—C(O)—$C_1$-$C_4$alkyl, —$C_1$-$C_4$alkoxy, and hydroxyl; and $R^9$ is selected independently from the group consisting of hydroxyl, —$C_1$-$C_4$alkoxy, and —$NR^aR^b$.

In some embodiments, $R^8$ is selected from the group consisting of H, methyl,

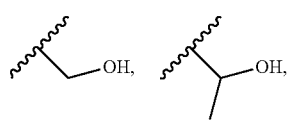

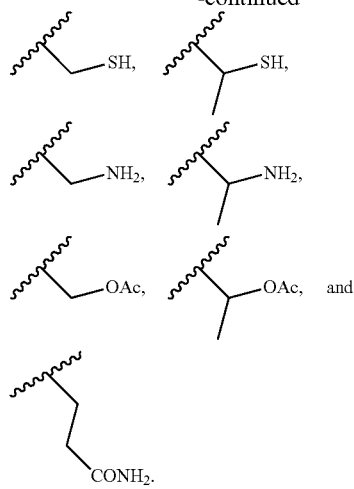

In some embodiments, $R^1$ is H.

In some embodiments, $R^{5a}$ is selected from the group consisting of H, hydroxyl, halogen, methyl, —O—$CH_2$-Ph, —$NH_2$, —NH—$C_1$-$C_4$alkyl, —NH—C(O)—$C_1$-$C_4$alkyl, —NH—C(O)—O—$C_1$-$C_4$alkyl, and —$NR^a$CH($R^{10}$)—C(O)—$R^{11}$; where $C_1$-$C_4$alkyl is optionally substituted by one or two substituents each independently selected from —C(O)$NH_2$, —$NH_2$, —SH, —OC(O)$CH_3$, hydroxyl, and halogen; and $R^{5b}$ is H or halogen.

In some embodiments, $R^{5b}$ is H or halogen; and $R^{5a}$ is selected from the group consisting of H, hydroxyl, halogen, methyl, —O—$CH_2$-Ph, —$NH_2$,

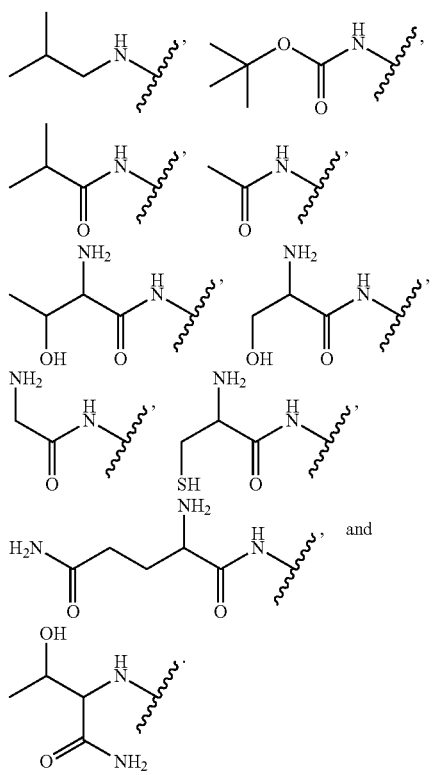

In some embodiments, $R^{5b}$ is H or halogen; and $R^{5a}$ is selected from the group consisting of hydroxyl, halogen, methyl, —O—CH$_2$-Ph, —NH$_2$,

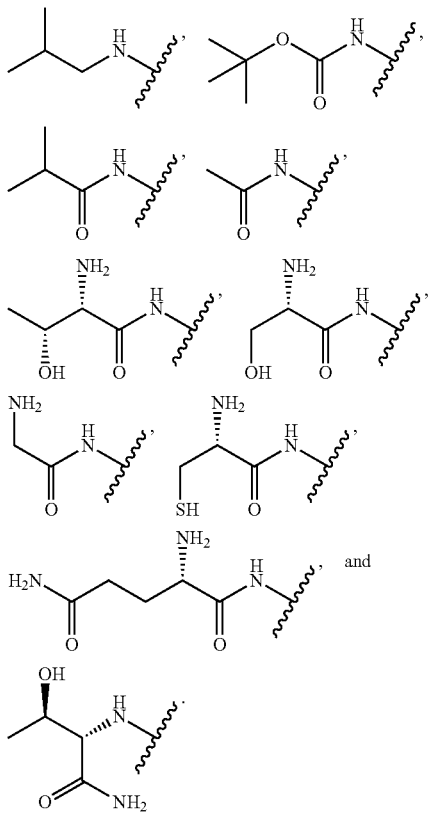

In some embodiments, $R^1$ is H; $R^{5b}$ is H; and $R^{5a}$ is selected from the group consisting of

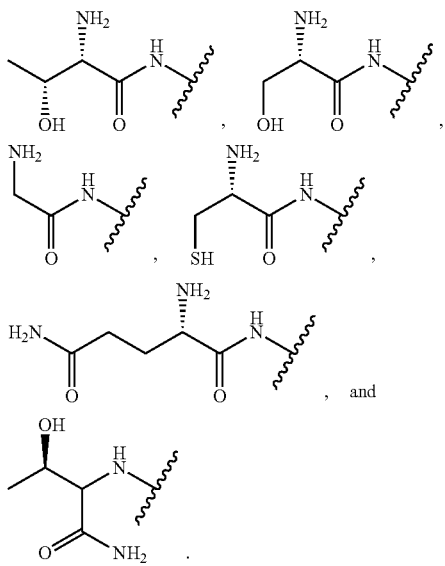

Disclosed compounds can include a compound having the formula:

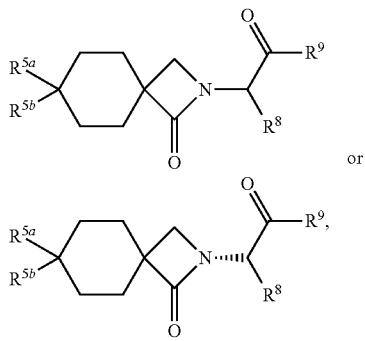

or a stereoisomer and/or a pharmaceutically acceptable salt thereof, where:

$R^1$ is selected from the group consisting of H, —C$_1$-C$_4$alkyl, —C$_1$-C$_4$alkyl-phenyl, and —CH(R$^8$)—C(O)—R$^9$; wherein phenyl is optionally substituted by one, two or three substituents each independently selected from —C$_1$-C$_4$alkyl, C$_1$-C$_4$alkoxy, hydroxyl, and halogen; and $R^{5a}$ is selected from the group consisting of H, hydroxyl, halogen, cyano, —C$_1$-C$_4$alkoxy, —O—C$_1$-C$_4$ alkyl-phenyl, —C$_1$-C$_4$alkyl, —C(O)—C$_1$-C$_4$alkyl, —NR$^a$—C(O)—C$_1$-C$_4$alkyl, —NR$^a$—C(O)—O—C$_1$-C$_4$alkyl, —NR$^a$R$^b$, and —NR$^a$CH(R$^{10}$)—C(O)—R$^{11}$; wherein C$_1$-C$_4$alkyl is optionally substituted by one, two or three substituents each independently selected from —COOH, —C(O)NH$_2$, —NR$^a$R$^b$, —SH, —C(O)—C$_1$-C$_4$alkyl, —C(O)—O—C$_1$-C$_4$alkyl, —O—C(O)—C$_1$-C$_4$alkyl, —C$_1$-C$_4$alkoxy, hydroxyl, and halogen; and phenyl is optionally substituted by one, two or three substituents each independently selected from —C$_1$-C$_4$alkyl, —C$_1$-C$_4$haloalkyl, —C$_1$-C$_4$alkoxy, —NR$^a$R$^b$, hydroxyl, and halogen; $R^{5b}$ is selected from the group consisting of H, halogen, —C$_1$-C$_4$alkyl, and —C$_1$-C$_4$haloalkyl; or $R^{5a}$ and $R^{5b}$ taken together form an oxo group;

$R^8$ and $R^{10}$ are selected independently from the group consisting of H and —C$_1$-C$_4$alkyl, wherein C$_1$-C$_4$alkyl is optionally substituted by one, two or three substituents each independently selected from —C(O)NR$^a$R$^b$, —NR$^a$—C(O)—C$_1$-C$_4$alkyl, —NR$^a$R$^b$, —SH, —C(O)—C$_1$-C$_4$alkyl, —C(O)—O—C$_1$-C$_4$alkyl, —O—C(O)—C$_1$-C$_4$alkyl, C$_1$-C$_4$alkoxy, —COOH, hydroxyl, and halogen;

$R^9$ and $R^{11}$ are selected independently from the group consisting of hydroxyl, C$_1$-C$_4$alkoxy, and —NR$^a$R$^b$; and $R^a$ and $R^b$ are each independently selected for each occurrence from the group consisting of H, —C$_1$-C$_4$alkyl, —C$_1$-C$_4$alkyl-phenyl, —C$_1$-C$_4$alkyl-C$_3$-C$_7$cycloalkyl, —C$_1$-C$_4$alkyl-heterocycloalkyl, and —C$_1$-C$_4$alkyl-heteroaryl, wherein heterocycloalkyl and heteroaryl include 1, 2, or 3 ring atoms independently selected from N, O and S, and phenyl is optionally substituted by one, two or three substituents selected from halogen, hydroxyl, —C(O)NH$_2$, —C(O)NH(C$_1$-C$_4$alkyl), —C(O)N(C$_1$-C$_4$alkyl)$_2$, —C$_1$-C$_3$alkyl and —C$_1$-C$_3$alkoxy; or $R^a$ and $R^b$ taken together with the nitrogen to which they are attached form a 4-6-membered heterocycloalkyl or a 5-8-membered heteroaryl.

In some embodiments, $R^{5a}$ is selected from the group consisting of H, hydroxyl, halogen, methyl, —O—CH$_2$-Ph, —NH$_2$, —NH—C$_1$-C$_4$alkyl, —NH—C(O)—C$_1$-C$_4$alkyl, and —NH—C(O)—O—C$_1$-C$_4$alkyl; wherein C$_1$-C$_4$alkyl is optionally substituted by one or two substituents each independently selected from —C(O)NH$_2$, —NH$_2$, —SH, —OC(O)CH$_3$, hydroxyl, and halogen.

In some embodiments, $R^{5a}$ is selected from the group consisting of H, hydroxyl, halogen, methyl, —O—CH$_2$-Ph, —NH$_2$,

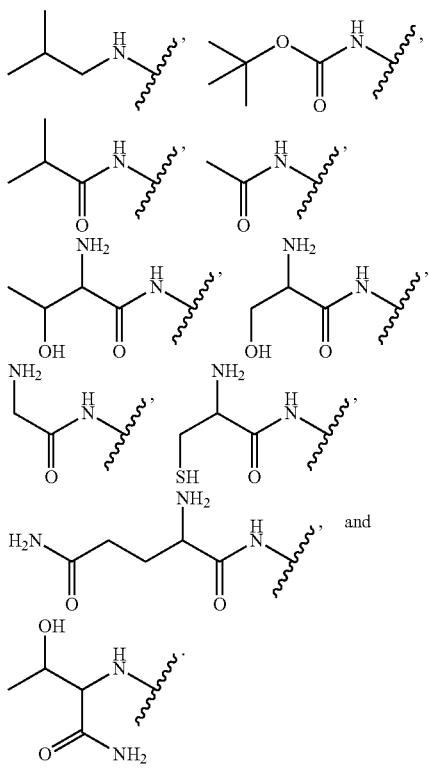

In some embodiments, $R^{5b}$ is H or halogen; and $R^{5a}$ is selected from the group consisting of H, hydroxyl, halogen, methyl, —O—CH$_2$-Ph, —NH$_2$,

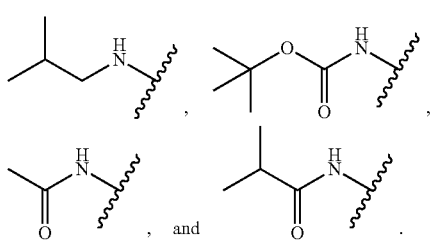

In some embodiments, $R^8$ is selected from the group consisting of H, methyl,

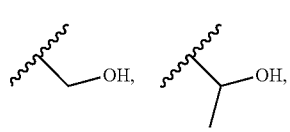

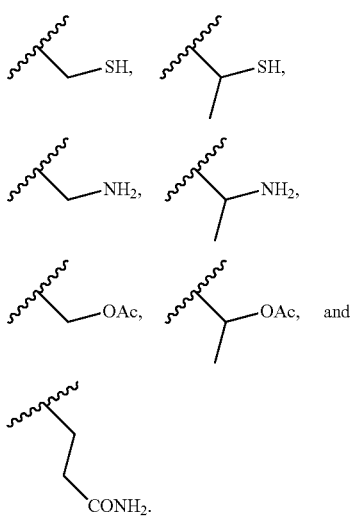

In some embodiments, $R^9$ is —NH$_2$.

In some embodiments, a disclosed compound is selected from the compounds delineated in the Examples or in Table 1, and includes pharmaceutically acceptable salts and/or stereoisomers thereof.

In some embodiments, a disclosed compound is selected from the group consisting of:

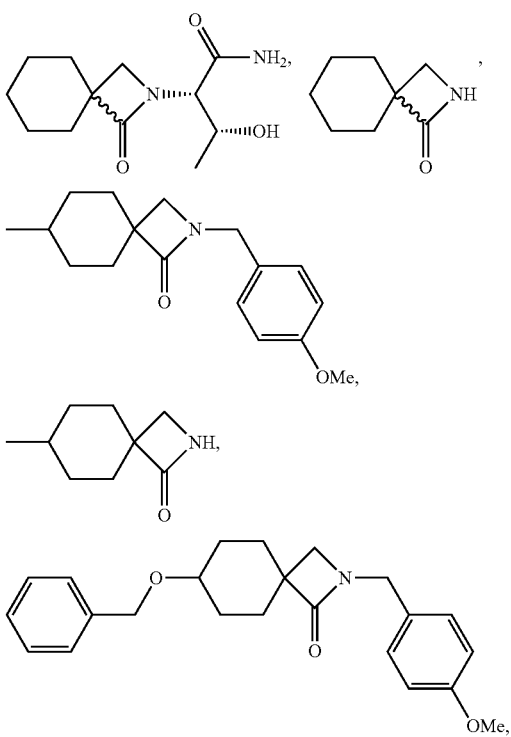

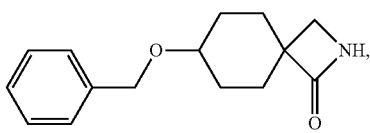

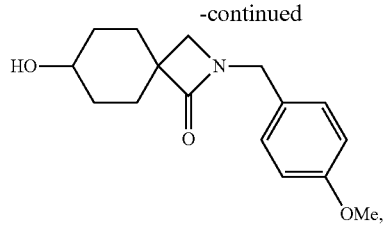
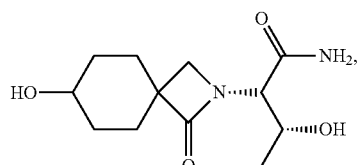
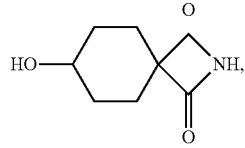
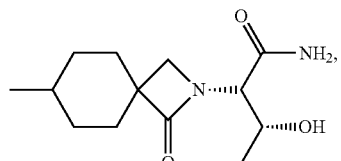
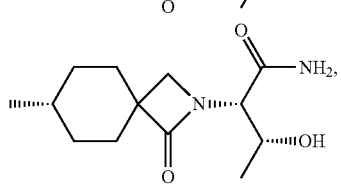
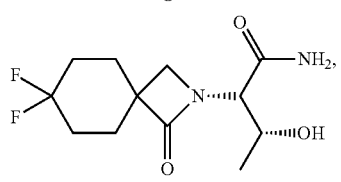
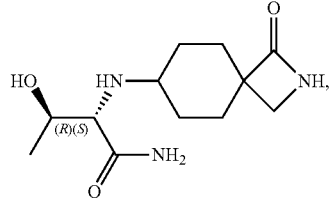
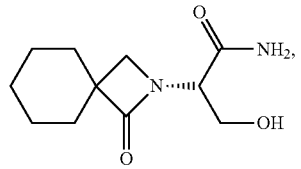
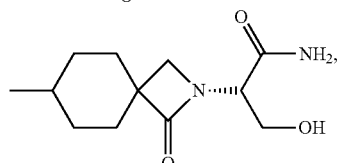
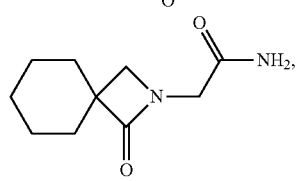
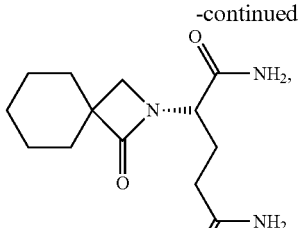
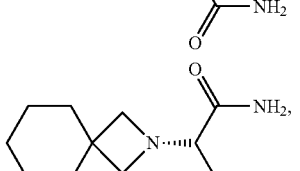
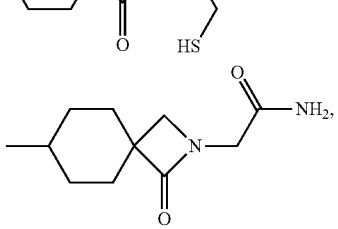
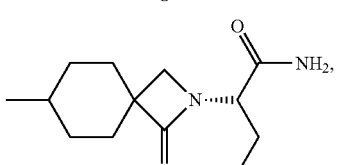
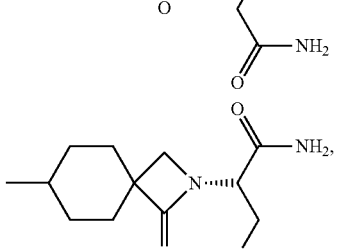
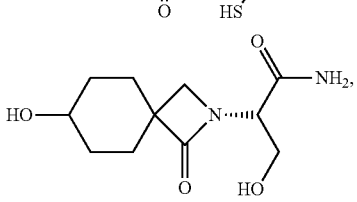
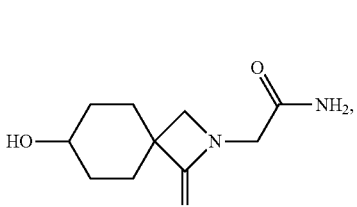
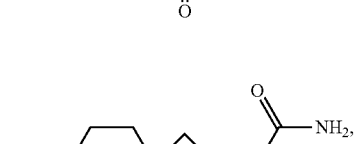
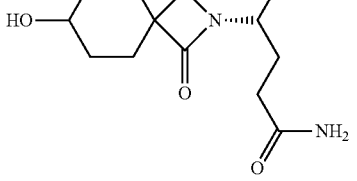

-continued
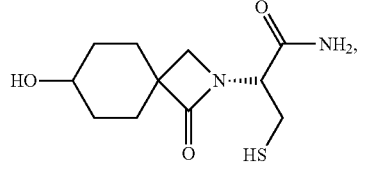
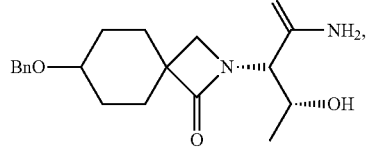
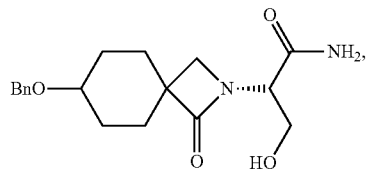
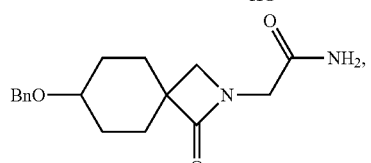
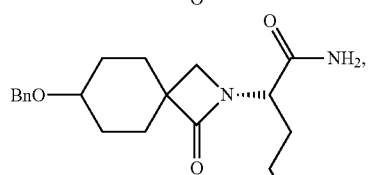
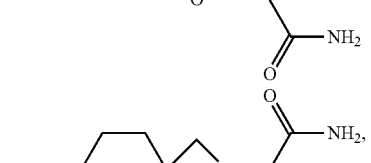
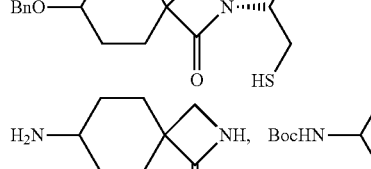
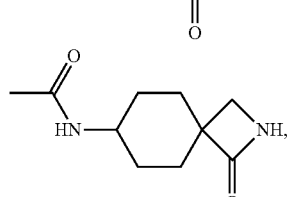
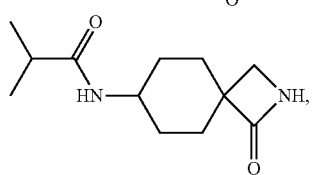
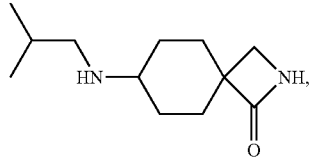
-continued
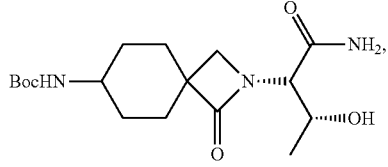
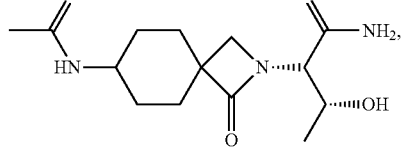
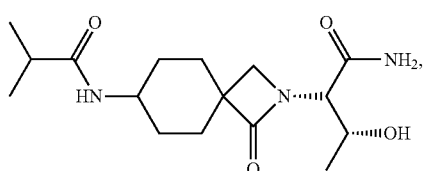
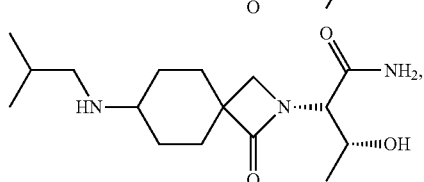
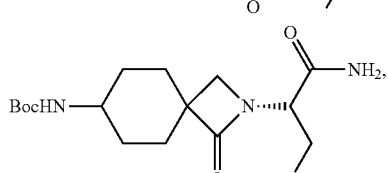
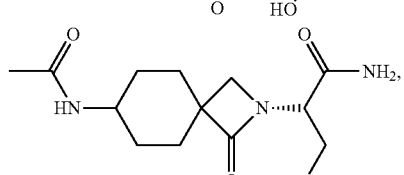
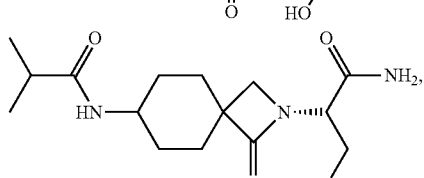
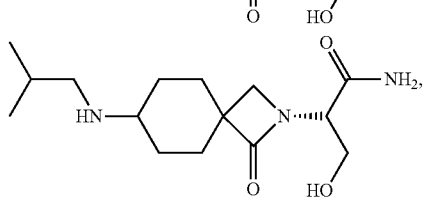
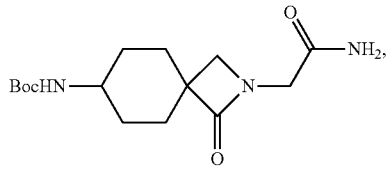
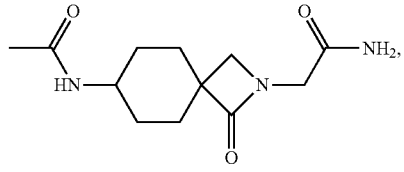

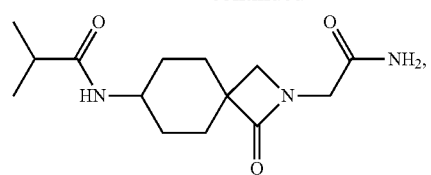
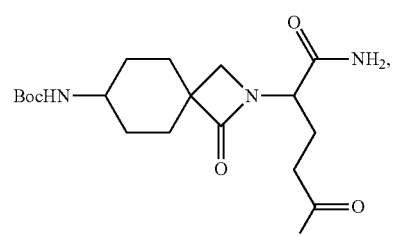
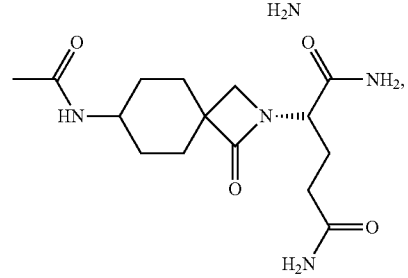
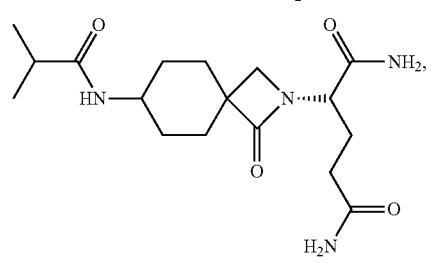
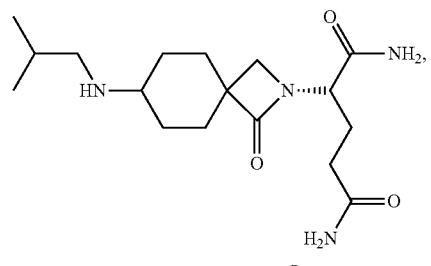
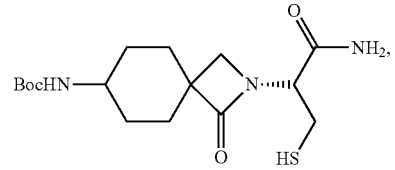
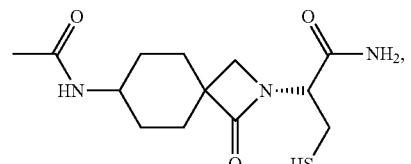
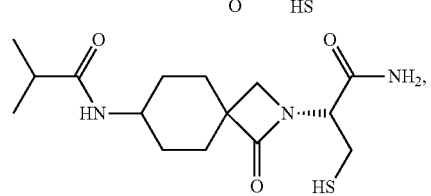
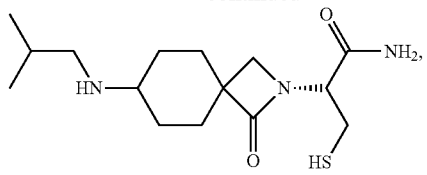
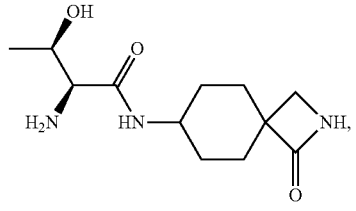
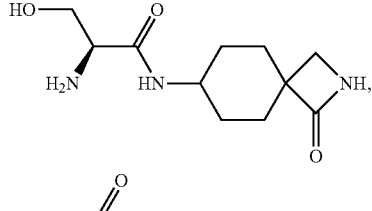
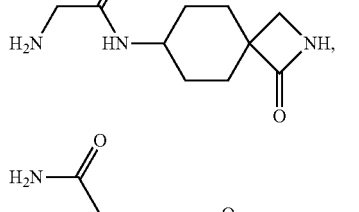
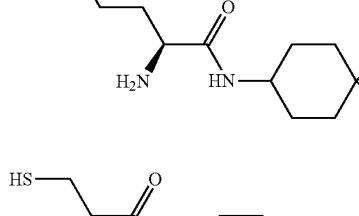
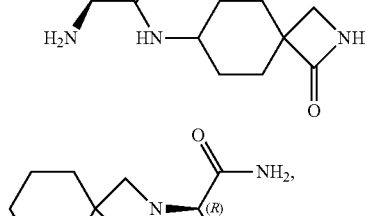
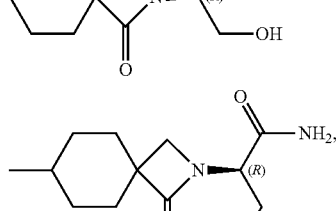
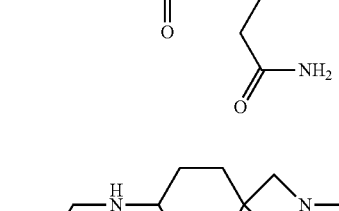
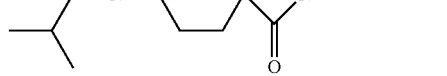

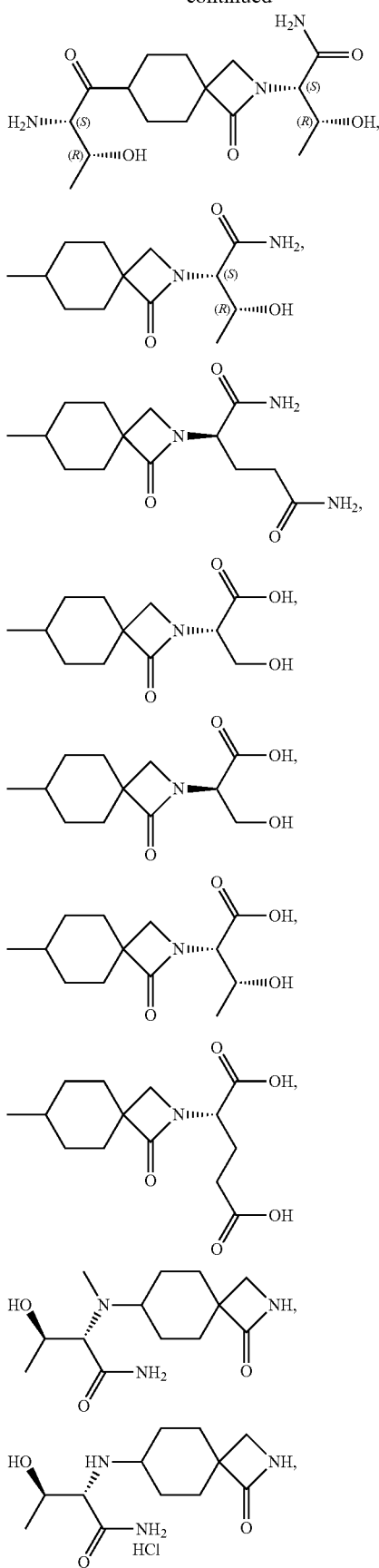

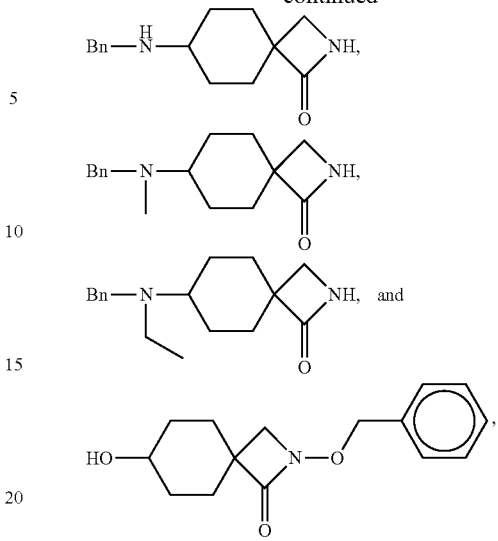

or a stereoisomer and/or a pharmaceutically acceptable salt thereof.

The compounds of the present disclosure and formulations thereof may have a plurality of chiral centers. Each chiral center may be independently R, S, or any mixture of R and S. For example, in some embodiments, a chiral center may have an R:S ratio of between about 100:0 and about 50:50 ("racemate"), between about 100:0 and about 75:25, between about 100:0 and about 85:15, between about 100:0 and about 90:10, between about 100:0 and about 95:5, between about 100:0 and about 98:2, between about 100:0 and about 99:1, between about 0:100 and 50:50, between about 0:100 and about 25:75, between about 0:100 and about 15:85, between about 0:100 and about 10:90, between about 0:100 and about 5:95, between about 0:100 and about 2:98, between about 0:100 and about 1:99, between about 75:25 and 25:75, and about 50:50. Formulations of the disclosed compounds comprising a greater ratio of one or more isomers (i.e., R and/or S) may possess enhanced therapeutic characteristic relative to racemic formulations of a disclosed compounds or mixture of compounds. In some instances, chemical formulas contain the descriptor "—(R)—" or "—(S)—" that is further attached to solid wedge or dashed wedge. This descriptor is intended to show a methine carbon (CH) that is attached to three other substituents and has either the indicated R or S configuration.

Disclosed compounds may provide for efficient cation channel opening at the NMDA receptor, e.g. may bind or associate with the glutamate site or glycine site or other modularity site of the NMDA receptor to assist in opening the cation channel. The disclosed compounds may be used to regulate (turn on or turn off) the NMDA receptor through action as an agonist or antagonist.

The compounds described herein, in some embodiments, may bind to a specific NMDA receptor subtypes. For example, a disclosed compound may bind to one NMDA subtype and not another. In another embodiment, a disclosed compound may bind to one, or more than one NMDA subtype, and/or may have substantially less (or substantial no) binding activity to certain other NMDA subtypes.

The compounds as described herein may bind to NMDA receptors. A disclosed compound may bind to the NMDA receptor resulting in agonist-like activity (facilitation) over a certain dosing range and/or may bind to the NMDA receptor resulting in antagonist-like activity (inhibition) over a certain dosing range. In some embodiments, a disclosed compound may possess a potency that is 10-fold or greater than the activity of existing NMDA receptor modulators.

The disclosed compounds may exhibit a high therapeutic index. The therapeutic index, as used herein, refers to the ratio of the dose that produces a toxicity in 50% of the population (i.e., $TD_{50}$) to the minimum effective dose for 50% of the population (i.e., $ED_{50}$). Thus, the therapeutic index=$(TD_{50}):(ED_{50})$. In some embodiments, a disclosed compound may have a therapeutic index of at least about 10:1, at least about 50:1, at least about 100:1, at least about 200:1, at least about 500:1, or at least about 1000:1.

Compositions

In other aspects, a pharmaceutical formulation or a pharmaceutical composition including a disclosed compound and optionally a pharmaceutically acceptable excipient are provided. In some embodiments, a pharmaceutical composition includes a racemic mixture or a varied stereoisomeric mixture of one or more of the disclosed compounds.

A formulation can be prepared in any of a variety of forms for use such as for administering an active agent to a patient, who may be in need thereof, as are known in the pharmaceutical arts. For example, the pharmaceutical compositions of the present disclosure can be formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, and pastes for application to the tongue; (2) parenteral administration by, for example, subcutaneous, intramuscular, intraperitoneal, intravenous or epidural injection as, for example, a sterile solution or suspension, or sustained-release formulation; (3) topical administration, for example, as a cream, ointment, or a controlled-release patch or spray applied to the skin; (4) intravaginal or intrarectal administration, for example, as a pessary, cream or foam; (5) sublingual administration; (6) ocular administration; (7) transdermal administration; or (8) nasal administration.

For example, pharmaceutical compositions of the disclosure can be suitable for delivery to the eye, i.e., ocularly. Related methods can include administering a pharmaceutically effective amount of a disclosed compound or a pharmaceutical composition including a disclosed compound to a patient in need thereof, for example, to an eye of the patient, where administering can be topically, subconjunctivally, subtenonly, intravitreally, retrobulbarly, peribulbarly, intracomerally, and/or systemically.

Amounts of a disclosed compound as described herein in a formulation may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier.

The specification for the dosage unit forms are dictated by and directly dependent on (a) the unique characteristics of the compound selected and the particular therapeutic effect to be achieved, and (b) the limitations inherent in the art of compounding such an active compound for the treatment of sensitivity in individuals.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin.

The compounds can be administered in a time release formulation, for example in a composition which includes a slow release polymer. The compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are generally known to those skilled in the art.

Sterile injectable solutions can be prepared by incorporating the compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In accordance with an alternative aspect, a compound may be formulated with one or more additional compounds that enhance the solubility of the compound.

Methods for treating a condition in a patient in need thereof by administering a therapeutically effective dose of a compound described herein are provided. In some embodiments, the condition may be a mental condition. For example, a mental illness may be treated. In another aspect, a nervous system condition may be treated. For example, a condition that affects the central nervous system, the peripheral nervous system, and/or the eye may be treated. In some embodiments, neurodegenerative diseases may be treated.

In some embodiments, the methods include administering a compound to treat patients suffering from autism, anxiety, depression, bipolar disorder, attention deficit disorder, attention deficit hyperactivity disorder (ADHD), schizophrenia, a psychotic disorder, a psychotic symptom, social withdrawal, obsessive-compulsive disorder (OCD), phobia, post-traumatic stress syndrome, a behavior disorder, an impulse control disorder, a substance abuse disorder (e.g., a withdrawal symptom, opiate addiction, nicotine addiction, and ethanol addition), a sleep disorder, a memory disorder (e.g., a deficit, loss, or reduced ability to make new memories), a learning disorder, urinary incontinence, multiple system atrophy, progressive supra-nuclear palsy, Friedrich's ataxia, Down's syndrome, fragile X syndrome, tuberous sclerosis, olivio-ponto-cerebellar atrophy, cerebral palsy, drug-induced optic neuritis, ischemic retinopathy, diabetic retinopathy, glaucoma, dementia, AIDS dementia, Alzheimer's disease, Huntington's chorea, spasticity, myoclonus, muscle spasm, infantile spasm, Tourette's syndrome, epilepsy, cerebral ischemia, stroke, a brain tumor, traumatic brain injury, cardiac arrest, myelopathy, spinal cord injury, peripheral neuropathy, acute neuropathic pain, and chronic neuropathic pain.

In some embodiments, methods of treating a memory disorder associated with aging, schizophrenia, special learning disorders, seizures, post-stroke convulsions, brain ischemia, hypoglycemia, cardiac arrest, epilepsy, Lewy body dementia, migraine, AIDS dementia, Huntington's chorea, Parkinson's disease, early stage Alzheimer's disease, and Alzheimer's disease are provided.

In certain embodiments, methods for treating schizophrenia are provided. For example, paranoid type schizophrenia, disorganized type schizophrenia (i.e., hebephrenic schizophrenia), catatonic type schizophrenia, undifferentiated type schizophrenia, residual type schizophrenia, post-schizophrenic depression, and simple schizophrenia may be treated using the methods and compositions disclosed herein. Psychotic disorders such as schizoaffective disorders, delusional disorders, brief psychotic disorders, shared psychotic disorders, and psychotic disorders with delusions or hallucinations may also be treated using the compounds and compositions disclosed herein.

Paranoid schizophrenia may be characterized where delusions or auditory hallucinations are present, but thought disorder, disorganized behavior, or affective flattening are not. Delusions may be persecutory and/or grandiose, but in addition to these, other themes such as jealousy, religiosity, or somatization may also be present. Disorganized type schizophrenia may be characterized where thought disorder and flat affect are present together. Catatonic type schizophrenia may be characterized where the patient may be almost immobile or exhibit agitated, purposeless movement. Symptoms can include catatonic stupor and waxy flexibility. Undifferentiated type schizophrenia may be characterized where psychotic symptoms are present but the criteria for paranoid, disorganized, or catatonic types have not been met. Residual type schizophrenia may be characterized where positive symptoms are present at a low intensity only. Post-schizophrenic depression may be characterized where a depressive episode arises in the aftermath of a schizophrenic illness where some low-level schizophrenic symptoms may still be present. Simple schizophrenia may be characterized by insidious and progressive development of prominent negative symptoms with no history of psychotic episodes.

In some embodiments, methods are provided for treating psychotic symptoms that may be present in other mental disorders, including, but not limited to, bipolar disorder, borderline personality disorder, drug intoxication, and drug-induced psychosis. In various embodiment, methods for treating delusions (e.g., "non-bizarre") that may be present in, for example, delusional disorder are provided.

In various embodiments, methods for treating social withdrawal in conditions including, but not limited to, social anxiety disorder, avoidant personality disorder, and schizotypal personality disorder are provided.

In some embodiments, the disclosure provides methods for treating a neurodevelopmental disorder related to synaptic dysfunction in a patient in need thereof, where the methods generally include administering to the patient a therapeutically effective amount of a disclosed compound, or a pharmaceutical composition including a disclosed compound. In certain embodiments, the neurodevelopmental disorder related to synaptic dysfunction can be Rett syndrome also known as cerebroatrophic hyperammonemia, MECP2 duplication syndrome (e.g., a MECP2 disorder), CDKL5 syndrome, fragile X syndrome (e.g., a FMR1 disorder), tuberous sclerosis (e.g., a TSC1 disorder and/or a TSC2 disorder), neurofibromatosis (e.g., a NF1 disorder), Angelman syndrome (e.g., a UBE3A disorder), the PTEN hamartoma tumor syndrome, Phelan-McDermid syndrome (e.g., a SHANK3 disorder), or infantile spasms. In particular embodiments, the neurodevelopmental disorder can be caused by mutations in the neuroligin (e.g., a NLGN3 disorder and/or a NLGN2 disorder) and/or the neurexin (e.g., a NRXN1 disorder).

In some embodiments, methods are provided for treating neuropathic pain. The neuropathic pain can be acute or chronic. In some cases, the neuropathic pain can be associated with a condition such as herpes, HIV, traumatic nerve injury, stroke, post-ischemia, chronic back pain, post-herpetic neuralgia, fibromyalgia, reflex sympathetic dystrophy, complex regional pain syndrome, spinal cord injury, sciatica, phantom limb pain, diabetic neuropathy such as diabetic peripheral neuropathy ("DPN"), and cancer chemotherapeutic-induced neuropathic pain. In certain embodiments, methods for enhancing pain relief and for providing analgesia to a patient are also provided.

In various embodiments, methods of the disclosure include a method of treating autism and/or an autism spectrum disorder in a patient need thereof, comprising administering an effective amount of a compound to the patient. In some embodiments, a method for reducing the symptoms of autism in a patient in need thereof is provided, the method comprising administering an effective amount of a disclosed compound to the patient. For example, upon administration, the compound may decrease the incidence of one or more symptoms of autism such as eye contact avoidance, failure to socialize, attention deficit, poor mood, hyperactivity, abnormal sound sensitivity, inappropriate speech, disrupted sleep, and perseveration. Such decreased incidence may be measured relative to the incidence in the untreated individual or an untreated individual(s).

Also provided herein is a method of modulating an autism target gene expression in a cell comprising contacting a cell with an effective amount of a compound described herein. The autism gene expression may be for example, selected from ABAT, APOE, CHRNA4, GABRA5, GFAP, GRIN2A, PDYN, and PENK. In certain embodiments, a method of modulating synaptic plasticity in a patient suffering from a synaptic plasticity related disorder is provided, comprising administering to the patient an effective amount of a compound.

In some embodiments, a method of treating Alzheimer's disease, or e.g., treatment of memory loss that e.g., accompanies early stage Alzheimer's disease, in a patient in need thereof is provided, comprising administering a compound. Also provided herein is a method of modulating an Alzheimer's amyloid protein (e.g., beta amyloid peptide, e.g. the isoform $A\beta_{1-42}$), in-vitro or in-vivo (e.g. in a cell) comprising contacting the protein with an effective amount of a compound is disclosed. For example, in some embodiments, a compound may block the ability of such amyloid protein to inhibit long-term potentiation in hippocampal slices as well as apoptotic neuronal cell death. In some embodiments, a disclosed compound may provide neuroprotective properties to a Alzheimer's patient in need thereof, for example, may provide a therapeutic effect on later stage Alzheimer's-associated neuronal cell death.

In certain embodiments, the disclosed methods include treating a psychosis or a pseudobulbar affect ("PBA") that is induced by another condition such as a stroke, amyotrophic lateral sclerosis (ALS or Lou Gehrig's disease), multiple sclerosis, traumatic brain injury, Alzheimer's disease, dementia, and/or Parkinson's disease. Such methods, as with other methods of the disclosure, include administration of a pharmaceutically effective amount of a disclosed compound to a patient in need thereof.

In some embodiments, a method of treating depression comprising administering a compound described herein is provided. In some embodiments, the treatment may relieve depression or a symptom of depression without affecting behavior or motor coordination and without inducing or promoting seizure activity. Exemplary depression conditions that are expected to be treated according to this aspect include, but are not limited to, major depressive disorder, dysthymic disorder, psychotic depression, postpartum depression, premenstrual syndrome, premenstrual dysphoric disorder, seasonal affective disorder (SAD), bipolar disorder (or manic depressive disorder), mood disorder, and depressions caused by chronic medical conditions such as cancer or chronic pain, chemotherapy, chronic stress, and post traumatic stress disorders. In addition, patients suffering from any form of depression often experience anxiety. Various symptoms associated with anxiety include fear, panic, heart palpitations, shortness of breath, fatigue, nausea, and headaches among others. Anxiety or any of the symptoms thereof may be treated by administering a compound as described herein.

Also provided herein are methods of treating a condition in treatment-resistant patients, e.g., patients suffering from a mental or central nervous system condition that does not, and/or has not, responded to adequate courses of at least one, or at least two, other compounds or therapeutics. For example, provided herein is a method of treating depression in a treatment resistant patient, comprising a) optionally identifying the patient as treatment resistant and b) administering an effective dose of a compound to said patient.

In some embodiments, a compound described herein may be used for acute care of a patient. For example, a compound may be administered to a patient to treat a particular episode (e.g., a severe episode) of a condition disclosed herein.

Also provided herein are combination therapies comprising a compound in combination with one or more other active agents. For example, a compound may be combined with one or more antidepressants, such as tricyclic antidepressants, MAO-I's, SSRI's, and double and triple uptake inhibitors and/or anxiolytic drugs. Exemplary drugs that may be used in combination with a compound include Anafranil, Adapin, Aventyl, Elavil, Norpramin, Pamelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), and Ludiomill. In another example, a compound may be combined with an antipsychotic medication. Non-limiting examples of antipsychotics include butyrophenones, phenothiazines, thioxanthenes, clozapine, olanzapine, risperidone, quetiapine, ziprasidone, amisulpride, asenapine, paliperidone, iloperidone, zotepine, sertindole, lurasidone, and aripiprazole. It should be understood that combinations of a compound and one or more of the above therapeutics may be used for treatment of any suitable condition and are not limited to use as antidepressants or antipsychotics.

EXAMPLES

The following examples are provided for illustrative purposes only and are not intended to limit the scope of the present disclosure.

The following abbreviations may be used herein and have the indicated definitions: Ac is acetyl (—C(O)CH$_3$), AIDS is acquired immune deficiency syndrome, Boc and BOC are tert-butoxycarbonyl, Boc$_2$O is di-tert-butyl dicarbonate, Bn is benzyl, BOM-Cl is benzyloxymethyl chloride, CAN is ceric ammonium nitrate, Cbz is carboxybenzyl, DCM is dichloromethane, DIAD is diisopropyl azodicarboxylate, DIPEA is N,N-diisopropylethylamine, DMAP is 4-dimethylaminopyridine, DMF is N,N-dimethylformamide, DMSO is dimethyl sulfoxide, EDC and EDCI are 1-ethyl-3-(3-dimethylaminopropyl)carbodiimide hydrochloride, ESI is electrospray ionization, EtOAc is ethyl acetate, Gly is glycine, h is hour, HATU is 2-(7-aza-1H-benzotriazole-1-yl)-1,1,3,3-tetramethyluronium hexafluorophosphate, HIV is human immunodeficiency virus, HPLC is high performance liquid chromatography, LCMS is liquid chromatography/mass spectrometry, LiHMDS is lithium hexamethyldisilazane, MTBE is methyl tert-butyl ether, NMDAR is N-methyl-d-apartate receptor, NMP is N-methyl-2-pyrrolidone, NMR is nuclear magnetic resonance, Pd/C is palladium on carbon, PMB is para-methoxybenzyl, RT is room temperature (e.g., from about 20° C. to about 25° C.), TBS and TBDMS are tert-butyldimethylsilyl, TEA is triethylamine, TLC is thin layer chromatography, TFA is trifluoroacetic acid, THF is tetrahydrofuran, TMS is trimethylsilyl, TMSCN is trimethylsilyl cyanide, and TPP is triphenylphosphine.

Example 1: Synthesis of Compound AA

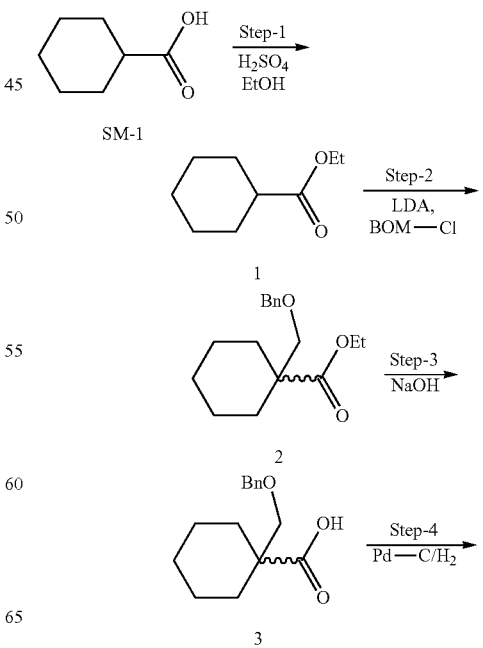

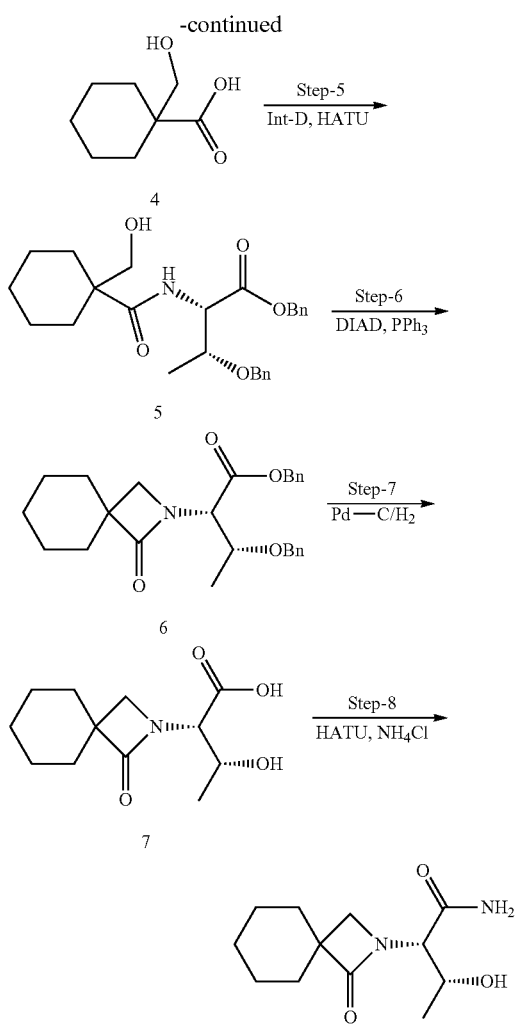

and stirred for 5 min. The reaction mixture was heated to 80° C. for 12 h. The reaction was cooled to RT and the volatiles were concentrated under reduced pressure. Crude mixture was diluted with EtOAc (20 mL), washed with water (20 mL), NaHCO$_3$ solution (20 mL) and brine solution (20 mL). The organic layer was dried over Na$_2$SO$_4$ and concentrated under reduced pressure to obtain compound 1 (15 g, 61%) as colorless liquid.

$^1$H-NMR: (500 MHz, DMSO-d$_6$): δ 4.03 (q, J=7.5 Hz, 2H), 2.29-2.24 (m, 1H), 1.81-1.78 (m, 2H), 1.67-1.56 (m, 3H), 1.37-1.16 (m, 8H).

LCMS (ESI): m/z 157.3 [M$^+$]

Synthesis of ethyl 1-((benzyloxy)methyl)cyclohexane-1-carboxylate (2)

To a stirring solution of diisopropyl amine (6.7 mL, 47.4 mmol) in THF (50 mL) was added n-BuLi (1.6 M solution in THF, 30 mL, 48.1 mmol) drop wise at −70° C. The reaction mixture was warmed to −20° C. and stirred for 30 min. Again cooled to −70° C., compound 1 (5 g, 32.1 mmol) was added, warmed to −50° C. and stirred for 30 min. To this was added BOM-chloride (8.4 mL, 63.6 mmol)−70° C., warmed to −50° C. and stirred for 30 min. After consumption of the starting material (by TLC), the reaction was quenched with aqueous NH$_4$Cl solution (50 mL) and extracted with EtOAc (2×100 mL). The combined organic layer was washed with water (2×50 mL) followed by brine solution (2×50 mL). The organic layer was dried over Na$_2$SO$_4$ and concentrated to obtain crude compound which was purified by column chromatography by eluting with 5% EtOAc/hexanes to afford compound 2 (7 g, crude) as light yellow syrup.

$^1$H-NMR: (500 MHz, DMSO-d$_6$): δ 7.37-7.24 (m, 5H), 4.42 (s, 2H), 4.09-4.02 (m, 2H), 3.40 (s, 2H), 1.98-1.92 (m, 2H), 1.48 (s, 2H), 1.30-1.12 (m, 9H).

LCMS (ESI): m/z 277.4 [(M$^+$+1)]

Synthesis of 1-((benzyloxy)methyl)cyclohexane-1-carboxylic acid (3)

To a stirring solution of compound 2 (7 g, 25.3 mmol) in EtOH:THF (40 mL, 1:1) was added NaOH solution (10 g in 20 mL H$_2$O) at RT. The reaction mixture was heated to 80° C. and stirred for 12 h. After consumption of the starting material (by TLC), volatiles were evaporated under reduced pressure and the crude was diluted with water (100 mL) and extracted with Et$_2$O (2×100 mL). The separated aqueous layer was acidified using 2 N HCl solution (pH-2-3) and extracted with EtOAc (2×100 mL). Combined organic layer was dried over Na$_2$SO$_4$ and concentrated to obtain crude compound which was purified by column chromatography by eluting with 10% EtOAc/hexanes to afford compound 3 (2.5 g, 40%) as thick syrup.

$^1$H-NMR: (400 MHz, DMSO-d$_6$): δ 12.08 (s, 1H), 7.35-7.25 (m, 5H), 4.44 (s, 2H), 3.41 (s, 2H), 1.92-1.89 (m, 2H), 1.55-1.47 (m, 3H), 1.35-1.23 (m, 5H).

LCMS (ESI): m/z 247.2 [M$^+$−1]

Synthesis of 1-(hydroxymethyl)cyclohexane-1-carboxylic acid (4)

To a stirring solution of compound 3 (2.5 g, 1.01 mmol) in methanol (50 mL) was added 50% wet 10% Pd/C (1 g) at Synthesis of ethyl cyclohexanecarboxylate (1)

To a solution of cyclohexanecarboxylic acid (SM-1) (20 g, 156.2 mmol) in ethanol (200 mL) was added sulfuric acid (8.5 mL, 156.2 mmol) at 0° C. under nitrogen atmosphere RT and stirred for 12 h under H$_2$ atmosphere (balloon pressure). After consumption of the starting material (by TLC), the reaction mixture was filtered through a pad of celite and the pad was washed with EtOAc (50 mL). Obtained filtrate was concentrated under reduced pressure to afford compound 4 (1.3 g, 81%) as off white solid.

$^1$H-NMR: (400 MHz, DMSO-d$_6$): δ 12.04 (s, 1H), 3.36 (s, 2H), 1.88-1.85 (m, 2H), 1.51-1.48 (m, 3H), 1.32-1.15 (m, 5H).

LCMS (ESI): m/z 157.0 [M$^+$−1]

Synthesis of benzyl O-benzyl-N-(1-(hydroxymethyl)cyclohexane-1-carbonyl)-L-threoninate (5)

To a stirring solution of compound 4 (1 g, 6.3 mmol) in DCM (20 mL) were added DIPEA (3.2 mL, 7.5 mmol), HATU (3.6 g, 9.4 mmol) and Int-D (2.5 g, 7.5 mmol) at 0° C. under nitrogen atmosphere. The reaction mixture was warmed to RT and stirred for 12 h. After consumption of the starting material (by TLC), the reaction mixture was diluted with CH$_2$Cl$_2$ (20 mL) and washed with saturated NaHCO$_3$ solution, 2 N HCl solution and brine solution. Organic layer was dried over anhydrous Na$_2$SO$_4$ and concentrated under reduced pressure to afford crude compound which was purified by column chromatography by eluting with 20% EtOAc/hexanes to obtain compound 5 (1 g, 47%) as thick syrup.

$^1$H-NMR: (500 MHz, DMSO-d$_6$): δ 7.51 (d, J=8.5 Hz, 1H), 7.31-7.20 (m, 10H), 5.16 (t, J=5.0 Hz, 1H), 5.10 (s, 2H), 4.55-4.49 (m, 1H), 4.33-4.30 (m, 1H), 4.05 (s, 2H), 3.41 (d, J=5.0 Hz, 2H), 1.40-1.23 (m, 10H), 1.18-1.13 (m, 3H).

LCMS (m/z): 440.5 [M$^+$+1]

Synthesis of benzyl (2S,3R)-3-(benzyloxy)-2-(1-oxo-2-azaspiro[3.5]nonan-2-yl)butanoate (6)

To a solution of TPP (864 mg, 3.3 mmol) in THF (20 mL) was added DIAD (690 mg, 3.4 mmol) at RT under nitrogen atmosphere and the reaction mixture was stirred for 20 minutes. The reaction mixture was cooled to 0° C., added compound 5 (1 g, 2.2 mmol) in THF (10 mL) warmed to RT and stirred for 4 h. After consumption of the starting material (by TLC), the volatiles were concentrated under reduced pressure to obtain the crude which was purified by silica gel column chromatography eluting with 10% EtOAc/hexanes to afford compound 6 (1.4 g, crude) as thick syrup.

$^1$H-NMR: (500 MHz, DMSO-d$_6$): δ 7.31-7.21 (m, 10H), 5.12 (s, 2H), 4.55 (s, 2H), 4.29-4.26 (m, 1H), 4.18-4.16 (m, 1H), 3.35-3.28 (m, 2H), 1.36-1.12 (m, 13H).

LCMS (ESI): m/z 422.4 [(M$^+$+1)]

Synthesis of (2S,3R)-3-hydroxy-2-(1-oxo-2-azaspiro [3.5]nonan-2-yl)butanoic acid (7)

To a stirring solution of compound 6 (1.4 g, 3.3 mmol) in methanol (30 mL) was added 50% wet 10% Pd/C (600 mg) at RT and stirred for 12 h under H$_2$ atmosphere (balloon pressure). After consumption of the starting material (by TLC), the reaction mixture was filtered through a pad of celite, washed with methanol (50 mL). Obtained filtrate was concentrated under reduced pressure to afford compound 7 (700 g, crude) as sticky syrup.

$^1$H-NMR: (400 MHz, DMSO-d$_6$): δ 4.89-4.73 (m, 2H), 4.18-4.16 (m, 1H), 3.16 (s, 2H), 1.23-1.08 (m, 13H).

LCMS (m/z): 242.2 [M$^+$+1]

Synthesis of (2S,3R)-3-hydroxy-2-(1-oxo-2-azaspiro [3.5]nonan-2-yl)butanamide (AA)

To a stirring solution of compound 7 (700 mg, 2.9 mmol) in DMF (5 mL) were added DIPEA (1.5 mL, 8.7 mmol), NH$_4$Cl (388 mg, 7.2 mmol) and HATU (1.65 g, 4.3 mmol) at 0° C. under nitrogen atmosphere. The reaction mixture was stirred at RT for 12 h. After consumption of the starting material (by TLC), the reaction mixture was diluted with ice cold-water (30 mL) and extracted with EtOAc (2×30 mL). The combined organic layer was washed with brine solution, dried over anhydrous Na$_2$SO$_4$, filtered and concentrated under reduced pressure. Obtained crude material was purified by silica gel column chromatography eluting with 5% MeOH/CH$_2$Cl$_2$ and further purified by prep HPLC to afford AA (80 mg, 11.4%) as thick syrup.

$^1$H-NMR: (500 MHz, DMSO-d$_6$): δ 7.45 (s, 1H), 7.06 (s, 1H), 4.88 (d, J=4.4 Hz, 1H), 3.98-3.94 (m, 1H), 3.90 (d, J=5.2 Hz, 1H), 3.31-3.23 (m, 2H), 1.66-1.60 (m, 6H), 1.47 (br s, 1H), 1.37-1.23 (m, 3H), 1.06 (d, J=4.4 Hz, 3H).

LCMS (ESI): m/z 241.1 [M$^+$+1]

HPLC: 98.89%

Synthesis of (2S,3R)-benzyl 2-amino-3-(benzyloxy) butanoate (Intermediate D)

To a stirring solution of compound C (290 g, 0.74 mol) in diethyl ether (500 mL) was added 2 M HCl in diethyl ether (1 L) at 0° C. and stirred at RT for 10 h. After consumption of the starting material (by TLC), the reaction mixture was concentrated under reduced pressure. The crude material was triturated with diethyl ether/n-pentane (100 mL/100 mL) and dried under reduced pressure to afford compound D (187 g, 86%) as white solid (HCl salt).

$^1$H-NMR: (400 MHz, DMSO-d$_6$): δ 8.59 (s, 2H), 7.50-7.25 (m, 10H), 5.23 (d, J=12.5 Hz, 1H), 5.16 (d, J=12.5 Hz, 1H), 4.54 (d, J=12.0 Hz, 1H), 4.36 (d, J=12.0 Hz, 1H), 4.12-4.09 (m, 1H), 4.09-3.99 (m, 1H), 1.29 (d, J=6.5 Hz, 3H)

Mass (ESI): m/z 299.4 [M$^+$+1]

Example 2: Synthesis of Compound AB

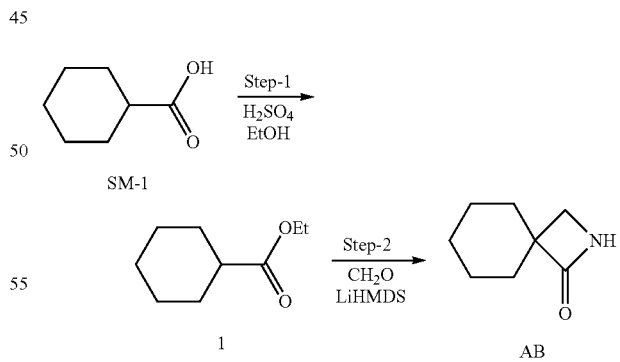

Synthesis of ethyl cyclohexanecarboxylate (1)

To a solution of cyclohexanecarboxylic acid (SM-1) (10 g, 78.1 mmol) in ethanol (100 mL) was added sulfuric acid (4.2 mL, 78.1 mmol) at 0° C. under nitrogen atmosphere and stirred for 5 min. and then heated to 80° C. for 16 h. The reaction mixture was cooled to RT and volatiles were concentrated under reduced pressure. Crude mixture was diluted with EtOAc (10 mL) and washed with water (10 mL), NaHCO$_3$ solution (10 mL) and brine solution (10 mL). Organic layer was dried over Na$_2$SO$_4$ and concentrated to obtain compound 1 (7 g, 61%) as colorless liquid.

$^1$H-NMR: (500 MHz, DMSO-d$_6$): δ 4.03 (q, J=7.5 Hz, 2H), 2.29-2.25 (m, 1H), 1.81-1.78 (m, 2H), 1.67-1.56 (m, 3H), 1.37-1.16 (m, 8H).

Synthesis of 2-azaspiro[3.5]nonan-1-one (AB)

To a solution of compound 1 (2 g, 12.8 mmol) in THF (20 mL) was added para formaldehyde (460 mg, 15.3 mmol) at RT and stirred for 5 min. The reaction mixture was cooled to −70° C., added LiHMDS (1M solution in THF) (38.4 mL, 38.4 mmol), warmed to RT and stirred for 12 h. After consumption of the starting material (by TLC), quenched with water (20 mL) and extracted with EtOAc (2×20 mL). Combined organic layer was washed with water (10 mL) followed by brine solution (10 mL). The organic layer was dried over Na$_2$SO$_4$ and concentrated to obtain crude compound which was purified by column chromatography by eluting 30% EtOAc/hexanes and further purified by preparative HPLC to afford AB (200 mg, 11%) as off white solid.

$^1$H-NMR: (500 MHz, DMSO-d$_6$): δ 7.62 (s, 1H), 2.94 (s, 2H), 1.67-1.54 (m, 6H), 1.48-4.46 (m, 1H), 1.35-1.26 (m, 3H).

LCMS (ESI): m/z 140.0 [(M$^+$+1)]

Example 3—Synthesis of Compound AC

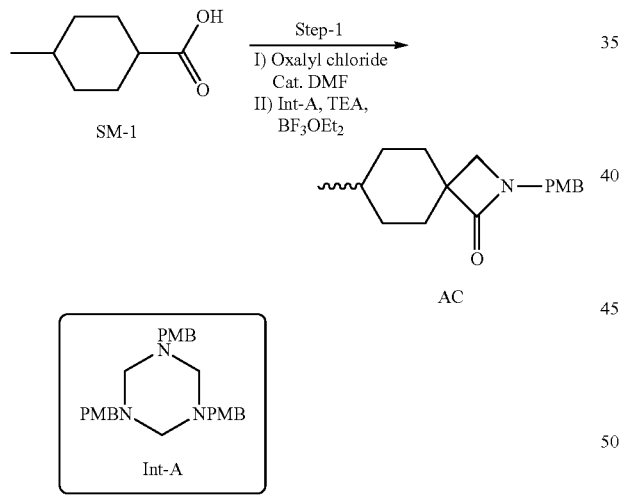

Synthesis of 2-(4-methoxybenzyl)-7-methyl-2-azaspiro[3.5]nonan-1-one (AC)

To a solution of 4-methylcyclohexane-1-carboxylic acid (SM-1) (500 mg, 3.52 mmol) in CH$_2$Cl$_2$ (3 mL) were added oxalyl chloride (0.6 mL, 69.9 mmol) and catalytic amount of DMF at 0° C. under nitrogen atmosphere warmed to RT and stirred for 2 h. After consumption of the starting material (by TLC) the volatiles were concentrated under reduced pressure. Obtained crude material was dissolved in CH$_2$Cl$_2$ (3 mL) and Et$_3$N (2.2 mL, 17.6 mmol) was added slowly at −40° C. and stirred for 10 min. In another flask, a solution of Int-A (620 mg, 1.41 mmol) in CH$_2$Cl$_2$ (3 mL) was added BF$_3$.OEt$_2$ (0.46 mL, 3.52 mmol) drop wise at RT and stirred for 30 minutes. Then, this mixture was added to crude material-Et$_3$N mixture at −40° C. and gradually raised temperature to RT and stirred for 3 h. After consumption of the starting material (by TLC), the reaction was diluted with water (20 mL) and extracted with EtOAc (3×30 mL). Combined organic layer was dried over Na$_2$SO$_4$ and concentrated under reduced pressure to afford crude material which was purified by column chromatography by eluting 20% EtOAc/hexanes to obtain compound AC (600 mg, 66%) as thick syrup.

$^1$H NMR (400 MHz, DMSO-d$_6$): δ 7.17-7.12 (m, 2H), 6.94-6.89 (m, 2H), 4.21 (s, 2H), 3.74 (s, 3H), 2.81 (s, 2H), 1.87-1.80 (m, 2H), 1.59-1.49 (m, 4H), 1.45-1.34 (m, 3H), 0.88 (d, J=5.9 Hz, 3H).

LCMS (ESI): m/z 274.38 [M$^+$+1]
HPLC: 99.10%
Chiral HPLC: 100.00%

Example 4—Synthesis of Compound AD

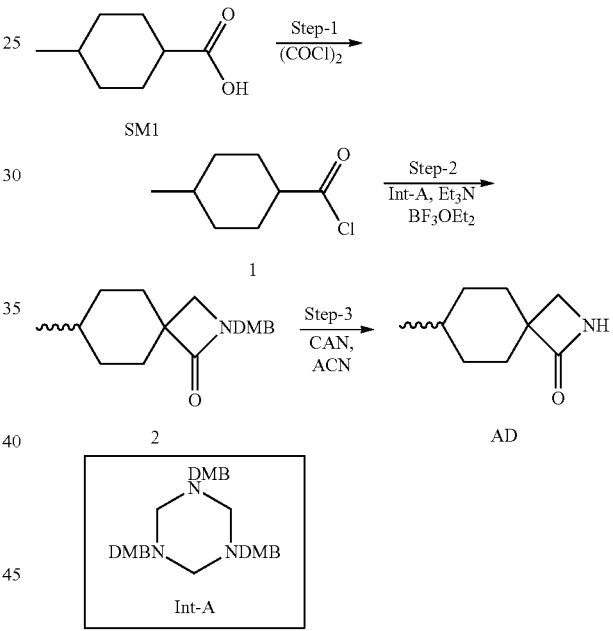

Synthesis of 4-methylcyclohexane-1-carbonyl chloride (1)

To a stirring solution of 4-methylcyclohexane-1-carboxylic acid (SM1) (2 g, 14.1 mmol) in CH$_2$Cl$_2$ (20 mL) was added oxalyl chloride (2.48 mL, 28.1 mmol) and catalytic amount of DMF (0.2 mL) at 0° C.; warmed to RT and stirred for 3 h. After consumption of the starting material (by TLC) the volatiles were concentrated under reduced pressure to afford crude compound 1 (2 g) as white solid, which was taken to next step without any further purification.

Synthesis of 2-(3,4-dimethylbenzyl)-7-methyl-2-azaspiro[3.5]nonan-1-one (2)

To a stirring solution of crude compound 1 (2 g, 12.5 mmol) in CH$_2$Cl$_2$ (15 mL) was added Et$_3$N (7.2 mL, 50.0 mmol) slowly at −40° C. and stirred for 10 min. In another flask, a solution of Int-A (2.21 g, 4.12 mmol) in CH$_2$Cl$_2$ (15 mL) was added BF$_3$.OEt$_2$ (3.5 mL, 25.0 mmol) drop wise at RT and stirred for 15 minutes. Then, this mixture was added to compound 1 mixture at −40° C. and gradually raised temperature to RT and stirred for 16 h. After consumption of the starting material (by TLC), the reaction was diluted with water (50 mL) and extracted with CH$_2$Cl$_2$ (3×30 mL). Combined organic layer was washed with 1N HCl solution (30 mL), dried over Na$_2$SO$_4$ and concentrated under reduced pressure to afford crude material which was purified by column chromatography by eluting with 20% EtOAc/hexanes to obtain compound 2 (1 g, 26%) as colorless syrup.

LCMS (ESI): m/z 304.3 [(M$^+$+1)]

Synthesis of 7-methyl-2-azaspiro[3.5]nonan-1-one (AD)

To a stirring solution of compound 2 (500 mg, 1.65 mmol) in ACN:H$_2$O (16 mL, 1:1) was added CAN (1.8 g, 3.30 mmol) in ACN:H$_2$O (4 mL, 1:1) at 0° C. and stirred at the same temperature for 1 h. After consumption of the starting material (by TLC), the reaction mixture was diluted with EtOAc (20 mL), washed with aqueous NaHCO$_3$ solution (20 mL). Organic layer was dried over Na$_2$SO$_4$ and concentrated to obtain the crude which was purified by column chromatography eluting with 10% EtOAc/hexanes to afford racemic compound AD (45 mg, 18%) as an off white solid.

$^1$H NMR (400 MHz, DMSO-d$_6$): δ 7.52 (br s, 1H), 2.86 (s, 2H), 1.93-1.80 (m, 2H), 1.61-1.52 (m, 4H), 1.47-1.36 (m, 3H), 0.88 (d, J=5.9 Hz, 3H)

LCMS (ESI): m/z 154.3 [M$^+$+1]
HPLC: 94.17%

Preparation of Int-A

Synthesis of 1,3,5-tris(3,4-dimethylbenzyl)-1,3,5-triazinane (Int-A)

To a stirring solution of (2,4-dimethoxyphenyl)methanamine (10 g, 59.8 mmol) in ethanol (100 mL) was added formalin solution (6 mL) at RT and continued stirring for 2 h. After consumption of the starting material (by TLC), volatiles were concentrated under reduced pressure. Obtained crude was dissolved in EtOAc (100 mL), washed with water (2×50 mL) and concentrated under reduced pressure. Crude material was triturated with EtOH:n-hexane (1:1) and dried to afford Int-A (10 g, 93%) as an off-white solid.

$^1$H NMR (400 MHz, CDCl$_3$): δ 7.19 (d, J=8.0 Hz, 3H), 6.44-6.37 (m, 6H), 3.80 (s, 9H), 3.77 (s, 9H), 3.70-3.60 (m, 6H), 3.48 (br s, 3H).

LCMS (ESI): m/z 537.66 [M$^+$+1]
HPLC: 93.4%.

Example 5—Synthesis of Compounds AE, AF, AG and AH

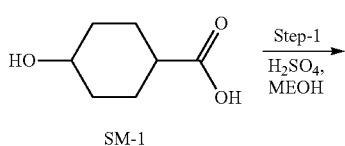

SM-1

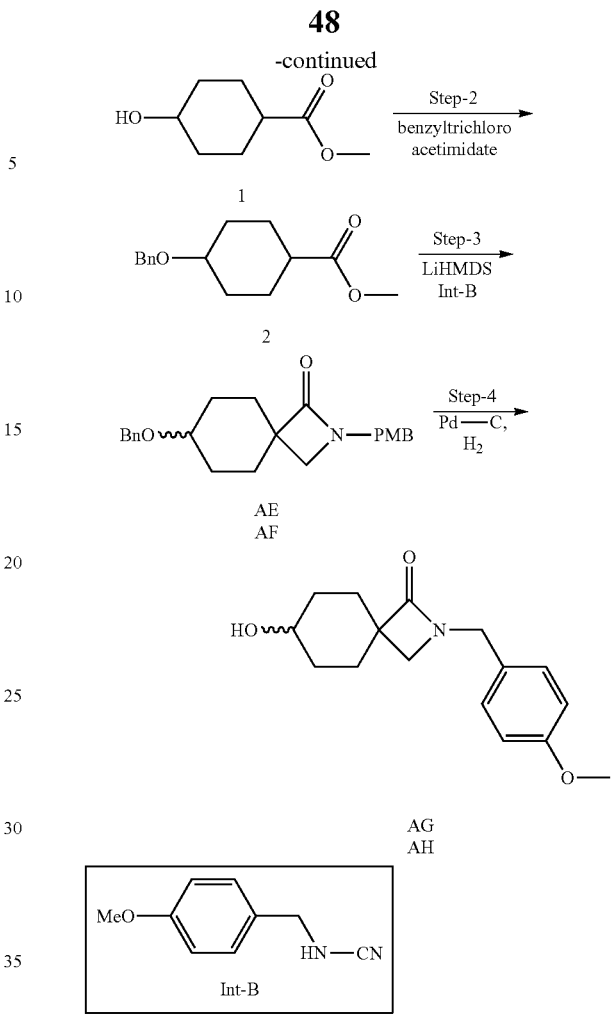

Synthesis of methyl 4-hydroxycyclohexane-1-carboxylate (1)

To a stirred suspension of 4-hydroxycyclohexane-1-carboxylic acid (SM-1) (15 g, 104.1 mmol) in methanol (30 mL) was added sulfuric acid (0.9 mL, 15.6 mmol) drop wise at room temperature under nitrogen atmosphere and stirred at RT for 5 h. After consumption of the starting material (by TLC), the reaction was quenched with water (50 mL) and extracted with EtOAc (2×100 mL). Combined organic layer was washed with saturated NaHCO$_3$ solution and brine solution. Organic layer was dried over Na$_2$SO$_4$ and concentrated under reduced pressure to afford compound 1 (13.5 g, 82%) as liquid.

$^1$H NMR (500 MHz, DMSO-d$_6$): δ 4.38 (d, J=3.5 Hz, 1H), 3.65 (br d, J=3.5 Hz, 1H), 3.59 (s, 3H), 2.40-2.32 (m, 1H), 1.88-1.74 (m, 4H), 1.55-1.44 (m, 2H), 1.39-1.28 (m, 1H), 1.20-1.09 (m, 1H).

LCMS (m/z): 159.1 [M$^+$+1]

Synthesis of methyl 4-(benzyloxy)cyclohexane-1-carboxylate (2)

To a stirring solution of compound 1 (6 g, 37.9 mmol) in hexane:chloroform (45 mL, 2:1) were added benzyltrichloro acetimidate (11.04 mL, 56.9 mmol) followed by drop wise addition of triflic acid (0.5 mL, 5.69 mmol) at 0° C. The reaction mixture was warmed to RT and stirred for 24 h.

After consumption of the starting material (by TLC), the reaction was diluted with EtOAc (50 mL), washed with saturated NaHCO$_3$ solution and brine solution. Organic layer was separated, dried over Na$_2$SO$_4$ and concentrated under reduced pressure to afford crude compound which was purified by column chromatography by eluting with 10% EtOAc/hexanes to obtain compound 2 (6.5 g, 69%) as liquid.

$^1$H NMR (400 MHz, DMSO-d$_6$): δ 7.39-7.21 (m, 5H), 4.51-4.44 (m, 2H), 3.61-3.52 (m, 4H), 2.4-2.37 (m, 1H), 2.07-1.86 (m, 1H), 1.81-1.67 (m, 3H), 1.65-1.48 (m, 3H), 1.43-1.18 (m, 1H).

LCMS (ESI): m/z 249.1 [(M$^+$+1)

Synthesis of 7-(benzyloxy)-2-(4-methoxybenzyl)-2-azaspiro[3.5]nonan-1-one (AE, AF)

To a solution of compound 2 (2 g, 8.06 mmol) in dry THF (15 mL) was added LiHMDS (1.0M in THF) (16 mL, 16.1 mmol) at −50° C. under nitrogen atmosphere. After stirring for 1 h, Int-A (1.4 g, 8.06 mmol) was added at −50° C. and warmed to RT and stirred for 6 h. After consumption of the starting material (by TLC), the reaction was quenched with ice water (20 mL) and extracted with EtOAc (2×30 mL). The combined organic layer was washed with brine solution (2×10 mL), dried over Na$_2$SO$_4$ and concentrated to obtain crude compound which was purified by column chromatography by eluting with 20% EtOAc/hexanes to afford compound AE (1 g of isomeric mixture) and eluting with 30% EtOAc/hexanes to afford compound AF (500 mg of isomeric mixture) as an off white solid, (500 mg, isomeric mixture) was subjected for further purified by normal phase HPLC purification to give 160 mg of AE and 250 mg of AF as white solid.

AE:
$^1$H NMR (400 MHz, DMSO-d$_6$): δ 7.36-7.22 (m, 5H), 7.16 (d, J=8.6 Hz, 2H), 6.92 (d, J=8.6 Hz, 2H), 4.48 (s, 2H), 4.23 (s, 2H), 3.74 (s, 3H), 3.44-3.34 (m, 1H), 2.94 (s, 2H), 2.04-1.93 (m, 2H), 1.78-1.69 (m, 2H), 1.63-1.53 (m, 2H), 1.38-1.25 (m, 2H)

LCMS (ESI): m/z 366.1 [M$^+$+1];
HPLC: 92.30%
Chiral HPLC: 91.20%

AF:
$^1$H NMR (400 MHz, DMSO-d$_6$): δ 7.38-7.30 (m, 4H), 7.30-7.23 (m, 1H), 7.16 (d, J=8.6 Hz, 2H), 6.95-6.89 (m, 2H), 4.48 (s, 2H), 4.23 (s, 2H), 3.74 (s, 3H), 3.50-3.46 (m, 1H), 2.91 (s, 2H), 1.93-1.75 (m, 4H), 1.69-1.58 (m, 2H), 1.53-1.43 (m, 2H)

LCMS (ESI): m/z 366.1 [M$^+$+1];
HPLC: 95.72%
Chiral HPLC: 98.27%

Synthesis of 7-hydroxy-2-(4-methoxybenzyl)-2-azaspiro[3.5]nonan-1-one (AH)

To a stirring solution of AF (100 mg, 0.27 mmol) in MeOH (10 mL) was added 10% Pd/C (50 mg) at RT under N$_2$ atmosphere. Then the reaction mixture was stirred for 1 h under H$_2$ atmosphere. After consumption of the starting material (by TLC), reaction mixture was filtered through a pad of celite and the filtrate was concentrated under reduced pressure to afford AH (60 mg, 79%) as thick syrup.

$^1$H NMR (400 MHz, DMSO-d$_6$): δ 7.15 (d, J=8.5 Hz, 2H), 6.92 (d, J=8.5 Hz, 2H), 4.45 (d, J=3.8 Hz, 1H), 4.21 (s, 2H), 3.74 (s, 3H), 3.58-3.53 (m, 1H), 2.86 (s, 2H), 1.92-1.83 (m, 2H), 1.67-1.51 (m, 4H), 1.49-1.44 (m, 2H)

LCMS (ESI): m/z 275.9 [M$^+$+1];
HPLC: 99.41%
Chiral HPLC: 99.31%

Example 6—Synthesis of Compounds AI, AJ, AK and AL

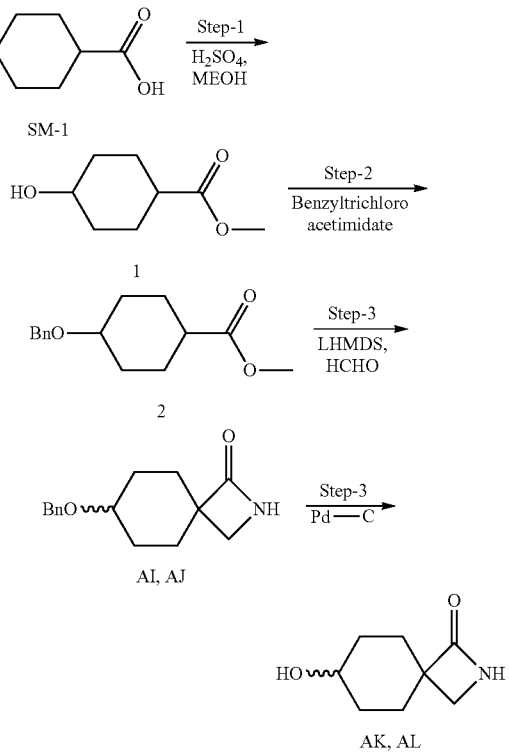

Synthesis of methyl 4-hydroxycyclohexane-1-carboxylate (1)

To a stirred suspension of 4-hydroxycyclohexane-1-carboxylic acid (SM-1) (15 g, 104.1 mmol) in methanol (30 mL) was added sulfuric acid (0.9 mL, 15.6 mmol) drop wise at RT and stirred for 5 h. After consumption of the starting material (by TLC), reaction was quenched with water (50 mL) and extracted with EtOAc (2×100 mL). Combined organic layer was washed with saturated NaHCO$_3$ solution and brine solution. Organic layer was dried over Na$_2$SO$_4$ and concentrated under reduced pressure to afford compound 1 (13.5 g, 82%) as liquid.

$^1$H NMR (500 MHz, DMSO-d$_6$): δ 4.38 (d, J=3.5 Hz, 1H), 3.65 (br d, J=3.5 Hz, 1H), 3.59 (s, 3H), 2.40-2.32 (m, 1H), 1.88-1.74 (m, 4H), 1.55-1.44 (m, 2H), 1.39-1.28 (m, 1H), 1.20-1.09 (m, 1H).

LCMS (m/z): 159.2 [M$^+$+1]

Synthesis of methyl 4-(benzyloxy)cyclohexane-1-carboxylate (2)

To a stirring solution of compound 1 (6 g, 37.9 mmol) in hexane:chloroform (45 mL, 2:1) were added benzyltrichloro acetimidate (11.04 mL, 56.9 mmol) followed by drop wise addition of triflic acid (0.5 mL, 5.69 mmol) at 0° C. The reaction mixture was warmed to RT and stirred for 24 h. After consumption of the starting material (by TLC), the reaction was diluted with EtOAc (50 mL) and washed with saturated NaHCO$_3$ solution and brine solution. Organic layer was separated, dried over Na$_2$SO$_4$ and concentrated under reduced pressure to afford crude compound which was purified by column chromatography by eluting with 10% EtOAc/hexanes to obtain compound 2 (6.5 g, 69%) as liquid.

$^1$H NMR (400 MHz, DMSO-d$_6$): δ 7.39-7.21 (m, 5H), 4.51-4.44 (m, 2H), 3.61-3.52 (m, 4H), 2.4-2.37 (m, 1H), 2.07-1.86 (m, 1H), 1.81-1.67 (m, 3H), 1.65-1.48 (m, 3H), 1.43-1.18 (m, 1H).

LCMS (ESI): m/z 249.1 [(M$^+$+1)

Synthesis of 7-(benzyloxy)-2-azaspiro[3.5]nonan-1-one (AI and AJ)

To a stirring solution of compound 2 (5 g, 20.1 mmol) in dry THF (50 mL) were added paraformaldehyde (665 g, 22.1 mmol) and LiHMDS (1.0M in THF) (60 mL, 60.4 mmol) at −50° C. under nitrogen atmosphere. The reaction mixture was brought to RT and stirred for 6 h. After consumption of the starting material (by TLC), the reaction was quenched with ice water (20 mL) and extracted with EtOAc (2×30 mL). The combined organic layer was washed with brine solution (2×10 mL), dried over Na$_2$SO$_4$ and concentrated to obtain crude compound which was purified by column chromatography by eluting 30% EtOAc/hexanes to afford racemic AI, AJ (600 mg, 12%) as an off white solid, which was separated by normal phase HPLC purification to give 120 mg of AI and 222 mg of AJ as white solids.

AI:
$^1$H NMR (400 MHz, DMSO-d$_6$): δ 7.68 (br s, 1H), 7.37-7.23 (m, 5H), 4.49 (s, 2H), 3.43-3.34 (m, 1H), 2.99 (s, 2H), 2.04-1.95 (m, 2H), 1.79-1.74 (m, 2H), 1.60-1.50 (m, 2H), 1.38-1.25 (m, 2H).
LCMS (ESI): m/z 246.0 [M$^+$+1];
HPLC: 96.16%

AJ:
$^1$H NMR (400 MHz, DMSO-d$_6$): δ 7.65 (br s, 1H), 7.38-7.24 (m, 5H), 4.48 (s, 2H), 3.51-3.47 (m, 1H), 2.96 (s, 2H), 1.93-1.76 (m, 4H), 1.69-1.60 (m, 2H), 1.55-1.46 (m, 2H)
LCMS (ESI): m/z 246.0 [M$^+$+1];
HPLC: 98.09%
Chiral HPLC: 97.15%

Synthesis of 7-hydroxy-2-azaspiro[3.5]nonan-1-one (AK)

To a stirring solution of AI (55 mg, 0.22 mmol) in methanol (10 mL) was added 10% Pd/C (20 mg) at RT under N$_2$ atmosphere. Then the reaction mixture was stirred for 1 h under H$_2$ atmosphere (balloon pressure). After consumption of the starting material (by TLC), reaction mixture was filtered through a pad of celite and the filtrate was concentrated under reduced pressure to obtain crude which was purified by column chromatography by eluting 2% MeOH/CH$_2$Cl$_2$ to afford compound AK (28 mg, 80%) as white solid.

$^1$H NMR (500 MHz, DMSO-d$_6$): δ 7.66 (br s, 1H), 4.53 (d, J=4.3 Hz, 1H), 3.44-3.35 (m, 1H), 2.97 (s, 2H), 1.85-1.76 (m, 2H), 1.74-168 (m, 2H), 1.55-1.48 (m, 2H), 1.21-1.10 (m, 2H).
LCMS (ESI): m/z 156.3 [M$^+$+1];
HPLC: 94.53%

Synthesis of 7-hydroxy-2-azaspiro[3.5]nonan-1-one (AL)

To a stirring solution of AJ (140 mg, 0.57 mmol) in methanol (20 mL) was added 10% Pd/C (75 mg) at RT under N$_2$ atmosphere. Then the reaction mixture was stirred for 1 h under H$_2$ atmosphere (balloon pressure). After consumption of the starting material (by TLC), reaction mixture was filtered through a pad of celite and the filtrate was concentrated under reduced pressure to obtain crude which was purified by column chromatography by eluting 5% MeOH/CH$_2$Cl$_2$ to afford AL (38 mg, 43%) as white solid.

$^1$H NMR (500 MHz, DMSO-d$_6$): δ 7.61 (br s, 1H), 4.43 (d, J=3.8 Hz, 1H), 3.59-3.51 (m, 1H), 2.91 (s, 2H), 1.92-1.87 (m, 2H), 1.67-1.52 (m, 4H), 1.51-1.43 (m, 2H)
LCMS (ESI): m/z 156.2 [M$^+$+1];
HPLC: 99.63%

Example 7—Synthesis of Compound AM

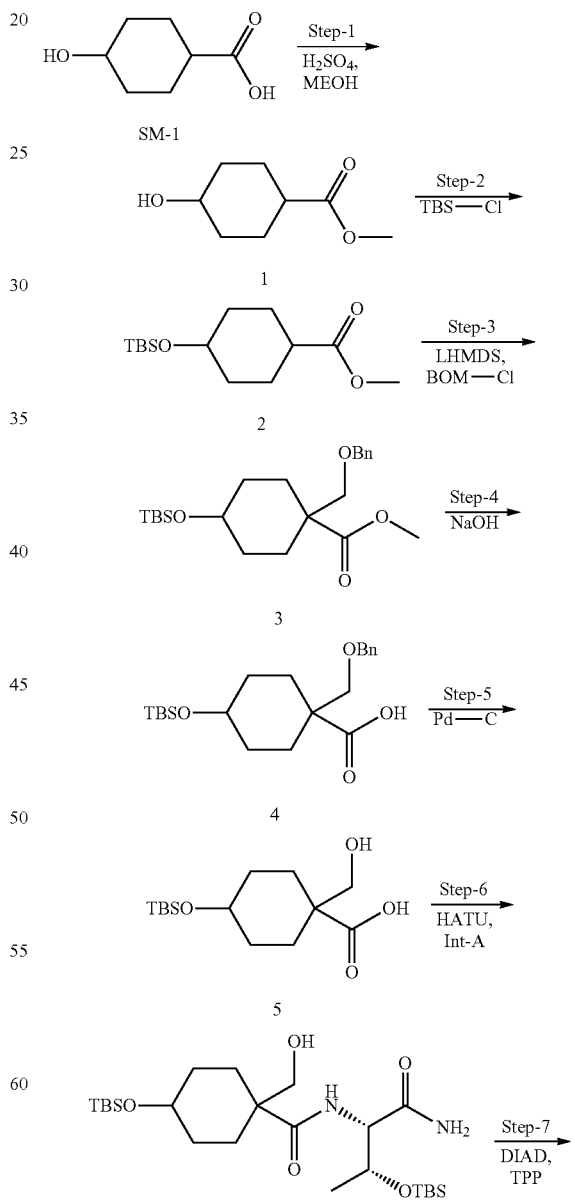

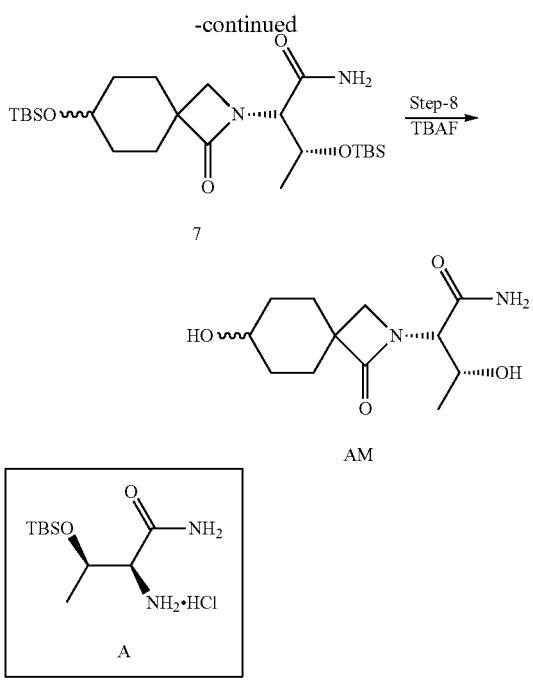

Synthesis of methyl 4-hydroxycyclohexane-1-carboxylate (1)

To a stirred solution of 4-hydroxycyclohexane-1-carboxylic acid (SM-1) (25 g, 173.6 mmol) in methanol (100 mL) was added catalytic amount of sulfuric acid (1.5 mL, 26.1 mmol) at RT. The reaction mixture was stirred RT for 16 h. After consumption of the starting material (by TLC), the reaction mixture was quenched with water and extracted with EtOAc (2×100 mL). Separated organic layer was washed with saturated NaHCO$_3$ solution and brine solution. Organic layer was dried over Na$_2$SO$_4$ and concentrated under reduced pressure and triturated with n-pentane to afford compound 1 (22.5 g, 80%) as white solid.

$^1$H NMR (500 MHz, DMSO-d$_6$): δ 4.38 (d, J=3.5 Hz, 1H), 3.65 (br d, J=3.5 Hz, 1H), 3.59 (s, 3H), 2.40-2.32 (m, 1H), 1.88-1.74 (m, 4H), 1.55-1.44 (m, 2H), 1.39-1.28 (m, 1H), 1.20-1.09 (m, 1H).

Synthesis of methyl 4-((tert-butyldimethylsilyl)oxy)cyclohexane-1-carboxylate (2)

To a stirred solution of compound 1 (10 g, 63.2 mmol) in DMF (50 mL) were added imidazole (10.7 g, 158 mmol) and TBDMS-C$_1$ (10.6 g, 70.7 mmol) at 0° C. The reaction mixture was warmed to RT and stirred for 16 h. After consumption of the starting material (by TLC), the reaction was quenched with ice water (50 mL) and extracted with diethyl ether (2×50 mL). The combined organic layer was washed with citric acid solution and brine solution. The organic layer was dried over Na$_2$SO$_4$ and concentrated under reduced pressure to afford crude compound which was purified by column chromatography by eluting with 10% EtOAc/hexanes to obtain compound 2 (12 g, 69%) as oily liquid.

$^1$H NMR (500 MHz, DMSO-d$_6$): δ 3.61 (s, 3H), 3.59-3.54 (m, 1H), 2.29-2.20 (m, 1H), 1.90-1.71 (m, 3H), 1.60-1.46 (m, 5H), 0.86 (s, 9H), 0.02 (s, 6H).

Synthesis of methyl 1-((benzyloxy)methyl)-4-((tert-butyldimethylsilyl)oxy)cyclohexane-1-carboxylate (3)

To a stirring solution of compound 2 (11 g, 40.4 mmol) in dry THF (60 mL) was added LiHMDS (1.0 M in THF) (80 mL, 80.8 mmol) at −50° C. under nitrogen atmosphere and stirred for 1 h. Then, BOM-chloride (8.3 mL, 60.6 mmol) was added drop wise) at −50° C. The reaction mixture was brought to RT and stirred for 1 h. After consumption of the starting material (by TLC), the reaction was quenched with ice water (10 mL) and extracted with diethyl ether (2×50 mL). The organic layer was dried over Na$_2$SO$_4$ and concentrated to obtain crude compound which was purified by column chromatography by eluting with 10% EtOAc/hexanes to afford compound 3 (14 g, 88%) as liquid.

$^1$H NMR (500 MHz, DMSO-d$_6$): δ 7.36-7.24 (m, 5H), 4.37 (s, 2H), 3.60 (s, 3H), 3.58-3.52 (m, 1H), 3.34 (s, 2H), 2.08-2.02 (m, 2H), 1.67-1.61 (m, 2H), 1.28-1.16 (m, 4H), 0.84 (s, 9H), 0.01 (s, 6H).

Synthesis of 1-((benzyloxy)methyl)-4-((tert-butyldimethylsilyl)oxy)cyclohexane-1-carboxylic acid (4)

To a stirring solution of compound 3 (6.5 g, 16.5 mmol) in THF:H$_2$O (30 mL, 2:1) was added NaOH solution (6.6 g, 165.8 mmol) at 0° C. The reaction mixture was heated to 80° C. for 48 h. The reaction mixture was brought to RT and volatiles were evaporated under reduced pressure. Crude material was diluted with water (20 mL) and brine solution. Aqueous layer pH was adjusted to 4 with citric acid solution and extracted with ether (2×50 mL). The combined organic layer was dried over Na$_2$SO$_4$ and concentrated to afford compound 4 (5 g, 88%) as liquid.

$^1$H NMR (500 MHz, DMSO-d$_6$): δ 7.36-7.21 (m, 5H), 4.40 (s, 2H), 3.62-3.54 (m, 1H), 3.43 (s, 2H), 2.07-2.01 (m, 2H), 1.70-1.61 (m, 2H), 1.31-1.18 (m, 4H), 0.82 (s, 9H), 0.00 (s, 6H).

Synthesis of 4-((tert-butyldimethylsilyl)oxy)-1-(hydroxymethyl)cyclohexane-1-carboxylic acid (5)

To a stirring solution of compound 4 (5 g, 13.2 mmol) in methanol (50 mL) was added 50% wet 10% Pd/C (2.5 g) at RT under nitrogen atmosphere and then stirred for 12 h under H$_2$ atmosphere (balloon pressure). After consumption of the starting material (by TLC), the reaction mixture was filtered through a pad of celite and washed with EtOAc (50 mL). Obtained filtrate was concentrated under reduced pressure to afford compound 5 (1.3 g, 34%) as an off white solid.

$^1$H NMR (400 MHz, DMSO-d$_6$): δ 11.82 (br s, 1H), 4.43 (br s, 1H), 3.36-3.27 (m, 3H), 1.98-1.92 (m, 2H), 1.71-1.62 (m, 2H), 1.23-1.07 (m, 4H), 0.84 (s, 9H), 0.01 (s, 6H).

Synthesis of N-((2S,3R)-1-amino-3-((tert-butyldimethylsilyl)oxy)-1-oxobutan-2-yl)-4-((tert-butyldimethylsilyl)oxy)-1-(hydroxymethyl)cyclohexane-1-carboxamide (6)

To a stirring solution of compound 5 (1.3 g, 4.51 mmol) in CH$_2$Cl$_2$ (15 mL) were added Int A (1.04 g, 4.51 mmol), HATU (2.05 g, 5.41 mmol) and DIPEA (1.6 mL, 9.02 mmol) at 0° C. under nitrogen atmosphere. The reaction mixture warmed to RT and stirred for 16 h. After consumption of the starting material (by TLC), the reaction mixture was diluted with water (10 mL) and extracted with CH$_2$Cl$_2$ (2×10 mL). Separated organic layer was dried over anhydrous Na$_2$SO$_4$ and concentrated under reduced pressure to afford crude compound which was purified by column chromatography by eluting with 40% EtOAc/hexanes to obtain compound 6 (800 mg, 35%) as liquid.

$^1$H NMR (400 MHz, DMSO-d$_6$): δ 7.30 (s, 1H), 7.12 (s, 1H), 6.81 (d, J=8.9 Hz, 1H), 5.36 (t, J=5.1 Hz, 1H), 4.44-4.31 (m, 1H), 4.14-4.04 (m, 1H), 3.62 (d, J=8.7 Hz, 1H), 3.46-3.33 (m, 1H), 3.28 (br d, J=5.4 Hz, 1H), 2.09-1.92 (m, 2H), 1.84-1.19 (m, 6H), 1.10 (br d, J=6.3 Hz, 3H), 0.86 (s, 9H), 0.820 (s, 9H), 0.04 (s, 6H), −0.01 (s, 6H).

Synthesis of (2S,3R)-3-((tert-butyldimethylsilyl)oxy)-2-(7-((tert-butyldimethylsilyl)oxy)-1-oxo-2-azaspiro[3.5]nonan-2-yl)butanamide (7)

To a stirred solution of DIAD (1.65 mL, 8.34 mmol) in THF (20 mL) was added TPP (2.2 mg, 8.34 mmol) at RT under nitrogen atmosphere and the reaction mixture was stirred for 10 minutes. Then added compound 6 (2.8 g, 5.53 mmol) in THF (5 mL) at RT and stirred for 6 h. After consumption of the starting material (by TLC), water (2 mL) was added to reaction mixture and concentrated under reduced pressure to obtain crude material which was purified by silica gel column chromatography eluting with 50% EtOAc/hexanes to afford compound 7 (1.2 g, 44%) as a solid.

$^1$H NMR (500 MHz, DMSO-d$_6$): δ 7.29 (s, 1H), 7.10 (s, 1H), 4.36-4.24 (m, 1H), 4.01 (d, J=3.5 Hz, 1H), 3.78 (br s, 1H), 3.46 (d, J=5.8 Hz, 1H), 3.20 (d, J=5.8 Hz, 1H), 1.97-1.89 (m, 2H), 1.69-1.45 (m, 6H), 1.09 (d, J=6.1 Hz, 3H), 0.84 (s, 9H), 0.82 (s, 9H), 0.03 (s, 6H), 0.00 (s, 6H).

Synthesis of (2S,3R)-3-hydroxy-2-(7-hydroxy-1-oxo-2-azaspiro[3.5]nonan-2-yl)butanamide (AM)

To a stirred solution of compound 7 (600 mg, 1.23 mmol) in methanol (10 mL) were added NIS (140 mg, 0.62 mmol) at RT and stirred for 3 days. After consumption of the starting material (by TLC), the reaction mixture was concentrated under reduced pressure and crude mixture was triturated with EtOAc/ether to afford AM (120 mg, 37%) as white solid.

$^1$H NMR (500 MHz, DMSO-d$_6$): δ 7.44 (br s, 1H), 7.05 (br s, 1H), 4.87 (br d, J=4.9 Hz, 1H), 4.42 (br s, 1H), 3.98-3.85 (m, 2H), 3.54 (br s, 1H), 3.24-3.15 (m, 2H), 1.94-1.80 (m, 2H), 1.66-1.39 (m, 6H), 1.05 (d, J=6.1 Hz, 3H).

LCMS (ESI): m/z 257.2 [M$^+$+1];
HPLC: 95.92%

Example 8—Synthesis of Compound AN

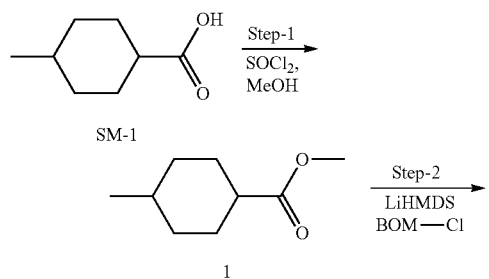

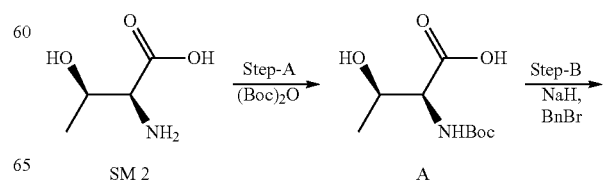

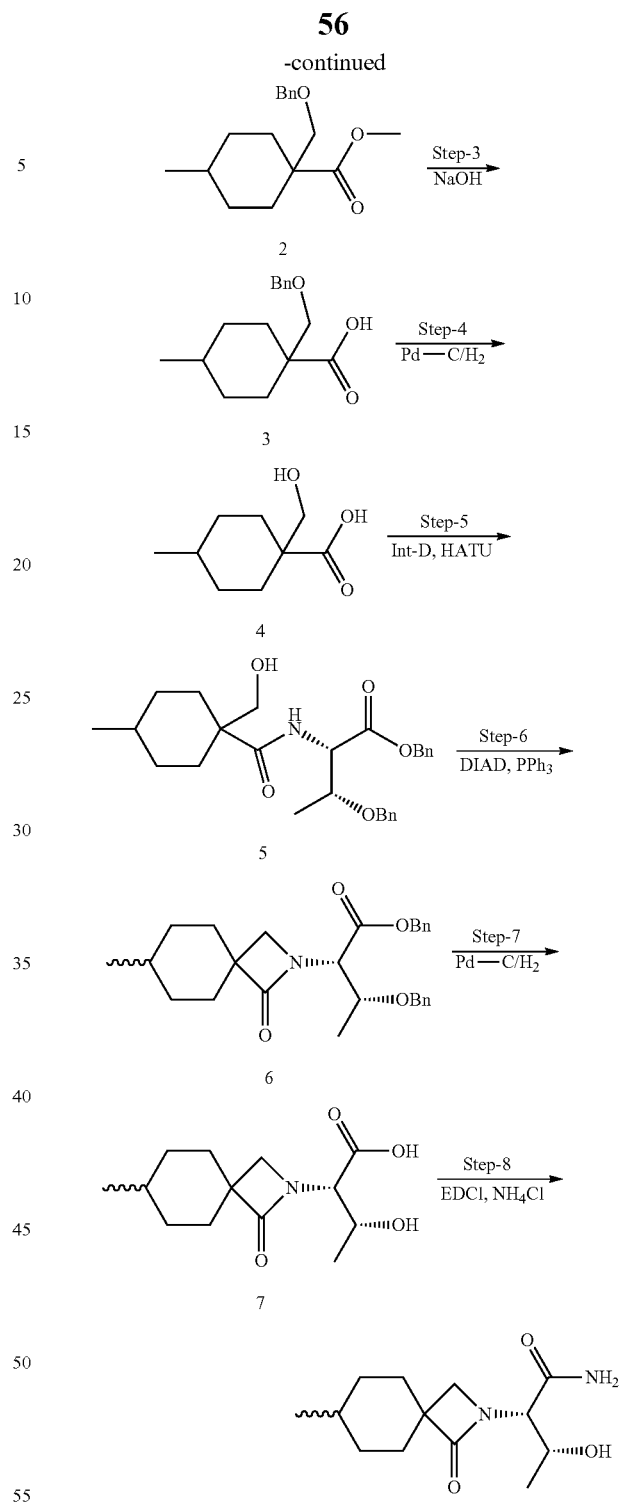

-continued

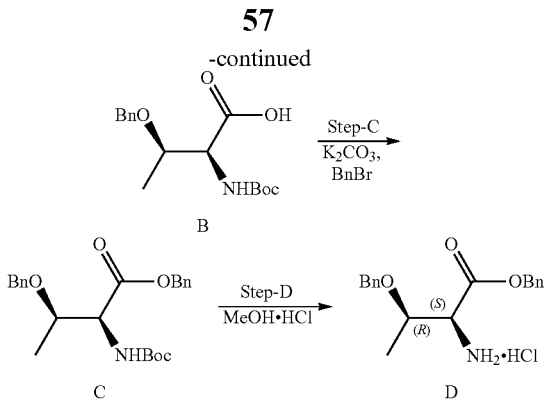

Synthesis of Methyl 4-methylcyclohexane-1-carboxylate (1)

To a solution of 4-methylcyclohexane-1-carboxylic acid (SM-1) (5 g, 35.1 mmol) in methanol Bui (1.6 (25 mL) was added thionyl chloride (5.1 mL, 70.3 mmol) at 0° C. under nitrogen atmosphere and then stirred for 16 h at room temperature. After consumption of the starting material (by TLC), volatiles were evaporated under reduced pressure. Crude mixture was diluted with EtOAc (20 mL) and washed with water (20 mL), saturated NaHCO$_3$ solution (20 mL) and brine solution (20 mL). Separated organic layer was dried over Na$_2$SO$_4$ and concentrated to obtain compound 1 (4.5 g, 83%) as colorless liquid.

$^1$H NMR: (400 MHz, DMSO-d$_6$): δ 3.57 (s, 3H), 2.24-2.18 (tt, J=3.6, 12.2 Hz, 1H), 1.89-1.81 (m, 2H), 1.72-1.64 (m, 2H), 1.38-1.24 (m, 3H), 0.98-0.88 (m, 2H), 0.85 (d, J=6.5 Hz, 3H).

LCMS (m/z): 157.12 [M$^+$+1]

Synthesis of Methyl 1-((benzyloxy)methyl)-4-methylcyclohexane-1-carboxylate (2)

To a stirring solution of diisopropyl amine (4.7 mL, 34.6 mmol) in THF (25 mL) was added n-BuLi (1.6 M in THF, 21 mL, 34.6 mmol) drop wise at −78° C. under nitrogen atmosphere. The reaction mixture was warmed to −40° C. and stirred for 1 h. Again cooled to −78° C., compound 1 (4.5 g, 28.8 mmol) was added and stirred for 1 h at same temperature. Then BOM-chloride (5.1 mL, 37.4 mmol) was added at −78° C. and stirred for 1 h. After consumption of the starting material (by TLC), the reaction was quenched with aqueous NH$_4$Cl solution (50 mL) and extracted with Et$_2$O (2×100 mL). Combined organic layers were washed with water (2×50 mL) followed by brine solution (2×50 mL). Organic layer was dried over Na$_2$SO$_4$ and concentrated to obtain crude compound which was purified by column chromatography by eluting with 5% EtOAc/hexanes to afford compound 2 (6.3 g, 79%) as syrup.

$^1$H NMR (400 MHz, DMSO-d$_6$): δ 7.37-7.31 (m, 3H), 7.30-7.22 (m, 2H), 4.42 (s, 2H), 3.60 (s, 3H), 3.35 (s, 2H), 2.09 (br d, J=13.1 Hz, 2H), 1.58-1.49 (m, 2H), 1.33-1.25 (m, 1H), 1.19 (dt, J=3.6, 13.3 Hz, 2H), 0.97-0.85 (m, 2H), 0.82 (d, J=6.5 Hz, 3H).

LCMS (ESI): m/z 277.0 [M$^+$+1]

Synthesis of 1-((benzyloxy)methyl)-4-methylcyclohexane-1-carboxylic acid (3)

To a stirring solution of compound 2 (6.3 g, 22.8 mmol) in MeOH:THF (40 mL, 1:1) was added NaOH solution (2.7 g in 20 mL H$_2$O) at RT. The reaction mixture was heated to 60° C. and stirred for 16 h. After consumption of the starting material (by TLC), volatiles were evaporated under reduced pressure and the crude was diluted with water (50 mL) and washed with Et$_2$O (2×50 mL). Aqueous layer was acidified using 6 N HCl solution (pH~2-3) and extracted with CH$_2$CL$_2$ (2×50 mL). Combined organic layers were dried over Na$_2$SO$_4$ and concentrated under reduced pressure to afford compound 3 (4.1 g, 69%) as syrup.

LCMS (ESI): m/z 261.16 [M$^+$−1]

Synthesis of 1-(hydroxymethyl)-4-methylcyclohexane-1-carboxylic acid (4)

To a stirring solution of compound 3 (5 g, 19.06 mmol) in methanol (50 mL) was added 50% wet 10% Pd/C (2.5 g) at RT under nitrogen atmosphere. The reaction mixture was stirred for 16 h at RT under H$_2$ atmosphere. After consumption of the starting material (by TLC), the reaction mixture was filtered through a pad of celite and the pad was washed with methanol (20 mL). Obtained filtrate was concentrated under reduced pressure to afford compound 4 (3 g, 91%) as white solid.

$^1$H NMR: (500 MHz, DMSO-d$_6$): δ 12.15 (br s, 1H), 4.84 (br s, 1H), 3.58 (s, 2H), 1.98 (br d, J=12.7 Hz, 2H), 1.52 (br d, J=10.7 Hz, 2H), 1.25 (ddd, J=3.8, 7.2, 10.7 Hz, 1H), 1.09 (dt, J=3.2, 13.2 Hz, 2H), 1.00-0.89 (m, 2H), 0.82 (d, J=6.4 Hz, 3H).

LCMS (ESI): m/z 173.22 [M$^+$+1]

Synthesis of benzyl O-benzyl-N-(1-(hydroxymethyl)-4-methylcyclohexane-1-carbonyl)-L-threoninate (5)

To a stirring solution of compound 4 (3 g, 17.4 mmol) in CH$_2$Cl$_2$ (30 mL) were added DIPEA (6.2 mL, 34.8 mmol), HATU (7.9 g, 20.8 mmol) and Int D (5.2 g, 17.4 mmol) at 0° C. under nitrogen atmosphere. The reaction mixture was brought to RT and stirred for 16 h. After consumption of the starting material (by TLC), the reaction mixture was quenched with water (20 mL) and extracted with CH$_2$Cl$_2$ (2×20 mL). Separated organic layer was washed with 2N HCl solution and brine solution. Organic layer was dried over anhydrous Na$_2$SO$_4$ and concentrated under reduced pressure to afford crude compound which was purified by column chromatography by eluting 20% EtOAc/n-hexane to obtain compound 5 (4.3 g, 54%) as thick syrup.

$^1$H NMR (500 MHz, DMSO-d$_6$): δ 7.34-7.17 (m, 10H), 5.10 (s, 2H), 5.01 (t, J=5.2 Hz, 1H), 4.58-4.47 (m, 2H), 4.32 (d, J=12.1 Hz, 1H), 4.09-4.06 (m, 1H), 3.29 (s, 1H), 2.01-1.96 (m, 2H), 1.49-1.42 (m, 2H), 1.24-1.21 (m, 1H), 1.19-1.07 (m, 7H), 0.76 (d, J=6.4 Hz, 3H).

LCMS (m/z): 454.58 [M$^+$+1]

Synthesis of benzyl (2S,3R)-3-(benzyloxy)-2-(7-methyl-1-oxo-2-azaspiro[3.5]nonan-2-yl)butanoate (6)

To a solution of TPP (3.2 g, 12.3 mmol) in THF (30 mL) was added DIAD (2.4 g, 12.3 mmol) at RT under nitrogen atmosphere and the reaction mixture was stirred for 10 min. The reaction mixture was cooled to 5° C. added compound 5 (4.3 g, 9.48 mmol) in THF (10 mL) at RT and stirred for 2 h. After consumption of the starting material (by TLC), the reaction mixture was quenched with ice and volatiles were concentrated under reduced pressure. Obtained crude material was purified by silica gel column chromatography eluting 10% EtOAc/hexane to afford compound 6 (1.6 g, 39%) as colorless thick syrup.

$^1$H NMR: (500 MHz, DMSO-$d_6$): δ 7.34-7.29 (m, 6H), 7.28-7.24 (m, 2H), 7.19 (d, J=6.9 Hz, 2H), 5.15 (q, J=12.4 Hz, 2H), 4.58-4.51 (m, 2H), 4.27 (d, J=11.9 Hz, 1H), 4.17 (dd, J=3.3, 6.2 Hz, 1H), 3.23 (d, J=5.5 Hz, 1H), 3.10 (d, J=5.8 Hz, 1H), 1.90-1.81 (m, 2H), 1.61-1.47 (m, 4H), 1.36-1.31 (m, 3H), 1.19 (d, J=6.4 Hz, 3H), 0.87 (d, J=4.6 Hz, 3H).

LCMS (ESI): m/z 436.5 (M$^+$+1]

Synthesis of (2S,3R)-3-hydroxy-2-(7-methyl-1-oxo-2-azaspiro[3.5]nonan-2-yl)butanoic acid (7)

To a stirring solution of compound 6 (1.6 g, 3.67 mmol) in methanol (50 mL) was added 50% wet 10% Pd/C (800 mg) at RT under nitrogen atmosphere. The reaction mixture was stirred for 16 h at RT under H$_2$ atmosphere (balloon atmosphere). After consumption of the starting material (by TLC), the reaction mixture was filtered through a pad of celite and the pad was washed with methanol (50 mL). Obtained filtrate was concentrated under reduced pressure and the product was triturated with diethyl ether to afford compound 7 (800 g, 85%) as white solid.

$^1$H NMR (500 MHz, DMSO-$d_6$): δ 4.21-4.15 (m, 1H), 4.04 (d, J=3.5 Hz, 1H), 3.25 (d, J=5.5 Hz, 1H), 3.18 (d, J=5.5 Hz, 1H), 1.94-1.85 (m, 2H), 1.63-1.52 (m, 4H), 1.38 (br s, 3H), 1.10 (d, J=6.4 Hz, 3H), 0.88 (d, J=4.6 Hz, 3H).

LCMS (m/z): 256.15 [M$^+$+1]

Synthesis of (2S,3R)-3-hydroxy-2-(7-methyl-1-oxo-2-azaspiro[3.5]nonan-2-yl)butanamide (AN)

To a stirring solution of compound 7 (500 mg, 1.96 mmol) in CH$_2$Cl$_2$ (10 mL) were added DIPEA (0.8 mL, 4.90 mmol), NH$_4$Cl (209 mg, 3.92 mmol) and HATU (894 mg, 2.35 mmol) at 0° C. under nitrogen atmosphere. The reaction mixture was stirred at RT for 16 h. After consumption of the starting material (by TLC), the reaction mixture was quenched with water (20 mL) and extracted with CH$_2$Cl$_2$ (2×30 mL). The combined organic layer was washed with brine solution, dried over anhydrous Na$_2$SO$_4$, filtered and concentrated under reduced pressure.

Obtained crude material was purified by silica gel column chromatography eluting 5% MeOH/CH$_2$CL$_2$ to afford racemic compound AN (180 mg, 36%) as white solid.

$^1$H NMR (500 MHz, DMSO-$d_6$): δ 7.46 (br s, 1H), 7.06 (br s, 1H), 4.87 (d, J=5.5 Hz, 1H), 3.98-3.86 (m, 2H), 3.20-3.13 (m, 2H), 1.94-1.83 (m, 2H), 1.59-1.48 (m, 4H), 1.39-1.34 (m, 3H), 1.07 (d, J=6.1 Hz, 3H), 0.88 (d, J=4.9 Hz, 3H).

LCMS (ESI): m/z 255.16 [M$^+$+1];
HPLC: 98.80%

Intermediate Synthesis

Synthesis of (2S,3R)-2-((tert-butoxycarbonyl) amino)-3-hydroxybutanoic acid (A)

To a stirring solution of SM-2 (300 g, 2.52 mol) in water (2 L) was added NaHCO$_3$ (801 g, 3.78 mol) portion wise at RT and stirred for 30 min. Then 1,4-Dioxane (1 L) was added and cooled to 0° C. Boc-anhydride (867 mL, 3.78 mol) was added drop wise to the reaction mixture and the stirring was continued at RT for 16 h. After consumption of the starting material (by TLC), the reaction mixture was concentrated under reduced pressure and obtained residue was diluted with water (200 mL) and acidified by using 4 N HCl (pH-2). The aqueous layer was extracted with EtOAc (2×300 mL). The combined organic layer was washed with brine (1×200 mL), dried over anhydrous Na$_2$SO$_4$, filtered and concentrated under reduced pressure to afford compound A (480 g, 86%) as thick syrup.

$^1$H-NMR (500 MHz, DMSO-$d_6$): δ 12.5 (br s, 1H), 6.30 (d, J=8.5 Hz, 1H), 4.50 (br s, 1H), 4.05-4.02 (m, 1H), 3.88-3.86 (m, 1H), 1.39 (s, 9H), 1.08 (d, J=6.0 Hz, 3H); LCMS (m/z): 218.1 [M$^+$–1]

Synthesis of (2S,3R)-3-(benzyloxy)-2-((tert-butoxycarbonyl) amino) butanoic acid (B)

To a stirring solution of compound A (250 g, 1.44 mol) in DMF (1 L) was added 60% NaH (68 g, 2.85 mol) portion wise at –20° C. under N$_2$ atmosphere and stirred for 2 h. To this added benzyl bromide (167 mL, 1.36 mol) drop wise and the reaction mixture was stirred at RT for 3 h. After consumption of the starting material (by TLC), the reaction mixture was quenched with ice cold water and washed with diethyl ether (2×250 mL). The separated aqueous layer was acidified using citric acid solution (pH~2) and extracted with EtOAc (2×300 mL). The combined organic layers were dried over anhydrous Na$_2$SO$_4$ and concentrated under reduced pressure to afford compound B (320 g, 90%) as thick syrup.

$^1$H-NMR (500 MHz, DMSO-$d_6$): δ 12.64 (br s, 1H), 7.34-7.25 (m, 5H), 6.46 (d, J=8.5 Hz, 1H), 4.53 (d, J=11.5 Hz, 1H), 4.39 (d, J=12.0 Hz, 1H), 4.00-3.98 (m, 2H), 1.39 (s, 9H), 1.15 (d, J=6.0 Hz, 3H);

Synthesis of (2S,3R)-benzyl 3-(benzyloxy)-2-((tert-butoxycarbonyl) amino) butanoate (C)

To a stirring solution of compound B (290 g, 0.93 mol) in DMF (1.4 L) was added K$_2$CO$_3$ (388 g, 2.81 mol) at 0° C. under N$_2$ atmosphere and stirred for 30 min. To this benzyl bromide (138 mL, 1.12 mol) was added drop wise at 0° C. and stirred at RT for 16 h. The reaction mixture was quenched with ice cold water and extracted with diethyl ether (2×250 mL). The separated organic layer was washed with brine, dried over anhydrous Na$_2$SO$_4$ and concentrated under reduced pressure. The crude material was purified by silica gel column chromatography eluting with 20% EtOAc/n-hexane to afford compound C (319 g, 85%) as thick syrup.

$^1$H-NMR (500 MHz, DMSO-$d_6$): δ 7.37-7.18 (m, 10H), 6.81 (d, J=9.0 Hz, 1H), 5.08 (s, 2H), 4.49 (d, J=12.0 Hz, 1H), 4.32 (d, J=12.0 Hz, 1H), 4.25-4.22 (m, 1H), 4.01-3.98 (m, 1H), 1.38 (s, 9H), 1.15 (d, J=6.0 Hz, 3H).

Mass (ESI): m/z 399.4 [M+];

Synthesis of (2S,3R)-benzyl 2-amino-3-(benzyloxy) butanoate (D)

To a stirring solution of compound C (290 g, 0.74 mol) in diethyl ether (500 mL) was added 2 M diethyl ether.HCl (1 L) at 0° C. and stirred at RT for 10 h. After consumption of the starting material (by TLC), the reaction mixture was concentrated under reduced pressure. The crude material was triturated with diethyl ether/n-pentane (100 mL/100 mL) and dried under reduced pressure to afford compound D (187 g, 86%) as white solid (HCl salt).

$^1$H-NMR (400 MHz, DMSO-$d_6$): δ 8.59 (s, 2H), 7.50-7.25 (m, 10H), 5.23 (d, J=12.5 Hz, 1H), 5.16 (d, J=12.5 Hz,

1H), 4.54 (d, J=12.0 Hz, 1H), 4.36 (d, J=12.0 Hz, 1H), 4.12-4.09 (m, 1H), 4.09-3.99 (m, 1H), 1.29 (d, J=6.5 Hz, 3H).

Mass (ESI): m/z 336.14 [M$^+$+1];

Example 9—Synthesis of Compound AO

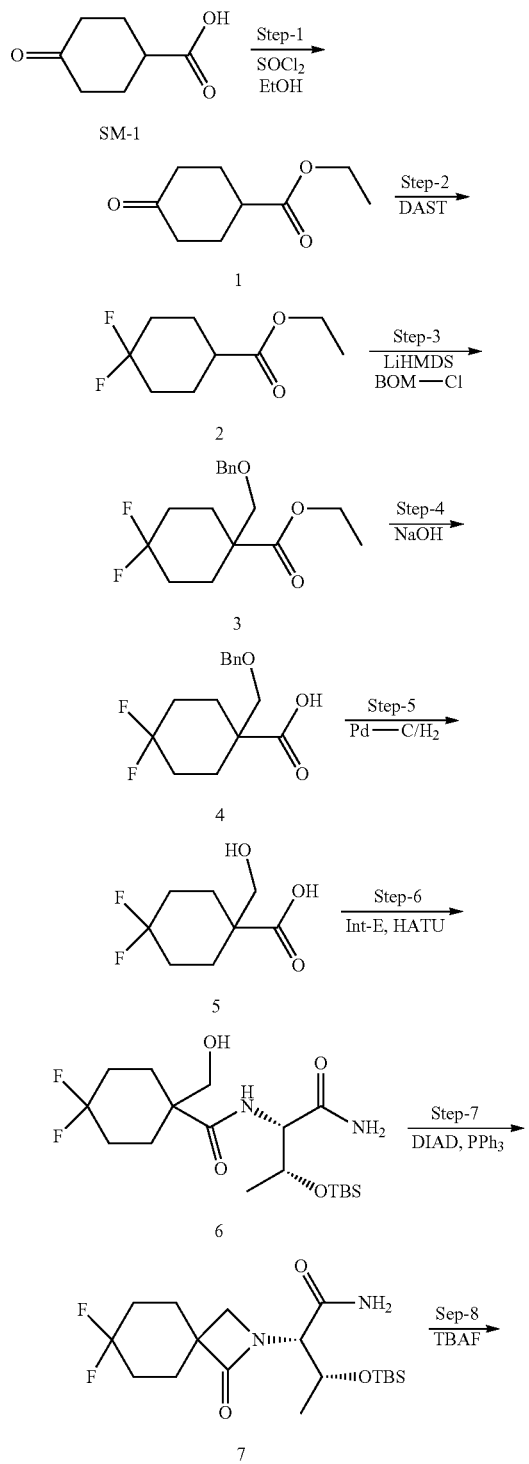

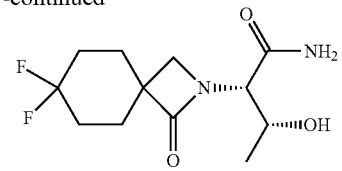

AO

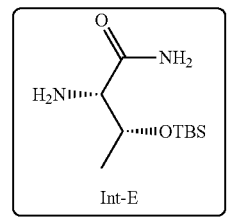

Int-E

Synthesis of ethyl 4-oxocyclohexane-1-carboxylate (1)

To a solution of 4-oxocyclohexane-1-carboxylic acid (SM-1) (1 g, 6.41 mmol) in ethanol (10 mL) was added thionyl chloride (0.56 mL, 7.69 mmol) drop wise at 0° C.; warmed to RT and stirred for 3 h. After consumption of the starting material (by TLC), volatiles were evaporated under reduced pressure. Obtained crude material was dissolved in EtOAc (20 mL) and washed with aqueous NaHCO$_3$ solution. Organic layer was dried over Na$_2$SO$_4$ and concentrated to obtain compound 1 (1 g, 84%) as brown liquid.

$^1$H NMR (500 MHz, CDCl$_3$): δ 4.16 (q, J=7.0 Hz, 2H), 2.77-2.70 (m, 1H), 2.50-2.43 (m, 2H), 2.38-2.30 (m, 2H), 2.23-2.16 (m, 2H), 2.05-1.95 (m, 2H), 1.26 (t, J=7.1 Hz, 3H).

LCMS (m/z): 171.3 [M$^+$+1]

Synthesis of ethyl 4,4-difluorocyclohexane-1-carboxylate (2)

To a solution of compound 1 (3 g, 17.6 mmol) in carbon tetrachloride (45 mL) was added DAST (4.6 mL, 35.2 mmol) drop wise at 0° C. and then stirred at RT for 5 h. After consumption of the starting material (by TLC), reaction mixture was quenched with ice water at 0° C. and extracted with Et$_2$O (2×50 mL). Organic layer was dried over Na$_2$SO$_4$ and concentrated to obtain compound 2 (2.8 g, crude), which was taken to next step without any further purification.

$^1$H NMR (500 MHz, CDCl$_3$): δ 4.16 (q, J=7.2 Hz, 2H), 2.56-2.46 (m, 1H), 2.44-2.19 (m, 2H), 2.15-2.05 (m, 2H), 2.04-1.96 (m, 1H), 1.92-1.71 (m, 3H), 1.27 (t, J=7.1 Hz, 3H).

LCMS (m/z): 192.1 [M$^+$+1]

Synthesis of ethyl 1-((benzyloxy)methyl)-4,4-difluorocyclohexane-1-carboxylate (3)

To a stirring solution of crude compound 2 (2.8 g, 14.5 mmol) in THF (50 mL) was added LiHMDS (1M in THF) (21.8 mL, 21.8 mmol) at −78° C. and stirred for 1 h. To this, BOM-chloride (2.42 mL, 17.4 mmol) was added drop wise at −78° C.; warmed to RT and stirred at RT for 4 h. After consumption of the starting material (by TLC), the reaction was quenched with NH$_4$Cl solution (50 mL) and extracted with EtOAc (2×100 mL). The combined organic layer dried over Na$_2$SO$_4$ and concentrated to obtain compound 3 (2.5 g, 55%) as colorless liquid.

¹H NMR (500 MHz, CDCl₃) δ 7.40-7.21 (m, 5H), 4.49 (s, 2H), 4.22-4.09 (m, 2H), 3.52 (s, 1H), 3.45 (s, 1H), 2.33-2.21 (m, 2H), 2.19-1.93 (m, 2H), 1.93-1.77 (m, 2H), 1.63-1.51 (m, 2H), 1.27 (t, J=7.1 Hz, 3H).

LCMS (m/z): 313.2 [M⁺+1]

Synthesis of 1-((benzyloxy)methyl)-4,4-difluorocyclohexane-1-carboxylic acid (4)

To a solution of compound 3 (2.5 g, 8.01 mmol) in MeOH:THF:H₂O (13 mL, 5:3:5) was added NaOH (1.6 g, 40.06 mmol) and stirred at RT for 10 min. The reaction mixture was heated to 70° C. and stirred for 3 h. After consumption of the starting material (by TLC), reaction mixture was brought to RT, volatiles were evaporated. Crude material was diluted with water (20 mL) and extracted with Et₂O (2×50 mL). The separated aqueous layer was acidified using 1N HCl solution (pH~3) and extracted with EtOAc (2×50 mL). Combined organic layers were dried over Na₂SO₄ and concentrated to afford compound 4 (2 g, 88%) as colorless liquid.

¹H NMR (500 MHz, DMSO-d₆): δ 12.58 (br s, 1H), 7.34-7.25 (m, 5H), 4.45 (s, 2H), 3.47 (s, 2H), 2.23-2.09 (m, 1H), 2.08-1.88 (m, 4H), 1.88-1.68 (m, 2H), 1.55-1.46 (m, 1H).

LCMS (ESI): m/z 284.1 [(M⁺+1)

Synthesis of 4,4-difluoro-1-(hydroxymethyl)cyclohexane-1-carboxylic acid (5)

To a stirring solution of compound 4 (2 g, 7.04 mmol) in methanol (80 mL) was added 50% wet 10% Pd—C (600 mg) at RT and stirred for 5 h under H₂ atmosphere (balloon pressure).

After consumption of the starting material (by TLC), the reaction mixture was filtered through a pad of celite and the pad was washed with CH₃OH (25 mL). Obtained filtrate was concentrated under reduced pressure to afford compound 5 (1.2 g, 88%) as colorless liquid.

¹H NMR (500 MHz, DMSO-d₆-D₂O Exc): δ 3.42-3.30 (m, 2H), 1.97-1.88 (m, 3H), 1.87-1.65 (m, 2H), 1.46-1.36 (m, 2H), 1.26-1.16 (m, 1H).

Synthesis of N-((2S,3R)-1-amino-3-((tert-butyldimethylsilyl)oxy)-1-oxobutan-2-yl)-4,4-difluoro-1-(hydroxymethyl)cyclohexane-1-carboxamide (6)

To a stirring solution of compound 5 (1.2 g, 6.18 mmol) and Int-E (1.7 g, 7.42 mmol) in CH₂CL₂ (60 mL) were added diisopropylethylamine (3.4 mL, 18.5 mmol) and HATU (3.5 g, 9.27 mmol) at 0° C. under nitrogen atmosphere. The reaction mixture was brought to RT and stirred for 16 h. After consumption of the starting material (by TLC), the reaction mixture was diluted with water (20 mL) and extracted with CH₂Cl₂ (2×40 mL). Organic layer was washed with 5% citric acid solution. Organic layer was dried over anhydrous Na₂SO₄ and concentrated under reduced pressure to afford crude compound which was purified by column chromatography by eluting with 10% MeOH/CH₂CL₂ to obtain compound 6 (1.8 g, 72%) off-white solid.

¹H NMR (500 MHz, DMSO-d₆): δ 7.29-7.09 (m, 3H), 5.52 (t, J=5.2 Hz, 1H), 4.33 (dd, J=1.7, 6.4 Hz, 1H), 4.13 (dd, J=1.7, 8.7 Hz, 1H), 3.50-3.38 (m, 2H), 2.06-1.75 (m, 6H), 1.59-1.54 (m, 1H), 1.48-1.35 (m, 1H), 1.07 (d, J=6.1 Hz, 3H), 0.84 (s, 9H), 0.03 (s, 3H), 0.01 (s, 3H).

LCMS (m/z): 409.4 [M⁺+1]

Synthesis of (2S,3R)-3-((tert-butyldimethylsilyl)oxy)-2-(7,7-difluoro-1-oxo-2-azaspiro[3.5]nonan-2-yl)butanamide (7)

To a solution of triphenylphosphine (1.7 g, 6.61 mmol) in THF (50 mL) was added DIAD (1.3 mL, 6.61 mmol) drop wise at RT under nitrogen atmosphere and stirred for 5 minutes. To this, compound 6 (1.8 g, 4.41 mmol) in THF (20 mL) solution was added drop wise and allowed to stir RT for 4 h. After consumption of the starting material (by TLC), volatiles were evaporated under reduced pressure. Obtained crude material was purified by silica gel column chromatography eluting with 70% EtOAc/hexanes to afford compound 7 (1.2 g, 70%) off-white solid.

¹H NMR (400 MHz, DMSO-d₆): δ 7.34 (s, 1H), 7.17 (s, 1H), 4.36 (br dd, J=3.5, 6.2 Hz, 1H), 4.05 (d, J=3.4 Hz, 1H), 3.57 (d, J=6.2 Hz, 1H), 2.17-1.79 (m, 8H), 1.26-1.07 (m, 4H), 0.84 (s, 9H), 0.05 (s, 3H), 0.03 (s, 3H).

LCMS (ESI): m/z 391 [M⁺+1]

Synthesis of (2S,3R)-2-(7,7-difluoro-1-oxo-2-azaspiro[3.5]nonan-2-yl)-3-hydroxybutanamide (AO)

To a stirring solution of compound 7 (500 mg, 1.28 mmol) and CsF (195 mg, 1.28 mmol) in THF (5 mL) was added TBAF (1M in THF) (0.12 mL, 0.128 mmol) at RT under nitrogen atmosphere. The reaction mixture was stirred for at RT for 16 h. volatiles were evaporated under reduced pressure. Obtained crude material was purified by silica gel column chromatography eluting with 5% MeOH/CH₂Cl₂ followed by preparative HPLC purification to afford AO (70 mg, 20%) as thick syrup.

¹H-NMR: (400 MHz, CD₃OD): δ 4.18-4.07 (m, 2H), 4.45-4.39 (m, 2H), 2.18-2.09 (m, 2H), 2.03-1.87 (m, 6H), 1.24 (t, J=6.8 Hz, 3H).

LCMS (M/Z) m/z: 277.13 [M⁺+1]
HPLC: 99.0%

Synthesis of (2S,3R)-2-amino-3-((tert-butyldimethylsilyl)oxy)butanamide (Int-E)

To a stirring solution of (2S,3R)-2-amino-3-hydroxybutanamide (7 g, 0.593 mmol) in NMP (70 mL) was added and TEA (12 g, 0.118 mmol) and TBS-C₁ (13.34 g, 0.0889 moles) at 0° C. and stirred for 16 h. After consumption of the starting material (by TLC), reaction mixture was diluted with water and extracted with EtOAc, RM was evaporated on reduced pressure and which was purified by column chromatography by eluting with 30% EtOAc/hexanes to afford compound Int-E (5.9 g, 42.8%) as off white solid.

Mass (ESI): m/z 234.2 [M⁺+1]

Example 10—Synthesis of Compounds AP and AO

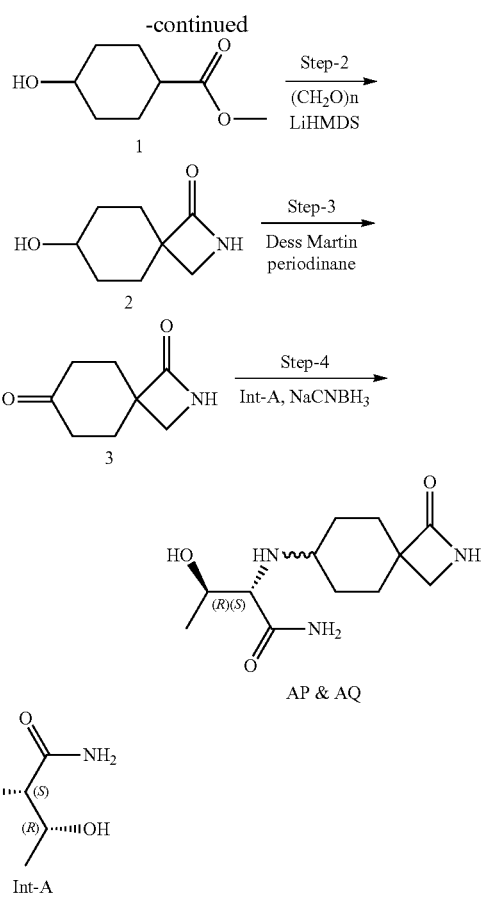

Synthesis of methyl 4-hydroxycyclohexane-1-carboxylate (1)

To a stirred suspension of 4-hydroxycyclohexane-1-carboxylic acid (SM) (25 g, 0.173 mol) in methanol (100 mL) was added sulfuric acid (1.5 mL, 0.26 mol) drop wise at room temperature. The reaction mixture was stirred at room temperature for 16 h. After consumption of the starting material (by TLC), reaction was quenched with water (100 mL) and extracted with EtOAc (3×100 mL). Combined organic layer was washed with saturated NaHCO$_3$ solution and brine solution. Organic layer was dried over Na$_2$SO$_4$ and concentrated under reduced pressure to afford compound 1 (20 g, 73%) as liquid.

$^1$H NMR (500 MHz, DMSO-d$_6$): δ 4.38 (d, J=3.5 Hz, 1H), 3.65 (br d, J=3.5 Hz, 1H), 3.59 (s, 3H), 2.40-2.32 (m, 1H), 1.88-1.74 (m, 4H), 1.55-1.44 (m, 2H), 1.39-1.28 (m, 1H), 1.20-1.09 (m, 1H).

LCMS (m/z): 159.20 [M$^+$+1]

Synthesis of 7-hydroxy-2-azaspiro[3.5]nonan-1-one (2)

To a stirring solution of compound 1 (10 g, 0.063 mol) in dry THF (100 mL) were added paraformaldehyde (2 g, 0.063 mol) and LiHMDS (1.0 M in THF) (190 mL, 0.189 mol) at −50° C. under nitrogen atmosphere. The reaction mixture warmed to RT and stirred for 16 h. After consumption of the starting material (by TLC), the reaction was quenched with ice water (50 mL) and extracted with EtOAc (3×100 mL). The combined organic layer was washed with brine solution (2×10 mL), dried over Na$_2$SO$_4$ and concentrated to obtain crude compound which was purified by column chromatography by eluting with 5% MeOH/CH$_2$Cl$_2$ followed by combiflash chromatography to afford compound 2 (3.7 g, 37%) as an off white solid.

$^1$H NMR (400 MHz, DMSO-d$_6$): δ 7.61 (br s, 1H), 4.46-4.42 (m, 1H), 3.59-3.53 (m, 1H), 2.91 (s, 2H), 1.69-1.42 (m, 8H).

LCMS (ESI): m/z 156.20 [M$^+$+1];

Synthesis of 2-azaspiro[3.5]nonane-1,7-dione (3)

To a stirring solution of compound 2 (3.7 g, 0.023 mol) in CH$_2$CL$_2$ (100 mL) was added Dess-Martin Periodinane (12.14 g, 0.028 mol) portion wise at 0° C. under nitrogen atmosphere. The resultant reaction mixture was stirred at room temperature for 4 h. After consumption of the starting material (by TLC), the reaction mixture was diluted with water (50 mL) and extracted with CH$_2$CL$_2$ (2×50 mL). Separated organic layer was washed with saturated NaHCO$_3$ solution (20 mL) and brine solution. Organic layer was dried over Na$_2$SO$_4$ and concentrated to obtain crude compound which was purified by column chromatography by eluting with 5% MeOH/CH$_2$CL$_2$ followed by Combiflash chromatography to afford compound 3 (1.2 g, 33%) as liquid.

$^1$H NMR (400 MHz, DMSO-d$_6$): δ 7.85 (br s, 1H), 3.17 (s, 2H), 2.45-2.31 (m, 4H), 2.05-1.96 (m, 4H).

LCMS (ESI): m/z 153.38 [M$^+$+1];

Synthesis of (2S,3R)-3-hydroxy-2-((1-oxo-2-azaspiro[3.5]nonan-7-yl)amino)butanamide (AP and AQ)

To a stirring mixture of compound 3 (700 mg, 4.57 mmol) and Int-A (650 mg, 5.49 mmol) in methanol (20 mL) were added NaCNBH$_3$ (574 mg, 9.15 mmol) and AcOH (cat.) (0.01 mL) at 0° C. under nitrogen atmosphere. The resultant reaction mixture was stirred at room temperature for 24 h. After consumption of the starting material (by TLC), reaction mixture was concentrated under reduced pressure to obtain crude which was purified by reverse phase column chromatography followed by chiral column chromatography to afford AP (134 mg, 11%) and AQ (115 mg, 10%) as white solids.

AP:

$^1$H NMR (400 MHz, DMSO-d$_6$): δ 7.66 (s, 1H), 7.27 (br d, J=2.4 Hz, 1H), 7.02 (br d, J=2.0 Hz, 1H), 4.53 (br s, 1H), 3.60 (t, J=5.8 Hz, 1H), 2.98 (s, 2H), 2.83 (d, J=5.9 Hz, 1H), 2.34-2.25 (m, 1H), 1.90-1.84 (m, 1H), 1.81-1.66 (m, 3H), 1.53-1.43 (m, 2H), 1.16-0.93 (m, 5H).

LCMS (ESI): m/z 256.2 [M$^+$+1];

HPLC: 96.93%

Chiral HPLC: 99.02%

AQ:

$^1$H NMR (500 MHz, DMSO-d$_6$): δ 7.60 (s, 1H), 7.26 (s, 1H), 7.01 (s, 1H), 4.56 (br s, 1H), 3.61 (t, J=6.1 Hz, 1H), 2.90 (s, 2H), 2.81 (d, J=6.1 Hz, 1H), 2.42-2.37 (m, 1H), 1.92-1.86 (m, 2H), 1.68-1.44 (m, 6H), 1.06 (d, J=6.4 Hz, 3H).

LCMS (ESI): m/z 256.2 [M$^+$+1];

HPLC: 91.06%

Chiral HPLC: 98.18%.

Example 11—Synthesis of Compounds AS and AT

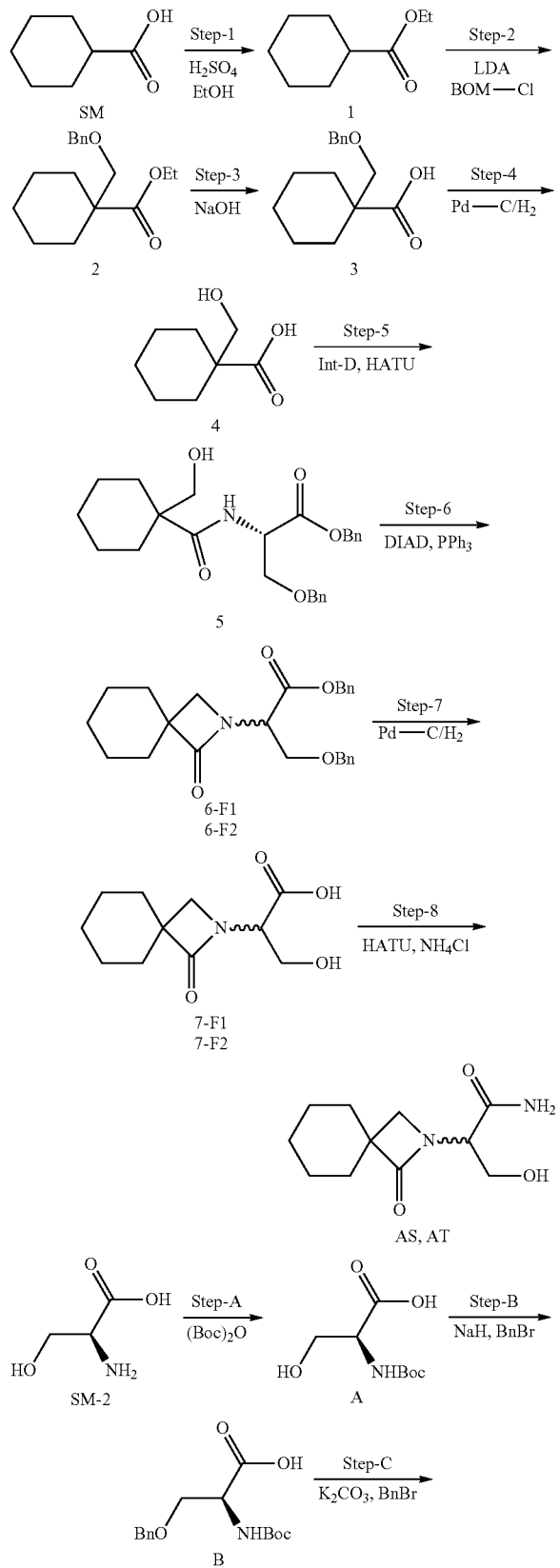

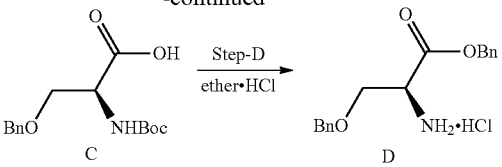

Synthesis of ethyl cyclohexanecarboxylate (1)

To a solution of cyclohexanecarboxylic acid (SM, 50 g, 390.6 mmol) in ethanol (500 mL) was added sulfuric acid (38 g, 390.6 mmol) drop wise at 0° C. under nitrogen atmosphere. The reaction mixture was heated to 80° C. and stirred for 16 h. After consumption of the starting material (by TLC), reaction was brought to RT and volatiles were concentrated under reduced pressure. Crude mixture was diluted with EtOAc (500 mL) and washed with water (2×500 mL), aqueous NaHCO$_3$ solution (200 mL) and brine solution (200 mL). The organic layer was dried over Na$_2$SO$_4$ and concentrated under reduced pressure to obtain compound 1 (41 g, 67%) as a colorless liquid.

$^1$H-NMR: (500 MHz, DMSO-d$_6$): δ 4.03 (q, J=7.5 Hz, 2H), 2.29-2.24 (m, 1H), 1.81-1.78 (m, 2H), 1.67-1.56 (m, 3H), 1.37-1.16 (m, 8H).

LCMS (ESI): m/z 198.0 [(M$^+$+1+ACN)]

Synthesis of ethyl 1-((benzyloxy)methyl)cyclohexane-1-carboxylate (2)

To a stirring solution of diisopropyl amine (53.9 mL, 394.2 mmol) in THF (200 mL) was added n-BuLi (1M in THF, 394 mL, 394.2 mmol) drop wise at −78° C. under nitrogen atmosphere. The reaction mixture was warmed to −50° C. and stirred for 30 minutes. Again cooled to −78° C., compound 1 (41 g, 262.8 mmol) in THF (210 mL) was added and stirred for 30 minutes. Then BOM-chloride (54.8 mL, 394.2 mmol) was added, warmed to −50° C. and stirred for 30 minutes. After consumption of the starting material (by TLC), reaction was quenched with aqueous NH$_4$Cl (200 mL) and extracted with EtOAc (2×500 mL). The combined organic layer was washed with water (200 mL) followed by brine solution (200 mL), dried over Na$_2$SO$_4$ and concentrated under reduced pressure to obtain crude compound which was purified by column chromatography by eluting 10% EtOAc/n-hexane to afford compound 2 (70 g, crude) as a brown color syrup.

$^1$H-NMR: (400 MHz, DMSO-d$_6$): δ 7.37-7.24 (m, 5H), 4.42 (s, 2H), 4.09-4.02 (m, 2H), 3.40 (s, 2H), 1.98-1.92 (m, 2H), 1.48 (s, 2H), 1.30-1.12 (m, 9H).

LCMS (ESI): m/z 277.4 [M$^+$+1]

Synthesis of 1-((benzyloxy)methyl)cyclohexane-1-carboxylic acid (3)

To a stirring solution of crude compound 2 (70 g, 253.6 mmol) in EtOH (70 mL):THF (240 mL) was added NaOH solution (50.7 g, 1268.1 mmol) in H$_2$O (70 mL) at 0° C. The reaction mixture was heated to 70° C. and stirred for 16 h. After consumption of the starting material (by TLC), volatiles were evaporated under reduced pressure and the crude was diluted with water (500 mL) and washed with Et$_2$O (2×200 mL). Aqueous layer was acidified using 2N HCl solution (pH~2-3) and extracted with EtOAc (2×500 mL). The combined organic layer was dried over Na$_2$SO$_4$ and concentrated under reduced pressure to obtain compound 3 (92 g, crude) as a thick syrup.

$^1$H-NMR: (500 MHz, DMSO-d$_6$): δ 12.09 (s, 1H), 7.28-7.21 (m, 5H), 4.43 (s, 2H), 3.42 (s, 2H), 1.90-1.87 (m, 2H), 1.53-1.45 (m, 3H), 1.31-1.17 (m, 5H).

LCMS (ESI): m/z 247.0 [M$^+$−1]

Synthesis of
1-(hydroxymethyl)cyclohexane-1-carboxylic acid
(4)

To a stirring solution of crude compound 3 (12 g, 48.3 mmol) in MeOH (240 mL) was added 10% Pd/C (50% wet, 6 g) at RT and stirred for 12 h under H$_2$ atmosphere. After consumption of the starting material (by TLC), the reaction mixture was filtered through a pad of celite and the pad was washed with MeOH (100 mL). Obtained filtrate was concentrated under reduced pressure to obtain crude which was triturated with pentane to afford compound 4 (6 g, 78%) as an off-white solid.

$^1$H-NMR: (500 MHz, DMSO-d$_6$): δ 11.93 (s, 1H), 4.62 (s, 1H), 3.35 (s, 1H), 1.86-1.81 (m, 2H), 1.46-1.41 (m, 3H), 1.27-1.20 (m, 2H), 1.18-1.07 (m, 3H).

LCMS (ESI): m/z 157.0 [M$^+$−1]

Synthesis of benzyl O-benzyl-N-(1-(hydroxymethyl)cyclohexane-1-carbonyl)-L-serinate (5)

To a stirring solution of compound 4 (10 g, 63.2 mmol) in DCM (200 mL) were added DIPEA (16.5 mL, 94.9 mmol), HATU (36 g, 94.9 mmol) and benzyl O-benzyl-L-serinate hydrochloride (D, 20 g, 63.2 mmol) at 0° C. under nitrogen atmosphere. The reaction mixture was brought to RT and stirred for 16 h. After consumption of the starting material (by TLC), reaction mixture was diluted with water (100 mL) and extracted with DCM (2×100 mL). The organic layer was dried over anhydrous Na$_2$SO$_4$ and concentrated under reduced pressure to afford crude compound which was purified by column chromatography by eluting 40% EtOAc/n-hexane to obtain compound 5 (19 g, 70%) as a thick syrup.

$^1$H-NMR: (400 MHz, DMSO-d$_6$): δ 7.81-7.76 (m, 1H), 7.34-7.5.23 (m, 10H), 5.17-5.08 (m, 2H), 4.93-4.88 (m, 1H), 4.66-4.57 (m, 1H), 4.46 (s, 2H), 4.82-4.76 (m, 1H), 4.68-4.66 (m, 1H), 3.36-3.32 (m, 2H), 1.86-1.79 (m, 2H), 1.37-1.23 (m, 8H).

LCMS (m/z): 424.5 [M$^+$−1]

Synthesis of benzyl 3-(benzyloxy)-2-(1-oxo-2-azaspiro[3.5]nonan-2-yl)propanoate (6-F1 and 6-F2)

To a solution of Ph$_3$P (17.1 g, 65.2 mmol) in THF (150 mL) was added DIAD (12.82 mL, 65.2 mmol) at RT under nitrogen atmosphere and the reaction mixture was stirred for 20 minutes. The reaction mixture was cooled to 0° C., compound 5 (18.5 g, 43.5 mmol) in THF (30 mL) and allowed to stir at RT for 4 h. After consumption of the starting material (by TLC), reaction mixture was concentrated under reduced pressure. Obtained crude material was purified by silica gel column chromatography by eluting with 10% EtOAc/hexane to afford compound 6-F$_1$ and 6-F2 as mixture (15 g, 84%) as a thick syrup.

$^1$H-NMR: (500 MHz, DMSO-d$_6$): δ 7.36-7.5.22 (m, 10H), 5.18 (s, 2H), 4.67-4.62 (m, 1H), 4.56-4.42 (m, 2H), 3.87-4.76 (m, 2H), 3.14-3.07 (m, 2H), 1.85-1.76 (m, 6H), 1.44-1.37 (m, 1H), 1.29-1.07 (m, 3H).

LCMS (ESI): m/z 430.1 [M$^+$+Na]

Synthesis of 3-hydroxy-2-(1-oxo-2-azaspiro[3.5]nonan-2-yl)propanoic acid (7-F1 and 7-F2)

To a stirring solution of compound 6-F1 and 6-F2 (15 g, 36.8 mmol) in MeOH (150 mL) was added 10% Pd/C (50% wet, 7.5 g) at RT and stirred for 16 h under H$_2$ atmosphere. After consumption of the starting material (by TLC), the reaction mixture was filtered through a pad of celite and the pad was washed with MeOH (500 mL). Obtained filtrate was concentrated under reduced pressure to obtain crude which was triturated with pentane to afford compound 7-F1 and 7-F2 (9 g, crude) as a white solid.

$^1$H-NMR: (500 MHz, DMSO-d$_6$): δ 12.83 (br s, 1H), 5.07 (br s, 1H), 4.24-4.18 (m, 1H), 3.73-3.67 (m, 2H), 3.17 (s, 2H), 1.77-1.64 (m, 6H), 1.47-1.43 (m, 1H), 1.25-1.16 (m, 3H).

LCMS: (m/z) 228.2 [M$^+$+1]

Synthesis of 3-hydroxy-2-(1-oxo-2-azaspiro[3.5]nonan-2-yl)propanamide (AS and AT)

To a stirring solution of crude compound 7-F1 and 7-F2 (5 g, 22.0 mmol) in DMF (25 mL) was added HATU (12.5 g, 33.0 mmol) at 0° C. under nitrogen atmosphere. After stirring for 10 minutes, DIPEA (11.5 mL, 66.0 mmol) and NH$_4$Cl (2.94 g, 55.0 mmol) were added. The reaction mixture was allowed to stir at RT for 16 h. After consumption of the starting material (by TLC), the reaction mixture was diluted with ice water (100 mL) and extracted with EtOAc (2×100 mL). The combined organic layer was dried over anhydrous Na$_2$SO$_4$, filtered and concentrated under reduced pressure. Obtained crude material was purified by silica gel column chromatography using 5% MeOH/DCM to afford racemic AS and AT (2 g) as brown color syrup which was purified first by reverse phase purification followed by chiral preparative HPLC purification to afford AS (210 mg) and AT (190 mg) as white solid.

AS $^1$H-NMR: (400 MHz, D$_2$O): δ 4.34-4.26 (m, 1H), 3.91-3.88 (m, 2H), 3.29 (s, 2H), 1.68-1.55 (m, 6H), 1.49-1.42 (m, 1H), 1.28-1.15 (m, 3H).

LCMS (ESI): m/z 227.0 [M$^+$+1]
HPLC: 99.03%
Chiral HPLC: >99%
SOR: −8.25 (C=0.5% in MeOH)

AT $^1$H-NMR: (400 MHz, D$_2$O): δ 4.45-4.36 (m, 1H), 4.03-3.90 (m, 2H), 3.42 (s, 2H), 1.78-1.67 (m, 6H), 1.59-1.53 (m, 1H), 1.43-1.26 (m, 3H).

LCMS (ESI): m/z 227.0 [M$^+$+1]
HPLC: 99.15%
Chiral HPLC: 97.39%
SOR: +12.96 (c=0.5% in MeOH).

Example 12—Synthesis of Compound BC

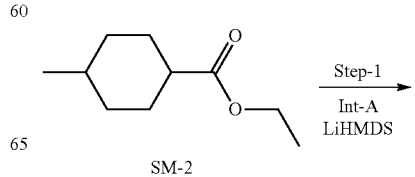

71

-continued

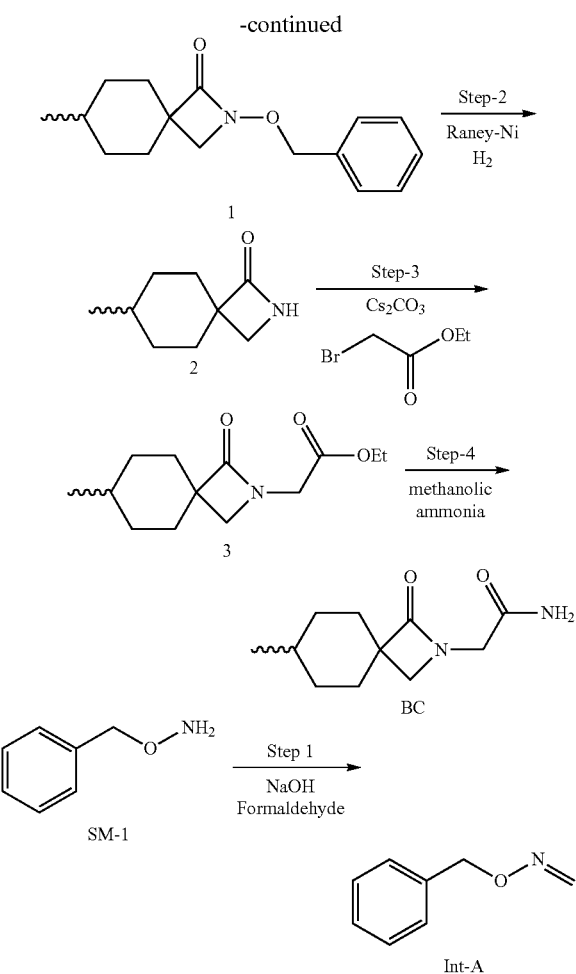

Synthesis of formaldehyde O-benzyl oxime (Int-A)

To a solution of SM-1 (15.0 g, 94.0 mmol) in H$_2$O (150 mL), parafarmaldehyde (5.2 g, 180 mmol) was added and stirred at RT for 2 h. After consumption of the starting material (by TLC), the reaction mixture was diluted with water (50 mL) and extracted with EtOAc (2×250 mL). The combined organic layer was washed with brine (50 mL), dried over Na$_2$SO$_4$ and concentrated under reduced pressure to afford Int-A (12.0 g, 75%), which was used directly for next step without any purification.

Synthesis of 2-(benzyloxy)-7-methyl-2-azaspiro[3.5]nonan-1-one (1)

To a stirred solution of SM-2 (5.0 g, 32.0 mmol) in THF (50 mL), LiHMDS (1M solution in THF, 50 mL, 48.0 mmol) was added at −78° C. and stirred at room temperature for 30 min. Int-A (4.75 g, 35.0 mmol) was added to the reaction mixture at −50° C. and stirred at RT for 2 h. After consumption of the starting material (by TLC), the reaction mixture was quenched with saturated NH$_4$Cl solution (150 mL) and extracted with EtOAc (2×300 mL). The combined organic layer was washed with brine (50 mL), dried over Na$_2$SO$_4$ and concentrated under reduced pressure to afford 1 (2.2 g, 30%). The crude was used directly for next step without any purification.

LCMS (ESI): m/z 260 [M$^+$+1]

72

Synthesis of 7-methyl-2-azaspiro[3.5]nonan-1-one (2)

To a stirred solution of 1 (0.6 g, 2.30 mmol) in MeOH (15 mL), Raney Ni (0.7 g, 9.20 mmol) was added and reaction mixture was stirred at room temperature 12 h under H$_2$ atmosphere. After consumption of the starting material (by TLC), the reaction mixture was filtered through celite and washed with MeOH (20 mL). The filtrate was concentrated under reduced pressure and the residue was purified by column chromatography using 30% EtOAc/hexane to afford 2 (0.4 g, 42%).

LCMS (ESI): m/z 154 [M$^+$+1]

Synthesis of ethyl 2-(7-methyl-1-oxo-2-azaspiro[3.5]nonan-2-yl)acetate (3)

To a stirring solution of 2 (1.5 g, 9.40 mmol) in acetonitrile (10 mL) was added Cs$_2$CO$_3$ (3.8 g, 11.6 mmol) at 0° C. and added ethyl 2-bromoacetate (1.78 g, 10.7 mmol) slowly. The reaction mixture temperature was warmed to RT and stirred for 16 h. After consumption of the starting material (by TLC), the reaction mixture was filtered and filtrate was concentrated under reduced pressure to afford 3 (2.0 g, crude) as a syrup was used directly for next step without any purification.

Synthesis of 2-(7-methyl-1-oxo-2-azaspiro[3.5]nonan-2-yl)acetamide (BC)

To a stirred solution of compound 3 (2.0 g, 8.0 mmol) in MeOH (5 mL), ammonia gas was purged into it till saturation for about 20 min at 0° C. and stirred at RT for 10 h. After consumption of the starting material (by TLC), the reaction mixture was evaporated to give a residue. The residue was purified by flash column chromatography to afford BC (0.3 g, 17.8%) as a pale yellow solid.

$^1$H NMR (400 MHz, DMSO-d6) δ 7.39 (s, 1H), 7.08 (s, 1H), 3.66 (s, 2H), 3.00 (s, 2H), 1.91 (d, J=11.2, Hz, 2H), 1.55-1.53 (m, 4H), 1.37-1.35 (m, 3H), 0.85 (d, J=4.4, Hz, 3H).

LCMS (ESI): m/z 211 [M$^+$+1]

HPLC: 98.2%

Example 13—Synthesis of Compounds BE and BF

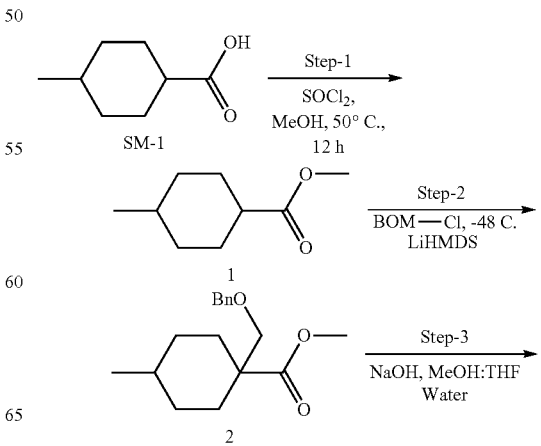

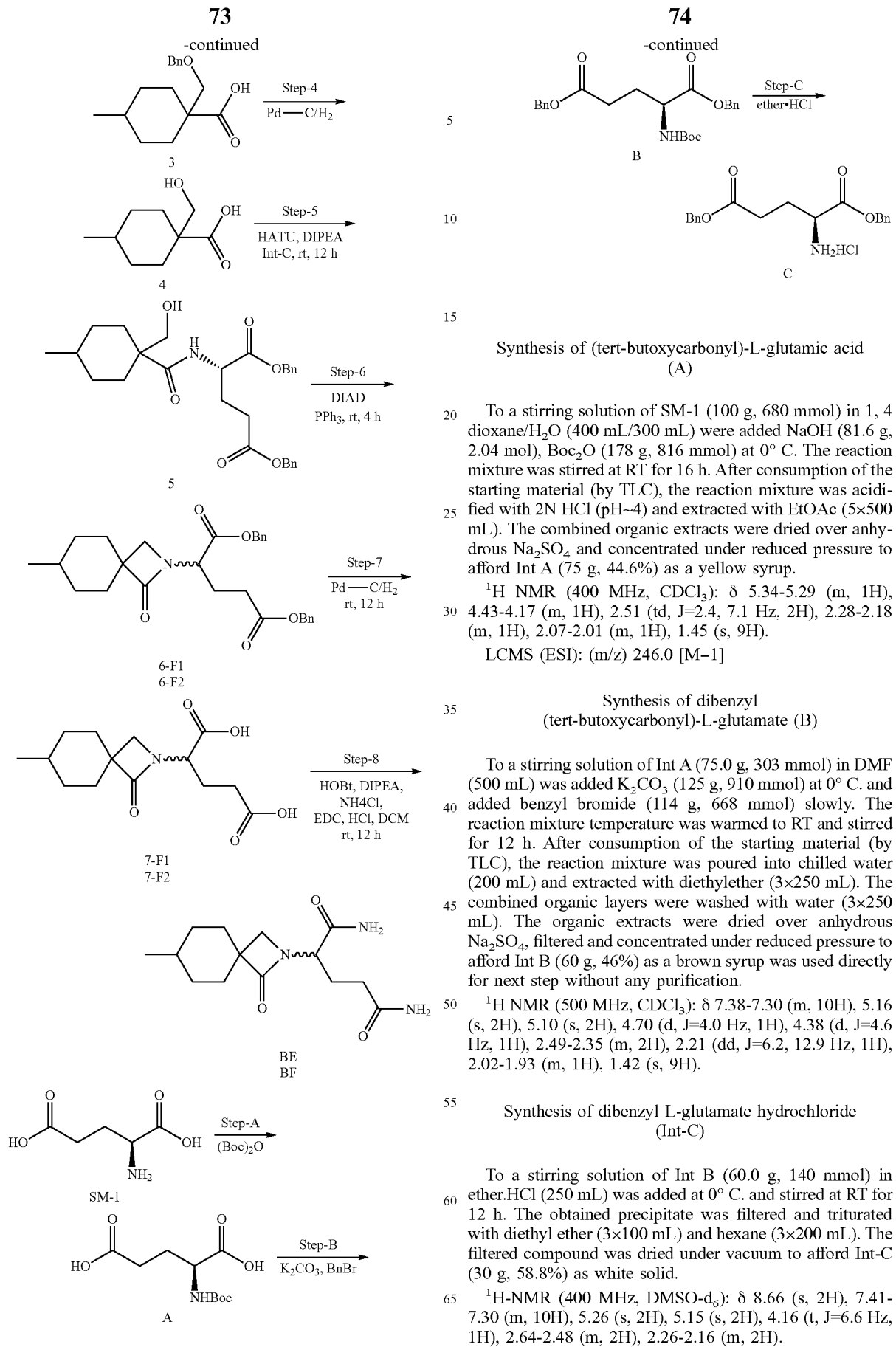

Synthesis of (tert-butoxycarbonyl)-L-glutamic acid (A)

To a stirring solution of SM-1 (100 g, 680 mmol) in 1, 4 dioxane/H₂O (400 mL/300 mL) were added NaOH (81.6 g, 2.04 mol), Boc₂O (178 g, 816 mmol) at 0° C. The reaction mixture was stirred at RT for 16 h. After consumption of the starting material (by TLC), the reaction mixture was acidified with 2N HCl (pH~4) and extracted with EtOAc (5×500 mL). The combined organic extracts were dried over anhydrous Na₂SO₄ and concentrated under reduced pressure to afford Int A (75 g, 44.6%) as a yellow syrup.

$^1$H NMR (400 MHz, CDCl₃): δ 5.34-5.29 (m, 1H), 4.43-4.17 (m, 1H), 2.51 (td, J=2.4, 7.1 Hz, 2H), 2.28-2.18 (m, 1H), 2.07-2.01 (m, 1H), 1.45 (s, 9H).

LCMS (ESI): (m/z) 246.0 [M−1]

Synthesis of dibenzyl (tert-butoxycarbonyl)-L-glutamate (B)

To a stirring solution of Int A (75.0 g, 303 mmol) in DMF (500 mL) was added K₂CO₃ (125 g, 910 mmol) at 0° C. and added benzyl bromide (114 g, 668 mmol) slowly. The reaction mixture temperature was warmed to RT and stirred for 12 h. After consumption of the starting material (by TLC), the reaction mixture was poured into chilled water (200 mL) and extracted with diethylether (3×250 mL). The combined organic layers were washed with water (3×250 mL). The organic extracts were dried over anhydrous Na₂SO₄, filtered and concentrated under reduced pressure to afford Int B (60 g, 46%) as a brown syrup was used directly for next step without any purification.

$^1$H NMR (500 MHz, CDCl₃): δ 7.38-7.30 (m, 10H), 5.16 (s, 2H), 5.10 (s, 2H), 4.70 (d, J=4.0 Hz, 1H), 4.38 (d, J=4.6 Hz, 1H), 2.49-2.35 (m, 2H), 2.21 (dd, J=6.2, 12.9 Hz, 1H), 2.02-1.93 (m, 1H), 1.42 (s, 9H).

Synthesis of dibenzyl L-glutamate hydrochloride (Int-C)

To a stirring solution of Int B (60.0 g, 140 mmol) in ether.HCl (250 mL) was added at 0° C. and stirred at RT for 12 h. The obtained precipitate was filtered and triturated with diethyl ether (3×100 mL) and hexane (3×200 mL). The filtered compound was dried under vacuum to afford Int-C (30 g, 58.8%) as white solid.

$^1$H-NMR (400 MHz, DMSO-d₆): δ 8.66 (s, 2H), 7.41-7.30 (m, 10H), 5.26 (s, 2H), 5.15 (s, 2H), 4.16 (t, J=6.6 Hz, 1H), 2.64-2.48 (m, 2H), 2.26-2.16 (m, 2H).

Synthesis of methyl 4-methylcyclohexane-1-carboxylate (1)

To a stirring solution of 4-methylcyclohexane-1-carboxylic acid (50.0 g, 352 mmol) in MeOH (500 mL), thionyl chloride (50.6 mL, 704 mmol) was added and stirred at 60° C. for 16 h. After consumption of the starting material (by TLC), the reaction mixture was concentrated under reduced pressure to afford 1 (52 g, crude) as a thick oil.

$^1$H NMR (400 MHz, CDCl$_3$) δ 3.68 (s, 3H), 2.51 (t, J=4.8 Hz, 2H), 2.0-1.96 (m, 4H), 1.23-1.20 (m, 4H), 0.90 (d, J=6.4, Hz, 3H).

Synthesis of methyl 1-((benzyloxy)methyl)-4-methylcyclohexane-1-carboxylate (2)

To a stirred solution of 1 (5.0 g, 32.05 mmol) in dry THF (50 mL), LiHMDS (1M solution in THF, 70.5 mL, 70.5 mmol) was added at −45° C. and stirred at same temperature for 2 h. benzyloxymethyl chloride (7.5 g, 48.0 mmol) was added drop wise. The reaction mixture was stirred at RT for 2 h. After consumption of the starting material (by TLC), the reaction mixture was quenched with saturated NH$_4$Cl solution (300 mL) and extracted with EtOAc (3×300 mL). The combined organic layer was washed with brine (100 mL), dried over Na$_2$SO$_4$ and concentrated under reduced pressure. The residue was purified by flash column chromatography to afford 2 (7.0 g, 79%) as a thick oil.

LCMS (ESI): m/z 277.15 [M$^+$+1]

Synthesis of 1-((benzyloxy)methyl)-4-methylcyclohexane-1-carboxylic acid (3)

To a stirring solution of 2 (7.0 g, 25.3 mmol) in THF and MeOH (5:1, 30 mL), NaOH (3.1 g, 77.5) in water (5 mL) was added and heated at 80° C. for 16 h. After consumption of the starting material (by TLC), the reaction mixture was acidified with 1N HCl solution to pH—4-5, extracted with EtOAc (3×100 mL). The combined organic layer was washed with brine (100 mL), dried over Na$_2$SO$_4$ and concentrated under reduced pressure to afford 3 (5.25 g, crude) as a thick oil.

LCMS (ESI): m/z 261 [M−1]$^−$.

Synthesis of 4-(hydroxymethyl)tetrahydro-2H-pyran-4-carboxylic acid (4)

To a stirring solution of 3 (5.2 g, 19.8 mmol) in MeOH (60 mL), 10% Pd/C (50% wet, 1.0 g) was added at room temperature and stirred under H$_2$ atmosphere (balloon) for 12 h. After consumption of the starting material (by TLC), the reaction mixture was filtered through a pad of celite and washed with MeOH (50 mL). The filtrate was concentrated under reduced pressure. The residue was purified by trituration with n-pentane to afford 4 (3.2 g, crude) as a colorless solid.

$^1$H NMR (400 MHz, DMSO-d6) δ 12.2 (s, 1H), 4.70 (t, J=8 Hz, 1H), 3.32-3.31 (m, 1H), 1.96 (d, J=6 Hz, 2H), 1.54 (d, J=10.8 Hz, 1H), 1.36 (d, J=12 Hz, 2H), 1.12-1.06 (m, 1H), 1.02-0.98 (m, 2H), 0.96-0.81 (m, 5H).

Synthesis of dibenzyl (1-(hydroxymethyl)-4-methylcyclohexane-1-carbonyl)-L-glutamate (5)

To a stirred solution of 4 (1.5 g, 8.72 mmol) in DMF (25 mL), Int-C (3.3 g, 9.15 mmol), HATU (4.4 g, 13.0 mmol) and DIPEA (4.6 mL, 26.1 mmol) were added at 0° C. under nitrogen atmosphere and stirred at room temperature for 12 h. After consumption of the starting material (by TLC), the reaction mixture was quenched with water (100 mL) and extracted with EtOAc (2×75 mL). The combined organic layer was washed with brine (50 mL), dried over Na$_2$SO$_4$ and concentrated under reduced pressure. The residue was purified by column chromatography to afford 5 (2.3 g, 55%) as an off white solid.

LCMS (ESI): m/z 482 [M$^+$+1]

Synthesis of dibenzyl 2-(7-methyl-1-oxo-2-azaspiro[3.5]nonan-2-yl)pentanedioate (6-F1 and 6-F2)

To a stirred solution of triphenylphosphine (0.92 g, 3.51 mmol) in THF (15 mL), DIAD (0.7 mL, 3.51 mmol) was added drop wise at 0° C. under nitrogen atmosphere and stirred for 15 minutes. To a resulting reaction mixture a solution of 5 (1.3 g, 2.70 mmol) in THF (10 mL) was added drop wise and allowed to stir at RT for 4 h. After consumption of the starting material (by TLC), the reaction mixture was quenched with water (150 mL) and extracted with EtOAc (2×100 mL). The combined organic layer was washed with brine (50 mL), dried over Na$_2$SO$_4$ and concentrated under reduced pressure. The residue was purified by column chromatography to afford 6-F1 and 6-F2 (1.0 g, 84%) as thick oil.

LCMS (ESI): m/z 464 [M$^+$+1]

Synthesis of 2-(7-methyl-1-oxo-2-azaspiro[3.5]nonan-2-yl)pentanedioic acid (7-F1 and 7-F2)

To a stirring solution of 6-F1 and 6-F2 (0.9 g, 1.94 mmol) in EtOAc (30 mL), 10% Pd/C (50% wet, 0.4 g) was added at room temperature and stirred under H$_2$ atmosphere (balloon) for 12 h. After consumption of the starting material (by TLC), the reaction mixture was filtered through a pad of celite and washed with MeOH (10 mL). The filtrate was concentrated under reduced pressure. The residue was purified by trituration with n-pentane to afford 7-F1 and 7-F2 (0.63 g, crude solid).

LCMS (ESI): m/z 284 [M$^+$+1]

Synthesis of 2-(7-methyl-1-oxo-2-azaspiro[3.5]nonan-2-yl)pentanediamide (BE and BF)

To a stirred solution of 7-F1 and 7-F2 (0.62 g, 2.18 mmol) in DCM (6 mL), HOBt (0.89 g, 6.56 mmol), EDC.HCl (1.2 g, 6.56 mmol), NH$_4$Cl (0.7 g, 13.1 mmol) and DIPEA (2.2 mL, 13.1 mmol) were added at 0° C. under nitrogen atmosphere and stirred at RT for 12 h. After consumption of the starting material (by TLC), the reaction mixture was quenched with water (100 mL) and extracted with EtOAc (2×75 mL). The combined organic layer was washed with brine (50 mL), dried over Na$_2$SO$_4$ and concentrated under reduced pressure. The residue was purified by column chromatography to afford mixture of compounds (BE and BF) (0.4 g) as a colorless solid. The mixture was purified by preparative HPLC followed by chiral HPLC to afford BE (82 mg) and BF (190 mg) as off-white solids.

BE: $^1$H NMR (400 MHz, DMSO-d$_6$) δ 7.45 (s, 1H), 7.32 (s, 1H), 7.07 (s, 1H), 6.77 (s, 1H), 4.05 (dd, J=9.6, 5.4 Hz, 1H), 3.09 (d, J=5.3 Hz, 1H), 2.99 (d, J=5.3 Hz, 1H), 2.11-1.97 (m, 2H), 1.93-1.70 (m, 4H), 1.54 (t, J=9.8 Hz, 4H), 1.37 (s, 3H), 0.88 (d, J=4.7 Hz, 3H).

LCMS (ESI): m/z 282 [M$^+$+1]

HPLC: 99.7%

BF: ¹H NMR (400 MHz, DMSO-d₆) δ 7.45 (s, 1H), 7.32 (s, 1H), 7.07 (s, 1H), 6.77 (s, 1H), 4.05 (dd, J=9.6, 5.4 Hz, 1H), 3.09 (d, J=5.3 Hz, 1H), 2.99 (d, J=5.3 Hz, 1H), 2.11-1.97 (m, 2H), 1.94-1.70 (m, 4H), 1.54 (t, J=9.8 Hz, 4H), 1.37 (s, 3H), 0.88 (d, J=4.7 Hz, 3H).

LCMS (ESI): m/z 282 [M⁺+1]

HPLC: 99.9%

Example 14—Synthesis of Compounds EM and EN

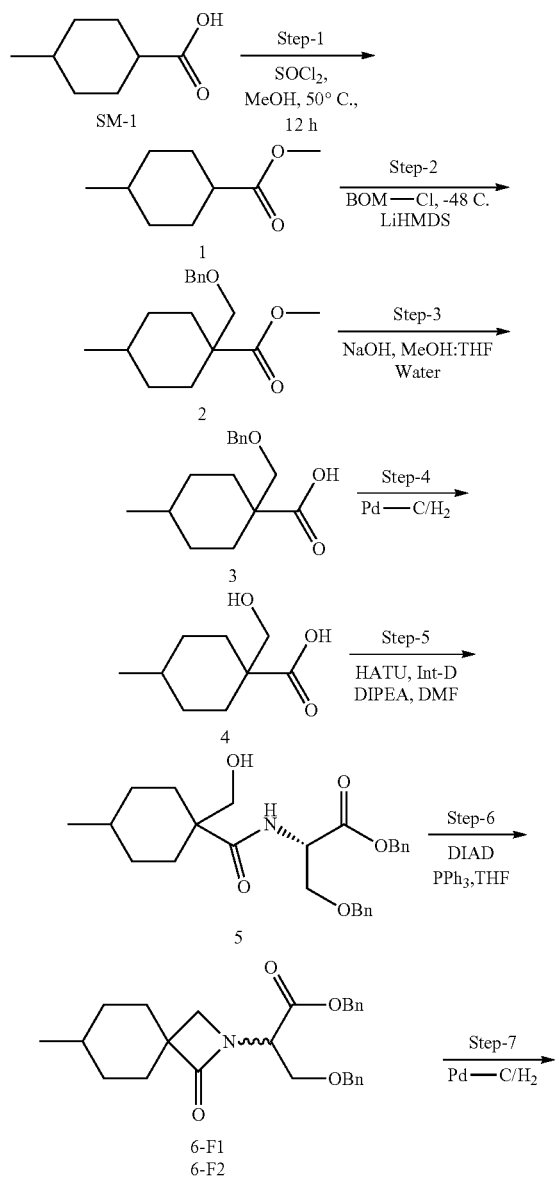

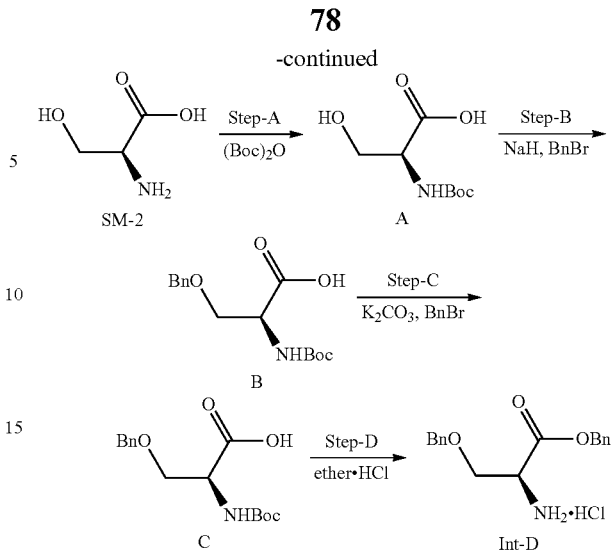

Synthesis of (S)-2-((tert-butoxycarbonyl) amino)-3-hydroxypropanoic acid (A)

To a stirring solution of SM-2 (76 g, 723 mmol) in 1, 4 dioxane/H₂O (350 mL/300 mL) were added NaOH (61 g, 1.51 mmol), Boc₂O (190 mL, 868 mmol) at 0° C. The reaction mixture was stirred at RT for 16 h. After consumption of the starting material (by TLC), the reaction mixture was acidified with 2N HCl (pH-4) and extracted with EtOAc (5×500 mL). The combined organic layer was dried over anhydrous Na₂SO₄ and concentrated under reduced pressure to afford Int A (100 g, 67.5%) as a yellow syrup.

¹H NMR: (400 MHz, CDCl₃): δ 6.54 (br s, 1H), 5.77 (br s, 1H), 4.35-4.04 (m, 1H), 3.87-3.84 (m, 2H), 1.45 (s, 9H).

Synthesis of (S)-3-(benzyloxy)-2-((tert-butoxycarbonyl) amino) propanoic acid (B)

To a stirring solution of Int A (50 g, 245 mmol) in DMF (650 mL) was added NaH (60%) (23 g, 563 mmol) at −15° C. and stirred for 2 h. After adding benzyl bromide (32.8 mL, 269 mmol) slowly, the reaction mixture was warmed to RT and stirred for 12 h. After consumption of the starting material (by TLC), the reaction mixture was poured into chilled water (200 mL) and extracted with diethylether (2×250 mL). The aqueous layer was acidified with citric acid (pH~4) and extracted with EtOAc (2×500 mL). The combined organic layers were washed with water (3×250 mL). The organic extracts were dried over anhydrous Na₂SO₄, filtered and concentrated under reduced pressure to afford Int B (54 g, 75%) as a brown syrup.

¹H NMR: (400 MHz, CDCl₃): δ 7.32-7.26 (m, 5H), 5.43 (d, J=7.6 Hz, 1H), 4.70-4.46 (m, 1H), 4.45 (s, 2H), 4.13-3.91 (m, 1H), 3.73-3.70 (m, 1H), 1.44 (s, 9H)

Synthesis of (S)-benzyl 3-(benzyloxy)-2-((tert-butoxycarbonyl) amino) propanoate (C)

To a stirring solution of Int B (36 g, 122 mmol) in DMF (250 mL) was added Na₂CO₃ (20 g, 183 mmol) at 0° C. and added benzyl bromide (18 mL, 146 mmol) slowly. The reaction mixture temperature was warmed to RT and stirred for 12 h. After consumption of the starting material (by TLC), the reaction mixture was poured into chilled water (200 mL) and extracted with diethylether (2×250 mL). The combined organic layers were washed with water (3×250 mL), dried over anhydrous Na$_2$SO$_4$, filtered and concentrated under reduced pressure to afford Int C (42 g, 91%) as a brown syrup was used directly for next step without any purification.

Synthesis of (S)-benzyl 2-amino-3-(benzyloxy) propanoate hydrochloride (D)

To a stirring solution of Int C (10 g, 25.9 mmol) in ether.HCl (50 mL) was added at 0° C. and stirred at RT for 12 h. The obtained precipitate was filtered and triturated with diethylether (2×100 mL). The filtered compound was dried under vacuum to afford Int D (5 g, 60%) as a white solid.

$^1$H NMR: (400 MHz, DMSO-d$_6$): δ 8.66 (s, 2H), 7.38-7.27 (m, 10H), 5.29-5.22 (m, 2H), 4.57-4.44 (m, 3H), 3.91-3.81 (m, 2H).

Synthesis of methyl 4-methylcyclohexane-1-carboxylate (1)

To a stirring solution of 4-methylcyclohexane-1-carboxylic acid (50.0 g, 352 mmol) in MeOH (500 mL), thionyl chloride (50.6 mL, 704 mmol) was added and stirred at 60° C. for 16 h. After consumption of the starting material (by TLC), the reaction mixture was concentrated under reduced pressure to afford 1 (52 g, crude) as a thick oil.

$^1$H NMR (400 MHz, CDCl$_3$) δ 3.68 (s, 3H), 2.51 (t, J=4.8 Hz, 2H), 2.0-1.96 (m, 4H), 1.23-1.20 (m, 4H), 0.90 (d, J=6.4, Hz, 3H).

Synthesis of methyl 1-((benzyloxy)methyl)-4-methylcyclohexane-1-carboxylate (2)

To a stirred solution of 1 (5.0 g, 32.05 mmol) in dry THF (50 mL), LiHMDS (1M solution in THF, 70.5 mL, 70.5 mmol) was added at −45° C. and stirred at same temperature for 2 h. benzyloxymethyl chloride (7.5 g, 48.0 mmol) was added drop wise. The reaction mixture was stirred at room temperature for 2 h. After consumption of the starting material (by TLC), the reaction mixture was quenched with saturated NH$_4$Cl solution (300 mL) and extracted with EtOAc (3×300 mL). The combined organic layer was washed with brine (100 mL), dried over Na$_2$SO$_4$ and concentrated under reduced pressure. The residue was purified by flash column chromatography to afford 2 (7.0 g, 79%) as a thick oil.

LCMS (ESI): m/z 277.15 [M$^+$+1]

Synthesis of 1-((benzyloxy)methyl)-4-methylcyclohexane-1-carboxylic acid (3)

To a stirring solution of 2 (7.0 g, 25.3 mmol) in THF and MeOH (5:1, 30 mL), NaOH (3.1 g, 77.5) in water (5 mL) was added and heated at 80° C. for 16 h. After consumption of the starting material (by TLC), the reaction mixture was acidified with 1N HCl solution to pH—4-5, extracted with EtOAc (3×100 mL). The combined organic layer was washed with brine (100 mL), dried over Na$_2$SO$_4$ and concentrated under reduced pressure to afford 3 (5.25 g, crude) as a thick oil.

LCMS (ESI): m/z 261 [M$^+$−1]

Synthesis of 4-(hydroxymethyl)tetrahydro-2H-pyran-4-carboxylic acid (4)

To a stirring solution of 3 (5.2 g, 19.8 mmol) in MeOH (60 mL), 10% Pd/C (50% wet, 1.0 g) was added at room temperature and stirred under H$_2$ atmosphere (balloon) for 12 h. After consumption of the starting material (by TLC), the reaction mixture was filtered through a pad of celite and washed with MeOH (50 mL). The filtrate was concentrated under reduced pressure. The residue was purified by trituration with n-pentane to afford 4 (3.2 g, crude) as a colorless solid.

$^1$H NMR (400 MHz, DMSO-d6) δ 12.2 (s, 1H), 4.70 (t, J=8 Hz, 1H), 3.32-3.31 (m, 1H), 1.96 (d, J=6 Hz, 2H), 1.54 (d, J=10.8 Hz, 1H), 1.36 (d, J=12 Hz, 2H), 1.12-1.06 (m, 1H), 1.02-0.98 (m, 2H), 0.96-0.81 (m, 5H).

Synthesis of benzyl O-benzyl-N-(1-(hydroxymethyl)-4-methylcyclohexane-1-carbonyl)-L-serinate (5)

To a stirred solution of 4 (1.6 g, 9.3 mmol) in DMF (25 mL), Int D (3.3 g, 10.2 mmol), HATU (4.6 g, 12.0 mmol) and DIPEA (4.8 mL, 27.9 mmol) were added at 0° C. under nitrogen atmosphere and stirred at RT for 12 h. After consumption of the starting material (by TLC), the reaction mixture was quenched with water (100 mL) and extracted with EtOAc (2×75 mL).

The combined organic layer was washed with brine (50 mL), dried over Na$_2$SO$_4$ and concentrated under reduced pressure. The residue was purified by column chromatography to afford 5 (3.0 g, 75%) as off white solid.

LCMS (ESI): m/z 440 [M$^+$+1]

Synthesis of benzyl (S)-3-(benzyloxy)-2-(7-methyl-1-oxo-2-azaspiro[3.5]nonan-2-yl)propanoate (6-F1 and 6-F2)

To a stirred solution of triphenylphosphine (2.12 g, 8.09 mmol) in THF (35 mL), DIAD (1.6 mL, 8.09 mmol) was added drop wise at room temperature under nitrogen atmosphere and stirred for 15 minutes. A solution of 5 (3.0 g, 6.23 mmol) in THF (10 mL) was added drop wise and allowed to stir at RT for 4 h. After consumption of the starting material (by TLC), the reaction mixture was quenched with water (150 mL) and extracted with EtOAc (2×100 mL). The combined organic layer was washed with brine (50 mL), dried over Na$_2$SO$_4$ and concentrated under reduced pressure. The residue was purified by column chromatography to afford 6-F1 and 6-F2 mixture (2.63 g, 91%) as thick oil.

LCMS (ESI): m/z 422[M$^+$+1]

Synthesis of 3-hydroxy-2-(7-methyl-1-oxo-2-azaspiro[3.5]nonan-2-yl)propanoic acid (EM and EN)

To a stirring solution of 6-F1 and 6-F2 (2.6 g, 6.16 mmol) in EtOAc (50 mL), 10% Pd/C (50% wet, 520 mg) was added at room temperature and stirred under H$_2$ atmosphere (balloon) for 12 h. After consumption of the starting material (by TLC), the reaction mixture was filtered through a pad of celite and washed with MeOH (50 mL). The filtrate was concentrated under reduced pressure. The residue was purified by column chromatography to afford mixture of compounds EM and EN (1.43 g) as a colorless solid. The mixture was purified by preparative HPLC followed by chiral HPLC to afford EM (307 mg) and EN (200 mg) as an off-white solid.

EM: $^1$H NMR (400 MHz, DMSO-d$_6$) δ 12.88 (s, 1H), 4.20 (t, J=5.3 Hz, 1H), 3.72 (dd, J=5.4, 2.3 Hz, 2H), 3.15-3.02 (m, 2H), 1.90 (d, J=12.1 Hz, 2H), 1.56-1.55 (m, 4H), 1.46-1.31 (m, 3H), 0.88 (d, J=4.4 Hz, 3H).

LCMS (ESI): m/z 242 [M++1]

HPLC: 97.1%

EN: ¹H NMR (400 MHz, DMSO-d6) δ 12.91 (s, 1H), 4.20 (t, J=5.2 Hz, 1H), 3.72 (dd, J=5.4, 2.3 Hz, 2H), 3.15-3.02 (m, 2H), 1.90 (d, J=12.2 Hz, 2H), 1.56-1.55 (m, 4H), 1.46-1.31 (m, 3H), 0.88 (d, J=4.4 Hz, 3H).

LCMS (ESI): m/z 242 [M++1]

HPLC: 93.7%

Example 15—Synthesis of Compound EO

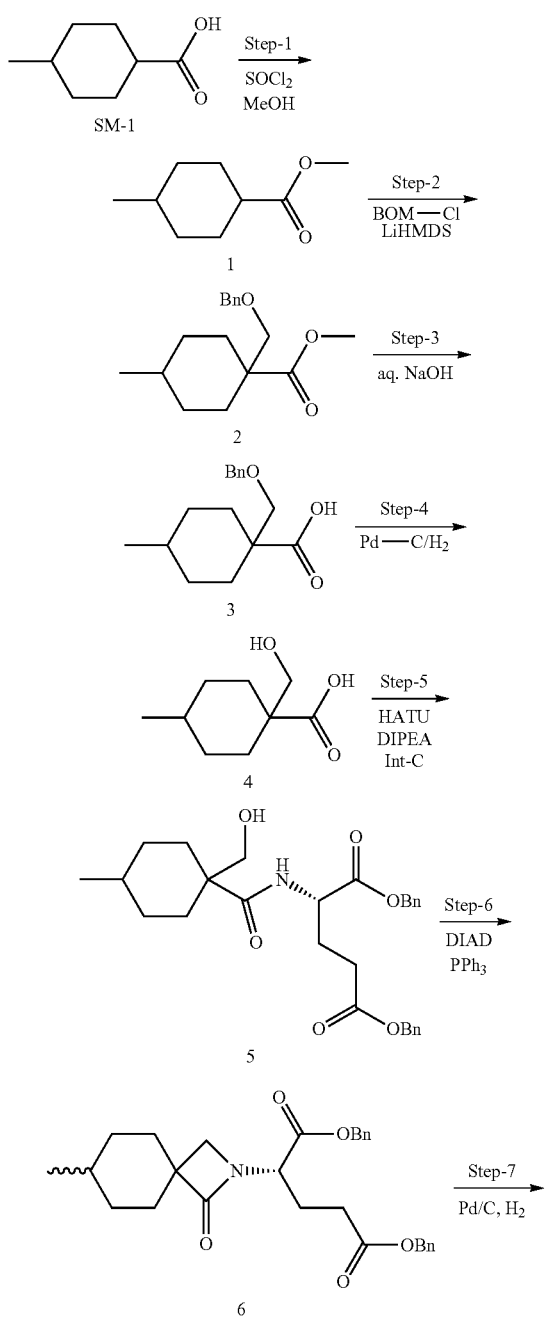

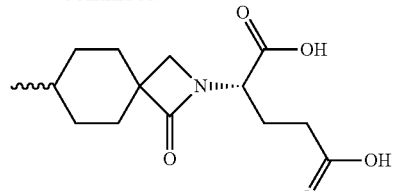

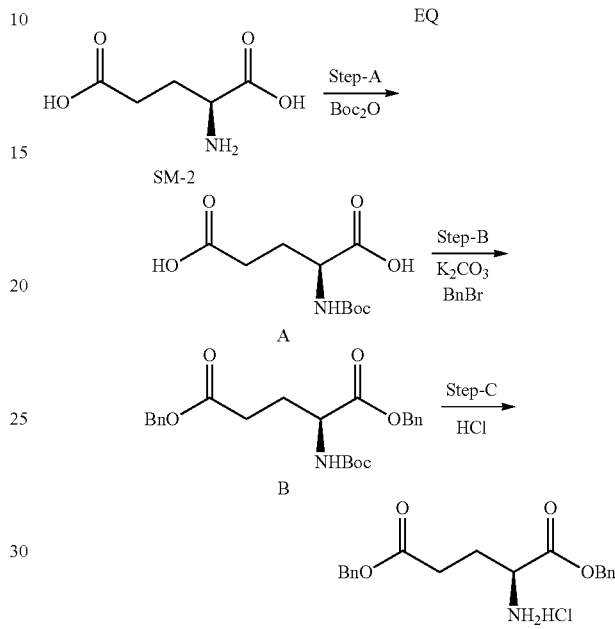

Synthesis of (tert-butoxycarbonyl)-L-glutamic acid (A)

To a solution of SM-2 (100 g, 680 mmol) in 1,4-dioxane (400 mL) and H₂O (300 mL) were added NaOH (81.6 g, 2.04 mol), Boc₂O (178 g, 816 mmol) at 0° C. The reaction mixture was stirred at room temperature for 16 h. After consumption of the starting material (by TLC), the reaction mixture was acidified with aqueous 2N HCl (pH~4) and extracted with EtOAc (5×500 mL). The combined organic layers were dried over anhydrous Na₂SO₄ and concentrated under reduced pressure to afford Int A (75 g, 44.6%) as a yellow syrup.

¹H NMR (400 MHz, CDCl₃) δ 5.34-5.29 (m, 1H), 4.43-4.17 (m, 1H), 2.51 (td, J=2.4, 7.1 Hz, 2H), 2.28-2.18 (m, 1H), 2.07-2.01 (m, 1H), 1.45 (s, 9H).

LCMS (ESI): (m/z) 246.0 [M+−1]⁻

Synthesis of dibenzyl (tert-butoxycarbonyl)-L-glutamate (B)

To a solution of Int A (75.0 g, 303 mmol) in DMF (500 mL) was added K₂CO₃ (125 g, 910 mmol) at 0° C. and added benzyl bromide (114 g, 668 mmol) drop wise and the reaction mixture temperature was stirred at room temperature for 12 h. After consumption of the starting material (by TLC), the reaction mixture was poured into chilled water (200 mL) and extracted with diethylether (3×250 mL). The combined organic layers were washed with water (3×250 mL). The organic layers were dried over anhydrous Na₂SO₄, filtered and concentrated under reduced pressure to afford Int B (60 g, 46%) as a brown syrup. The crude was forwarded to next step without any purification.

$^1$H NMR (500 MHz, CDCl$_3$) δ 7.38-7.30 (m, 10H), 5.16 (s, 2H), 5.10 (s, 2H), 4.70 (d, J=4.0 Hz, 1H), 4.38 (d, J=4.6 Hz, 1H), 2.49-2.35 (m, 2H), 2.21 (dd, J=6.2, 12.9 Hz, 1H), 2.02-1.93 (m, 1H), 1.42 (s, 9H).

Synthesis of dibenzyl L-glutamate hydrochloride (C)

To a solution of Int B (60.0 g, 140 mmol) in HCl in ether (250 mL) was added at 0° C. and stirred at room temperature for 12 h. The obtained precipitate was filtered and triturated with diethyl ether (3×100 mL) and hexane (3×200 mL). The residue was dried under reduced pressure to afford C (30 g, 58.8%) as a white solid.

$^1$H NMR (400 MHz, DMSO-d$_6$) δ 8.66 (s, 2H), 7.41-7.30 (m, 10H), 5.26 (s, 2H), 5.15 (s, 2H), 4.16 (t, J=6.6 Hz, 1H), 2.64-2.48 (m, 2H), 2.26-2.16 (m, 2H).

Synthesis of methyl 4-methylcyclohexane-1-carboxylate (1)

To a solution of 4-methylcyclohexane-1-carboxylic acid (50.0 g, 352 mmol) in MeOH (500 mL), thionyl chloride (50.6 mL, 704 mmol) was added and stirred at 60° C. for 16 h. After consumption of the starting material (by TLC), the reaction mixture was concentrated under reduced pressure to afford 1 (52 g, crude) as a thick oil.

$^1$H NMR (400 MHz, CDCl$_3$) δ 3.68 (s, 3H), 2.51 (t, J=4.8 Hz, 2H), 2.0-1.96 (m, 4H), 1.23-1.20 (m, 4H), 0.90 (d, J=6.4, Hz, 3H).

Synthesis of methyl 1-((benzyloxy)methyl)-4-methylcyclohexane-1-carboxylate (2)

To a solution of 1 (5.0 g, 32.05 mmol) in dry THF (50 mL), LiHMDS (1M solution in THF, 70.5 mL, 70.5 mmol) was added at −45° C. and stirred at same temperature for 2 h. benzyloxymethyl chloride (7.5 g, 48.0 mmol) was added drop wise and the reaction mixture was stirred at room temperature for 2 h. After consumption of the starting material (by TLC), the reaction mixture was quenched with saturated aqueous NH$_4$Cl (300 mL) and extracted with EtOAc (3×300 mL). The combined organic layer was washed with brine (100 mL), dried over Na$_2$SO$_4$ and concentrated under reduced pressure. The residue was purified by flash column chromatography to afford 2 (7.0 g, 79%) as a thick oil.

LCMS (ESI): m/z 277.15 [M$^+$+1]

Synthesis of 1-((benzyloxy)methyl)-4-methylcyclohexane-1-carboxylic acid (3)

To a solution of 2 (7.0 g, 25.3 mmol) in THF and MeOH (5:1, 30 mL), NaOH (3.1 g, 77.5) in water (5 mL) was added and heated at 80° C. for 16 h. After consumption of the starting material (by TLC), the reaction mixture was acidified with 1N HCl solution to pH—4-5, extracted with EtOAc (3×100 mL). The combined organic layer was washed with brine (100 mL), dried over Na$_2$SO$_4$ and concentrated under reduced pressure to afford 3 (5.25 g, crude) as a thick oil.

LCMS (ESI): m/z 261 [M−1]$^-$.

Synthesis of 4-(hydroxymethyl)tetrahydro-2H-pyran-4-carboxylic acid (4)

To a solution of 3 (5.2 g, 19.8 mmol) in MeOH (60 mL), 10% Pd/C (50% wet, 1.0 g) was added at room temperature and stirred under H$_2$ atmosphere (balloon) for 12 h. After consumption of the starting material (by TLC), the reaction mixture was filtered through a pad of celite and washed with MeOH (50 mL). The filtrate was concentrated under reduced pressure. The residue was purified by trituration with n-pentane to afford 4 (3.2 g, crude) as a colorless solid.

$^1$H NMR (400 MHz, DMSO-d$_6$) δ 12.2 (s, 1H), 4.70 (t, J=8 Hz, 1H), 3.32-3.31 (m, 1H), 1.96 (d, J=6 Hz, 2H), 1.54 (d, J=10.8 Hz, 1H), 1.36 (d, J=12 Hz, 2H), 1.12-1.06 (m, 1H), 1.02-0.98 (m, 2H), 0.96-0.81 (m, 5H).

Synthesis of dibenzyl (1-(hydroxymethyl)-4-methylcyclohexane-1-carbonyl)-L-glutamate (5)

To a solution of 4 (1.5 g, 8.72 mmol) in DMF (25 mL), Int-C (3.3 g, 9.15 mmol), HATU (4.4 g, 13.0 mmol) and DIPEA (4.6 mL, 26.1 mmol) were added at 0° C. under nitrogen atmosphere and stirred at room temperature for 12 h. After consumption of the starting material (by TLC), the reaction mixture was quenched with water (100 mL) and extracted with EtOAc (2×75 mL). The combined organic layer was washed with brine (50 mL), dried over Na$_2$SO$_4$ and concentrated under reduced pressure. The residue was purified by column chromatography to afford 5 (2.3 g, 55%) as an off-white solid.

LCMS (ESI): m/z 482 [M$^+$+1]

Synthesis of dibenzyl (S)-2-(7-methyl-1-oxo-2-azaspiro[3.5]nonan-2-yl)pentanedioate (6)

To a solution of triphenylphosphine (0.92 g, 3.51 mmol) in THF (15 mL), DIAD (0.7 mL, 3.51 mmol) was added drop wise at 0° C. under nitrogen atmosphere and stirred for 15 minutes. A solution of 5 (1.3 g, 2.70 mmol) in THF (10 mL) was added drop wise to the reaction mixture and stirred at room temperature for 4 h. After consumption of the starting material (by TLC), the reaction mixture was quenched with water (150 mL) and extracted with EtOAc (2×100 mL). The combined organic layer was washed with brine (50 mL), dried over Na$_2$SO$_4$ and concentrated under reduced pressure. The residue was purified by column chromatography to afford 6 (1.0 g, 84%) as a thick oil.

LCMS (ESI): m/z 464 [M$^+$+1]

Synthesis of (S)-2-(7-methyl-1-oxo-2-azaspiro[3.5]nonan-2-yl)pentanedioic acid (EQ)

To a solution of 6 (0.8 g, 1.72 mmol) in EtOAc (20 mL), 10% Pd/C (50% wet, 0.1 g) was added at room temperature and stirred under H$_2$ atmosphere (balloon) for 12 h. After consumption of the starting material (by TLC), the reaction mixture was filtered through a pad of celite and washed with MeOH (10 mL). The filtrate was concentrated under reduced pressure. The residue was purified by trituration with diethyl ether and n-pentane to afford EQ (0.46 g, 94.2%).

$^1$H NMR (400 MHz, DMSO-d$_6$) δ 12.60-12.40 (m, 2H), 4.17-4.13 (m, 1H), 3.00-2.96 (m, 2H), 2.25 (t, J=7.2 Hz, 2H), 2.02-1.99 (m, 1H), 1.88-1.71 (m, 3H), 1.53-1.51 (m, 4H), 1.31-1.29 (m, 3H), 1.15-1.01 (m, 2H).

LCMS (ESI): m/z 283.95 [M$^+$+1]
HPLC: 97.01%

Example 16

Following the above procedures, the following compounds were or are prepared. It should be appreciated that the compound in the first column is a different stereoisomer, for example, a different enantiomer and/or different diastereomer, from the compound in the second column.

TABLE 1

| Structure and Compound |
|---|
| AA |
| AB |
| AC |
| AD |
| AE |
| AF |
| AG |

TABLE 1-continued

| Structure and Compound |
|---|
| AH |
| AI |
| AJ |
| AK |
| AL |
| AM |
| AN |

TABLE 1-continued

Structure and Compound

AO

AP

AQ

AS

AT

AU

AV

AW

AY

AZ

BA

BB

BC

TABLE 1-continued

Structure and Compound

BD

BE

BF

BG

BH

BI

BJ

BK

BL

BM

BN

BO

TABLE 1-continued

Structure and Compound

BP, BQ, BR, BS, BT, BU, BV, BW, BX, BY, BZ, CA, CB, CC

TABLE 1-continued
Structure and Compound
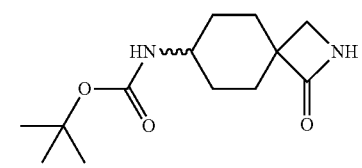 [SMILES: CC(C)(C)OC(=O)NC1CCC2(CC1)CNC2=O]
CD
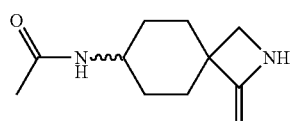
CE
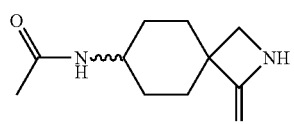
CF
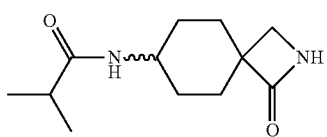 [SMILES: CC(C)C(=O)NC1CCC2(CC1)CNC2=O]
CG
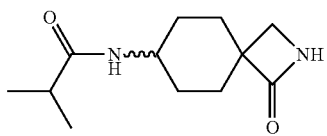
CH
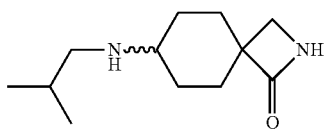
CI
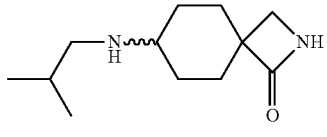
CJ
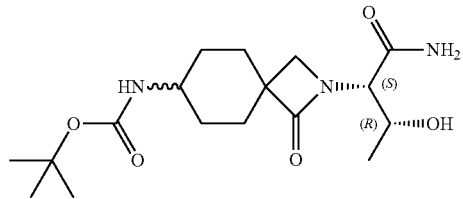
CK
TABLE 1-continued
Structure and Compound
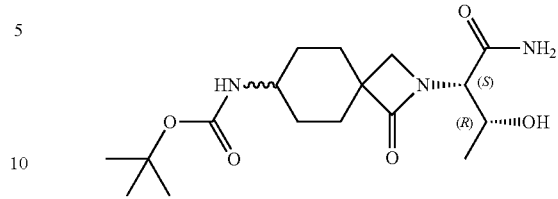
CL
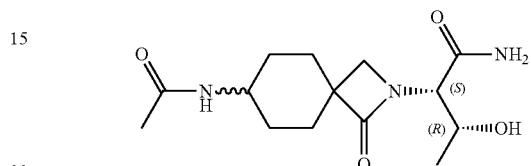
CM
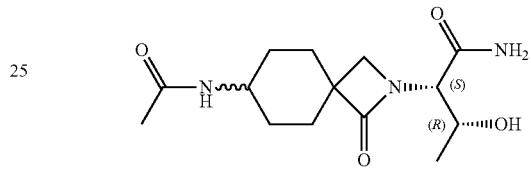
CN
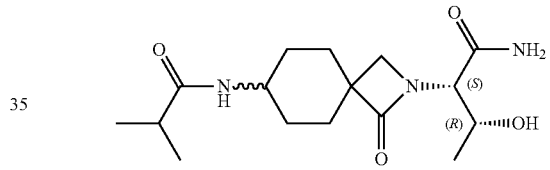
CO
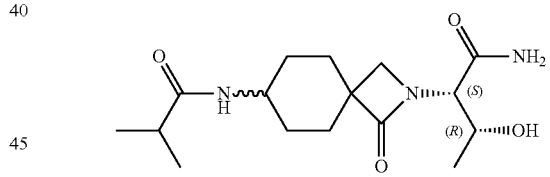
CP
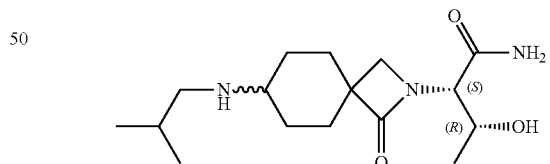
CQ
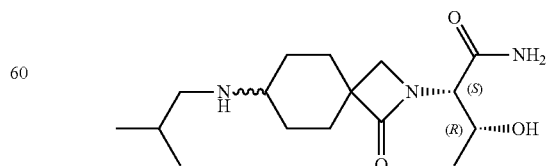
CR TABLE 1-continued Structure and Compound

CS

CT

CU

CV

CW

CX

CY

CZ

DA

DB

DC

DD

DE

DF

TABLE 1-continued
Structure and Compound
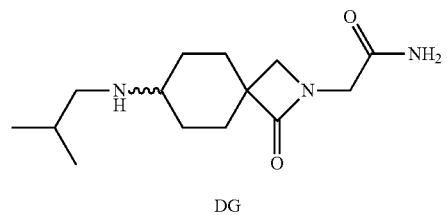
DG
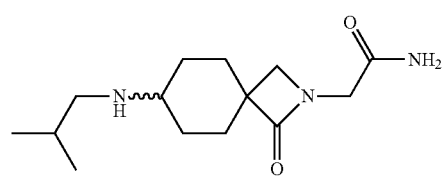 [SMILES: CC(C)CNC1CCC2(CC1)CN(CC(N)=O)C2=O]
DH
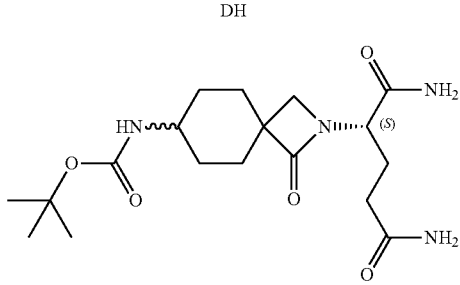
DI
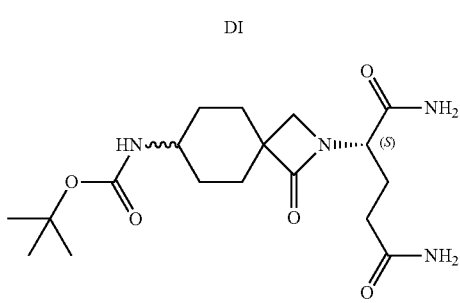
DJ
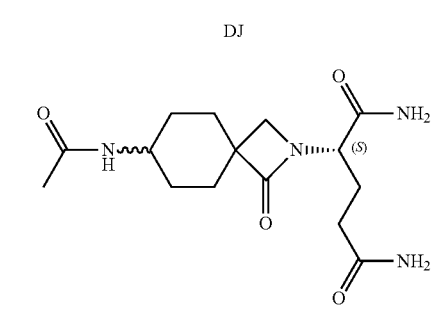
DK
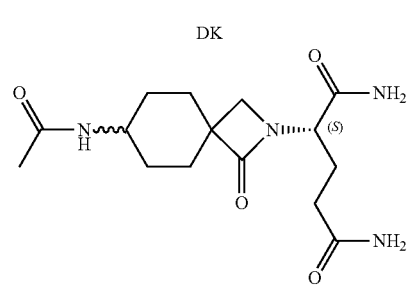
DL
TABLE 1-continued
Structure and Compound
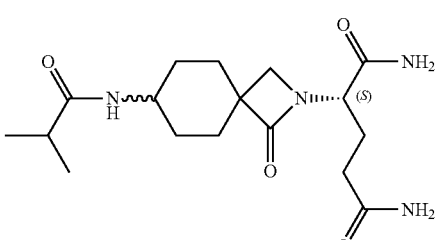
DM
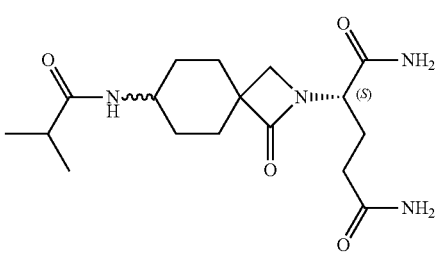
DN
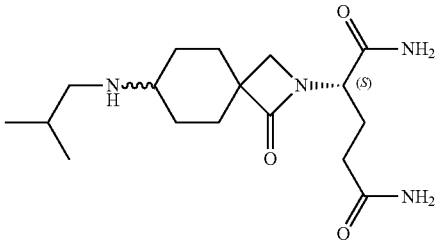
DO
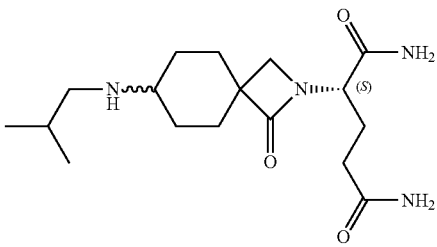
DP
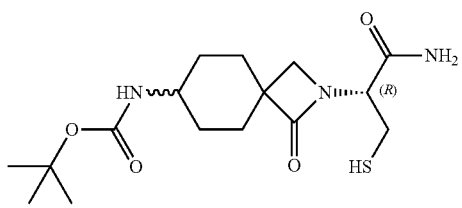
DQ TABLE 1-continued Structure and Compound

DR

DS

DT

DU

DV

DW

DX

DY

DZ

EA

EB

EC

ED

EE

EF

TABLE 1-continued
Structure and Compound
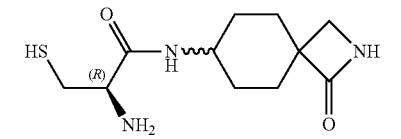
EG
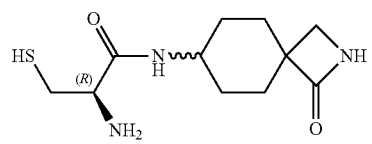
EH
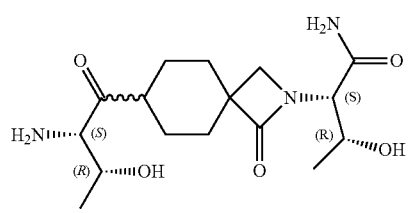
EI
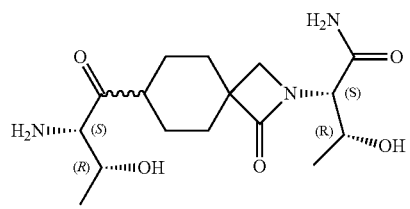
EJ
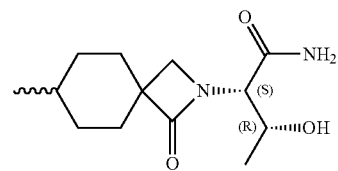
EK
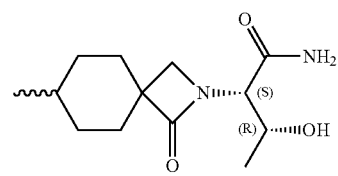
EL
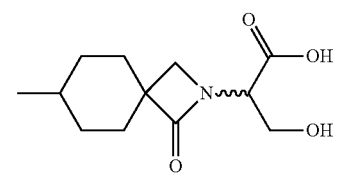 [SMILES: CC1CCC2(CC1)CN(C(CO)C(=O)O)C2=O]
EM
TABLE 1-continued
Structure and Compound
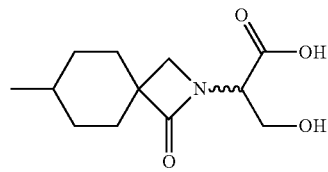 [SMILES: CC1CCC2(CC1)CN(C(CO)C(=O)O)C2=O]
EN
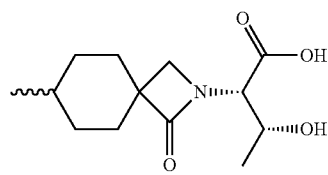 [SMILES: CC1CCC2(CC1)CN([C@H](C(=O)O)[C@@H](C)O)C2=O]
EO
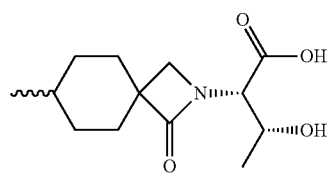 [SMILES: CC1CCC2(CC1)CN([C@H](C(=O)O)[C@@H](C)O)C2=O]
EP
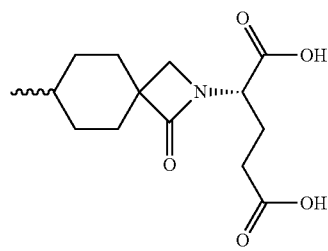 [SMILES: CC1CCC2(CC1)CN([C@@H](CCC(=O)O)C(=O)O)C2=O]
EQ
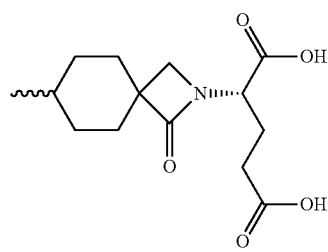 [SMILES: CC1CCC2(CC1)CN([C@@H](CCC(=O)O)C(=O)O)C2=O]
ER
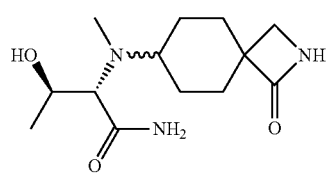 [SMILES: C[C@@H](O)[C@@H](C(N)=O)N(C)C1CCC2(CC1)CNC2=O]
ES TABLE 1-continued Structure and Compound

ET, EU, EV, EW, EX, EY, EZ, FA, FB, FC, FD, FE, FF

Example 17

This example demonstrates the positive emotional learning (PEL) test. Experiments were conducted as described in Burgdorf et al., "The effect of selective breeding for differential rates of 50-kHz ultrasonic vocalizations on emotional behavior in rats," Devel. Psychobiol., 51:34-46 (2009). Rat 50-kHz ultrasonic vocalization (hedonic USVs) is a validated model for the study of positive affective state and is best elicited by rough-and-tumble play. 50-kHz ultrasonic vocalizations have previously been shown to be positively correlated with reward and appetitive social behavior in rats, and to reflect a positive affective state.

The PEL assay measures the acquisition of positive (hedonic) 50-kHz ultrasonic vocalizations (USVs) to a social stimulus, heterospecific rough and tumble play stimulation. Heterospecific rough-and-tumble play stimulation was administered by the experimenter's right hand. One hour after administration of test compound or vehicle negative control (0.5% sodium carboxymethyl cellulose in 0.95 sterile saline), animals received 3 min of heterospecific rough-and-tumble play that consisted of alternating 15 sec blocks of heterospecific play and 15 sec of no-stimulation. High frequency ultrasonic vocalizations (USVs) were recorded and analyzed by sonogram with Avasoft SASlab Pro (Germany) as previously described by Burgdorf et al., "Positive emotional learning is regulated in the medial prefrontal cortex by GluN2B-containing NMDA receptors," Neuroscience, 192:515-523 (2011). Frequency modulated 50-kHz USVs that occurred during each of the no-stimulation periods were quantified to measure PEL. Animals were not habituated to play stimulation before testing. Positive emotional learning was measured during the conditioned stimulus (CS) trials preceding the tickle unconditioned stimulus (UCS) trials. Animals received 15 second trials consisting of 6 CS and 6 UCS trials each (3 min total).

The table below summarizes the findings. As each experiment includes its own vehicle group, an example (typical) vehicle score is shown. Max effect (mean number of 50 kHz USVs per 15 seconds) is reported as ^: <6.0; *: 6-10.9; : 11-16.9; *: 17-22.

| Compound | Route | Dose (mg/kg) | Max Effect |
|---|---|---|---|
| Vehicle | PO | N/A | ^ |
| AL | PO | .001-1 | ** |
| AG | PO | .001-1 | ** |
| AI | PO | .001-1 | ** |
| AD | PO | .001-1 | *** |
| AO | PO | .1 | * |
| AP | PO | .1 | ** |
| AQ | PO | .1 | ** |

Example 18

Assays were conducted as described by Moskal et al., "GLYX-13: a monoclonal antibody-derived peptide that acts as an N-methyl-D-aspartate receptor modulator," Neuropharmacology, 49, 1077-87, 2005. These studies were designed to determine if the test compounds act to facilitate NMDAR activation in NMDAR2A, NMDAR2B, NMDAR2C or NMDAR2D expressing HEK cell membranes as measured by increases in [$^3$H]MK-801 binding.

In the assay, 300 μg of NMDAR expressing HEK cell membrane extract protein was preincubated for 15 minutes at 25° C. in the presence of saturating concentrations of glutamate (50 μM) and varying concentrations of test compound ($1\times10^{15}$M–$1\times10^{-7}$M), or 1 mM glycine. Following the addition of 0.3 μCi of [$^3$H]MK-801 (22.5 Ci/mmol), reactions were again incubated for 15 minutes at 25° C. (nonequilibrium conditions). Bound and free [$^3$H]MK-801 were separated via rapid filtration using a Brandel apparatus.

In analyzing the data, the DPM (disintegrations per minute) of [$^3$H]MK-801 remaining on the filter were measured for each concentration of test compound or for 1 mM glycine. The DPM values for each concentration of a ligand (N=2) were averaged. The baseline value was determined from the best fit curve of the DPM values modeled using the GraphPad program and the log(agonist) vs. response (three parameters) algorithm was then subtracted from all points in the dataset. The % maximal [$^3$H]MK-801 binding was then calculated relative to that of 1 mM glycine: all baseline subtracted DPM values were divided by the average value for 1 mM glycine. The $EC_{50}$ and % maximal activity were then obtained from the best fit curve of the % maximal [$^3$H]MK-801 binding data modelled using the GraphPad program and the log(agonist) vs. response (three parameters) algorithm.

The tables below summarize the results for the wild type NMDAR agonists NMDAR2A, NMDAR2B, NMDAR2C, and NMDAR2D, and whether the compound is not an agonist (−), is an agonist (+), or is a strong agonist (++), where column A is based on the % maximal [$^3$H]MK-801 binding relative to 1 mM glycine (−=0; <100%=+; and >100%=++); and column B is based on log $EC_{50}$ values (0=−; ≥$1\times10^{-9}$ M (e.g., −8)=+; and <$1\times10^{-9}$ M (e.g., −10)=++).

| | NMDAR2A | | NMDAR2B | |
|---|---|---|---|---|
| Compound | A | B | A | B |
| AA | − | − | + | ++ |
| AK | − | − | − | − |
| AL | − | − | + | ++ |
| AG | + | + | + | ++ |
| AI | + | ++ | + | ++ |
| AJ | − | − | − | − |
| AE | + | ++ | − | − |
| AF | − | − | + | ++ |
| AD | − | − | + | + |
| AC | − | − | − | − |
| AM | − | − | − | − |
| AO | − | − | + | ++ |
| AN | + | ++ | − | − |
| AP | + | ++ | + | ++ |
| AQ | + | + | + | ++ |
| AB | + | + | + | ++ |
| BC | + | ++ | − | − |
| AS | + | ++ | + | ++ |
| AT | + | ++ | + | ++ |
| BE | − | − | + | ++ |
| BF | + | ++ | + | ++ |
| EM | + | ++ | − | − |
| EN | + | ++ | + | ++ |
| EQ | + | ++ | − | − |
| FC | + | ++ | ++ | ++ |
| FE | + | ++ | − | − |
| FF | − | − | − | − |
| EX | + | ++ | ++ | ++ |
| EY | − | − | + | ++ |
| EZ | + | ++ | + | ++ |
| FA | − | − | − | − |
| FB | + | ++ | + | ++ |
| AL | + | ++ | + | ++ |
| AG | + | ++ | + | + |
| AI | + | ++ | + | ++ |
| AD | + | ++ | + | ++ |
| AJ | − | − | − | − |
| AC | + | ++ | + | ++ |
| AP | − | − | ++ | ++ |
| AQ | ++ | ++ | ++ | ++ |
| AS | + | ++ | ++ | + |
| AT | − | − | − | − |
| BE | + | ++ | + | ++ |
| BF | ++ | ++ | − | − |
| AK | N/A | N/A | + | ++ |
| AM | N/A | N/A | − | − |
| AN | N/A | N/A | + | ++ |

Example 19

Sprague Dawley rats were dosed intravenously using a normal saline formulation containing 2 mg/kg of the compounds identified in the below table (except for the compounds marked with an asterisk ("*") that were delivered in 5% NMP, 5% Solutol® HS and 90% normal saline formulation). The table below summarizes the results of the IV pharmacokinetics.

| Compound | $C_0$ (ng/mL) | $AUC_{last}$ (hr*ng/mL) | $T_{1/2}$ (hr) | Cl (mL/min/kg) | $V_{ss}$ (L/kg) |
|---|---|---|---|---|---|
| AB | 2050.63 | 2646.67 | 3.42 | 16.1 | 1.13 |
| AA | 607.62 | 397.46 | 0.59 | 84.91 | 2.23 |
| AL | 3993.27 | 6223.5 | 3.73 | 5.4 | 0.83 |
| AG | 2647.4 | 649.6 | 0.4 | 51.36 | 0.7 |
| AI* | 4325.4 | 1259.3 | 1.37 | 26.19 | 0.75 |
| AD* | 2056.1 | 1359.7 | 0.79 | 24.57 | 0.97 |
| AP | 6420.4 | 2941 | 2.77 | 11.21 | 0.92 |
| AQ | 3986 | 2287 | 3.84 | 14.64 | 1.22 |
| BC | 658 | 233 | 0.22 | 145.13 | 2.67 |
| AT | 2755 | 2090 | 2.38 | 15.94 | 1.14 |
| BF | 2225 | 973 | 1.51 | 34.13 | 1.52 |
| EN | 9443 | 1756 | 7.33 | 19.38 | 1.16 |
| AN | 3096.31 | 1466.64 | 0.32 | 22.44 | 0.59 |
| EX | 1338.03 | 658.87 | 1.18 | 50.52 | 2.71 |
| EY | 2096.85 | 1209.29 | 0.56 | 27.44 | 1.09 |
| FB | 981.37 | 782.27 | 0.75 | 41.98 | 2.33 |

In another experiment, Sprague Dawley rats were dosed per os using a normal saline formulation containing 10 mg/kg of the compounds identified in the table below (except for the compounds marked with an asterisk ("*") that were delivered in 5% NMP, 5% Solutol® HS and 90% normal saline formulation). Plasma, brain, and CSF samples were analyzed at various time points over a 24 hour period. The table below summarizes the results of the oral pharmacokinetics.

| Compound | $T_{max}$ (hr) | $C_{max}$ (ng/mL) | $AUC_{last}$ (hr*ng/mL) | CSF $C_{max}$ (ng/mL) | Brain $C_{max}$ (ng/mL) | % F |
|---|---|---|---|---|---|---|
| AB | 0.42 | 7685.76 | 11615.52 | N/A | N/A | 88 |
| AA | 0.33 | 1232.54 | 1543.78 | N/A | N/A | 78 |
| AL | 1 | 9481 | 19303 | 7532 | 3672 | 97 |
| AG | 0.25 | 1928.16 | 1326.62 | 217.3 | 307.49 | 41 |
| AI* | 0.5 | 3967.6 | 5898.2 | 269.17 | 1087.9 | 94 |
| AD* | 0.42 | 2027.3 | 4581.3 | 1009.2 | 1832.2 | 67 |
| AO | 1 | 7310.4 | N/A | 1676.3 | N/A | N/A |
| AP | 2 | 624.6 | 2054.6 | 80.46 | 0 | 15 |
| AQ | 1 | 499.27 | 1805.63 | 65.84 | 29.91 | 16 |
| BC | 0.25 | 868.8 | 611.9 | 1362 | 2321 | 52 |
| AT | 0.25 | 6519 | 8337 | 1758 | 120 | 80 |
| BF | 0.5 | 3025 | 5293 | 56.6 | 61.2 | 100 |
| EN | 0.25 | 1486 | 2207 | 22 | 61 | 25 |
| AN | 0.25 | 4327.98 | 4845.33 | 1384.82 | 1501.76 | 66 |
| EX | 2 | 3188.21 | 7382.3 | 459.46 | 2799.98 | 100 |
| EY | 0.5 | 1129.52 | 2921.86 | 539.09 | 1833.34 | 48 |
| FB | 0.5 | 1588.83 | 3405.16 | 981.8 | 3632.82 | 87 |

Example 20

The Bennett model of mechanical analgesia is used to assess the analgesic effects of compounds as measured by paw withdrawal threshold. Bennett GJ, Xie YK, "A peripheral mononeuropathy in rat that produces disorders of pain sensation like those seen in man," Pain 33:87-107, 1988. Sciatic nerve chronic constriction nerve injury surgery is performed on animals with testing for analgesic response once animals have recovered from surgery but still exhibit a low threshold of paw withdrawal after application of von Frey filaments. Vehicle animals receive the surgery and then receive vehicle rather than test compound. Animals were tested 1 hr, 24 h and 1 wk post-test compound or vehicle administration.

Male 2-3 month old Sprague Dawley rats were used. Harlan was the supplier for all studies. Rats were housed in Lucite cages with aspen wood chip bedding, maintained on a 12:12 light:dark cycle (lights on at 5 AM), and given ad libitum access to Purina lab chow (USA) and tap water throughout the study.

Rats were anesthetized using inhaled isoflurane (2.5%). Sciatic nerve chronic constriction nerve injury surgery was performed as previously described (Bennett and Xie, 1988). An incision (~1.5 cm in length) was made with a scalpel blade dorsally through skin on the right hind limb, parallel and posterior to femur. Using a small pointed hemostat, the biceps femoris and gluteus superficialis muscles were separated. Using curved blunt forceps, the common sciatic nerve was isolated and exposed. For the mechanical analgesia studies, the whole sciatic nerve was ligated. Using hemostats/forceps and chromic gut (5-0), the nerve was loosely ligated with a square knot; 3 ligatures, 1 mm apart were placed on the nerve. The ligatures were tightened to the point that the suture did not slide up or down the nerve. This protocol resulted in a partial loss-of-function of the nerve. Testing occurred approximately 2 weeks post-surgery.

During testing, rats were acclimated to the surface of a suspended wire mesh grid (1 cm×1 cm, with the wire being 0.3 cm in diameter) for 15-20 min. Starting from the smallest, each Von Frey filament was pressed perpendicularly to the plantar surface of the affected (ipsilateral) hind paw until slightly bent and then held for 6 second. If an obvious hind paw withdrawal or a flinching behavior immediately after the withdrawal of the filament was not observed, the next larger filament was used in the same manner. In case of a response, a lower filament was used. This was repeated until six responses were collected.

For all studies, animals were baselined prior to study start to test for allodynia (defined as a paw withdrawal threshold under 5). A subset of animals was tested with gabapentin (150 mg/kg, PO) to ensure at least 50% analgesia. Once it was confirmed animals were ready for study initiation, animals were balanced across groups. All study investigators were blind to treatment conditions. Animals were dosed with 0.1, 1 or 10 mg/kg of test compound via oral gavage (PO), control sets of animals were dosed with gabapentin (150 mg/kg, PO) or vehicle (0.5% Na-CMC in 0.9% sterile saline, PO). Testing occurred 1 h post-dosing with animals retested 24 hrs and 1 week post-dosing. The percent analgesia calculations for each animal were made using the following equation: % analgesia=$[(\log(x)-y)/((\log(z)-y)]*100$, where x=the paw withdrawal threshold for the drug-treated animal in grams, y=the average of the log(x) values for the vehicle treated group, and z=the paw withdrawal threshold for naïve animals in grams (historical value of 15 used).

The results are shown in the table below where the percentage of analgesia is measured at 1 hour, 24 hours, and 1 week after compound administration. Since each study had its own gabapentin control group, an example gabapentin control value is shown. For all studies, gabapentin was confirmed effective (demonstrating at least 50% analgesia at 1 h post-administration). Gabapentin was not different from vehicle and resulted in no analgesia (<5%) at 24 h and 1 week post-administration.

| | 150 mg/kg | | |
|---|---|---|---|
| Compound | 1 h | 24 h | 1 wk |
| Gabapentin | 72% | 16% | 0% |

| | 0.1 mg/kg | | | 1 mg/kg | | | 10 mg/kg | | |
|---|---|---|---|---|---|---|---|---|---|
| Compound | 1 h | 24 h | 1 wk | 1 h | 24 h | 1 wk | 1 h | 24 h | 1 wk |
| AL | 20.9% | 10.8% | 3.1% | 52.7% | 14.4% | 6.6% | 61.9% | 13.8% | 1.1% |
| AG | 26.7% | 14.8% | 1.7% | 41.5% | 23.7% | 0% | 56.9% | 26.7% | 0% |
| AI | 5.3% | 7.7% | 7.7% | 40.4% | 23.4% | 10.2% | 50.0% | 33.2% | 22.0% |
| AD | 18.4% | 4.7% | 0% | 15.4% | 13.8% | 17.9% | 15.3% | 7.6% | 15.5% |
| AO | N/A | N/A | N/A | N/A | N/A | N/A | 23.7% | 7.5% | 18.2% |
| AP | N/A | N/A | N/A | N/A | N/A | N/A | 28.0% | 0% | 0% |

Example 21

A non-clinical in vivo pharmacology study (Porsolt assay) was performed to measure antidepressant-like effects. A negative control (0.5% sodium carboxymethyl cellulose in 0.9% sterile saline vehicle) and a positive control (fluoxetine) are shown for comparison against test compound. The study allowed for the evaluation of the effects of each compound on the Porsolt forced swim test as assessed by the rats' response (reduced floating time) during a 5-minute swimming test.

Male 2-3 month old Sprague Dawley rats were used (Harlan, Indianapolis, Ind.). Rats were housed in Lucite cages with aspen wood chip bedding, maintained on a 12:12 light:dark cycle (lights on at 5 AM), and given ad libitum access to Purina lab chow (USA) and tap water throughout the study.

The Porsolt forced swim test adapted for use in rats was performed as described by Burgdorf et al., (The long-lasting antidepressant effects of rapastinel (GLYX-13) are associated with a metaplasticity process in the medial prefrontal cortex and hippocampus. Neuroscience 308:202-211, 2015). Animals were placed in a 46 cm tall×20 cm in diameter clear glass tube filled to 30 cm with tap water (23±1° C.) for 15 min on the first day (habituation) and 5 min on the subsequent test day. Positive control fluoxetine was dosed 3 times (24 h, 5 h and 1 h) prior to testing. Animals were tested 1 h or 24 h post-dosing with the test compounds or vehicle. Animals received a 15 min habituation session 1 day before the 5 min test. A subset of compounds tested at 1 h post-dosing were retested at 1 wk post-dosing in the same sets of animals. Water was changed after every other animal. Animals were videotaped, and floating time as defined as the minimal amount of effort required to keep the animals head above water was scored offline by a blinded experimenter with high inter-rater reliability (Pearson's r>0.9).

The results for test compounds are shown in the table below. Each compound tested at dose level shown. Significance vs. vehicle group for each experiment is marked. A compound marked "Yes" was found to be statistically significant ($p \leq 0.05$) from vehicle at dose level shown. A compound marked "No" was not statistically significant from vehicle. Data was averaged for test compound and vehicle groups (N approximately 8 per group) and the percent reduction in floating for group treated with test compound relative to group treated with vehicle is shown.

| | 1 h post-dose | | | 24 h post-dose | | | 1 wk post-dose | | |
|---|---|---|---|---|---|---|---|---|---|
| Compound | Dose (mg/kg) | Significance vs. vehicle | % reduction in float time | Dose (0.1 mg/kg) | Significance vs. vehicle | % reduction in float time | Dose (0.1 mg/kg) | Significance vs. vehicle | % reduction in float time |
| Fluoxetine | 20 | Yes | 54% | N/A | N/A | N/A | N/A | N/A | N/A |
| AB | 0.1 | Yes | 73.2% | 0.1 | Yes | 79.90% | NR | NR | NR |
| AA | 0.1 | Yes | 42.0% | 0.1 | Yes | 48.60% | NR | NR | NR |
| AS | 0.1 | Yes | 82.3% | NR | NR | NR | 0.1 | No | 32.0% |
| AT | 0.1 | Yes | 63.4% | NR | NR | NR | 0.1 | Yes | 55.6% |
| BF | 0.1 | Yes | 84.4% | NR | NR | NR | NR | NR | NR |

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is claimed is:

1. A compound having the formula:

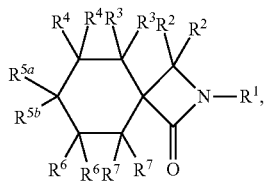

or a pharmaceutically acceptable salt and/or a stereoisomer thereof, wherein:

R$^1$ is selected from the group consisting of: H; —C$_1$-C$_4$alkyl; —C$_1$-C$_4$alkyl-phenyl, wherein phenyl is substituted by one, two or three substituents each independently selected from —C$_1$-C$_4$alkyl, —C$_1$-C$_4$alkoxy, hydroxyl, and halogen; —C(O)—R$^{31}$; —C(O)—O—R$^{32}$; —O—C$_1$-C$_4$alkyl-phenyl, wherein phenyl is optionally substituted by one, two or three substituents each independently selected from —C$_1$-C$_4$alkyl, —C$_1$-C$_4$alkoxy, hydroxyl, and halogen; phenyl, wherein phenyl is optionally substituted by one, two or three substituents each independently selected from —C$_1$-C$_4$alkyl, —C$_1$-C$_4$alkoxy, hydroxyl, and halogen; and —CH(R$^8$)—C(O)—R$^9$;

R$^2$ is independently selected for each occurrence from the group consisting of H, —C$_1$-C$_4$alkyl, and —C$_1$-C$_4$haloalkyl;

R$^3$, R$^4$, R$^6$, and R$^7$ are each independently selected for each occurrence from the group consisting of H, hydroxyl, halogen, cyano, —C$_1$-C$_4$alkyl, and —C$_1$-C$_4$haloalkyl; or R$^3$ and R$^4$ taken together with the adjacent carbons to which they are attached form a 3-membered carbocyclic ring which is optionally substituted by one or two substituents independently selected from the group consisting of halogen, hydroxyl, —C$_1$-C$_3$alkyl, —C$_1$-C$_3$alkoxy, —C(O)NR$^a$R$^b$, and —NR$^a$R$^b$;

R$^{5a}$ is selected from the group consisting of hydroxyl, halogen, cyano, —O—C$_1$-C$_4$ alkyl-phenyl, —C(O)—C$_1$-C$_4$alkyl, —NR$^a$—C(O)—C$_1$-C$_4$alkyl, —NR$^a$—C(O)—O—C$_1$-C$_4$alkyl, —NR$^a$R$^b$, and —NR$^a$CH(R$^{10}$)—C(O)—R$^{11}$; wherein C$_1$-C$_4$alkyl is optionally substituted by one, two or three substituents each independently selected from —COOH, —C(O)NH$_2$, —NR$^a$R$^b$, —SH, —C(O)—C$_1$-C$_4$alkyl, —C(O)—O—C$_1$-C$_4$alkyl, —O—C(O)—C$_1$-C$_4$alkyl, —C$_1$-C$_4$alkoxy, phenyl, hydroxyl, and halogen; and phenyl, independently for each occurrence is optionally substituted by one, two or three substituents each independently selected from —C$_1$-C$_4$alkyl, —C$_1$-C$_4$haloalkyl, —C$_1$-C$_4$alkoxy, —NR$^a$R$^b$, hydroxyl, cyano, and halogen;

R$^{5b}$ is selected from the group consisting of H, halogen, cyano, —C$_1$-C$_4$alkyl, and —C$_1$-C$_4$haloalkyl; or R$^{5a}$ and R$^{5b}$ taken together form an oxo group;

R$^8$ and R$^{10}$ are independently selected from the group consisting of H and —C$_1$-C$_4$alkyl, wherein C$_1$-C$_4$alkyl is optionally substituted by one, two or three substituents each independently selected from —C(O)NR$^a$R$^b$, —NR$^a$—C(O)—C$_1$-C$_4$alkyl, NR$^a$R$^b$, —SH, —C(O)—C$_1$-C$_4$alkyl, —C(O)—O—C$_1$-C$_4$alkyl, —O—C(O)—C$_1$-C$_4$alkyl, —COOH, hydroxyl, and halogen;

R$^9$ and R$^{11}$ are independently selected from the group consisting of hydroxyl, —C$_1$-C$_4$alkoxy, and —NR$^a$R$^b$;

R$^{31}$ is selected from the group consisting of hydrogen, —C$_1$-C$_6$alkyl, —C$_1$-C$_6$haloalkyl, —C$_3$-C$_6$cycloalkyl, and phenyl;

R$^{32}$ is selected from the group consisting of hydrogen, —C$_1$-C$_6$alkyl, —C$_1$-C$_6$haloalkyl, —C$_3$-C$_6$cycloalkyl, benzyl, and phenyl; and R$^a$ and R$^b$ are each independently selected for each occurrence from the group consisting of H, —C$_1$-C$_4$alkyl, —C$_1$-C$_4$alkyl-phenyl, —C$_1$-C$_4$alkyl-C$_3$-C$_7$cycloalkyl, —C$_1$-C$_4$alkyl-heterocycloalkyl, and —C$_1$-C$_4$alkyl-heteroaryl, wherein heterocycloalkyl and heteroaryl include 1, 2, or 3 ring atoms independently selected from N, O and S, and phenyl is optionally substituted by one, two or three substituents selected from halogen, hydroxyl, —C(O)NH$_2$, —C(O)NH(C$_1$-C$_4$alkyl), —C(O)N(C$_1$-C$_4$alkyl)$_2$, —C$_1$-C$_3$alkyl and —C$_1$-C$_3$alkoxy; or R$^a$ and R$^b$ taken together with the nitrogen to which they are attached form a 4-6-membered heterocycloalkyl or a 5-8-membered heteroaryl.

2. The compound of claim 1, wherein each occurrence of R$^3$, R$^4$, R$^6$, and R$^7$ is H.

3. The compound of claim 1, wherein each occurrence of R$^2$ is H.

4. The compound of claim 1, wherein R$^1$ is selected from the group consisting of:

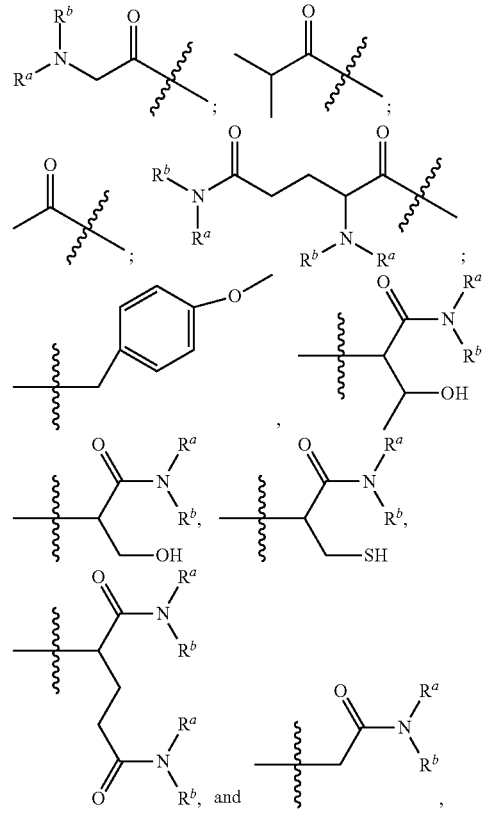

wherein R$^a$ and R$^b$ are each independently selected for each occurrence from the group consisting of hydrogen and —C$_1$-C$_4$alkyl.

5. The compound of claim 1, wherein R$^{5b}$ is selected from H and F.

6. The compound of claim 1, wherein R$^{5a}$ is selected from the group consisting of hydroxyl, halogen, —O—CH$_2$-Ph, —NH$_2$, —NH—C$_1$-C$_4$alkyl, —NH—C(O)—C$_1$-C$_4$alkyl, —NH—C(O)—O—C$_1$-C$_4$alkyl, and —NR$^a$CH(R$^{10}$)—C(O)—R$^{11}$, wherein C$_1$-C$_4$alkyl is optionally substituted by one or two substituents each independently selected from —C(O)NH$_2$, —NH$_2$, —SH, —OC(O)CH$_3$, hydroxyl, and halogen;

R$^{10}$ is selected from the group consisting of H and C$_1$-C$_4$alkyl, wherein C$_1$-C$_4$alkyl is optionally substituted by one or two substituents each independently selected from —C(O)NR$^a$R$^b$, —NR$^a$—C(O)—C$_1$-C$_4$alkyl, —NR$^a$R$^b$, —SH, —C(O)—C$_1$-C$_4$alkyl, —C(O)—O—C$_1$-C$_4$alkyl, —O—C(O)—C$_1$-C$_4$alkyl, —C$_1$-C$_4$alkoxy, —COOH, hydroxyl, and halogen; and R$^{11}$ is selected from the group consisting of hydroxyl, —C$_1$-C$_4$alkoxy, and —NR$^a$R$^b$.

7. The compound of claim 1, wherein R$^{5b}$ is H; and
R$^{5a}$ is selected from the group consisting of hydroxyl, halogen, —O—CH$_2$-Ph, —NH$_2$,

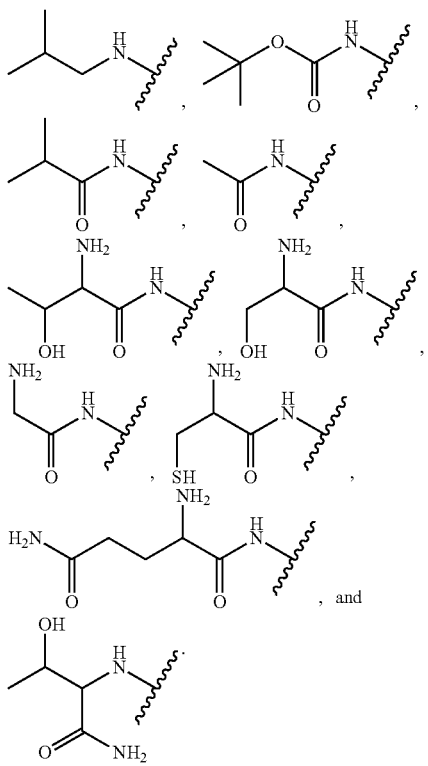

, and

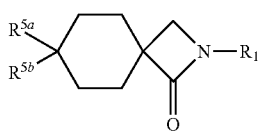

.

8. A compound having the formula:

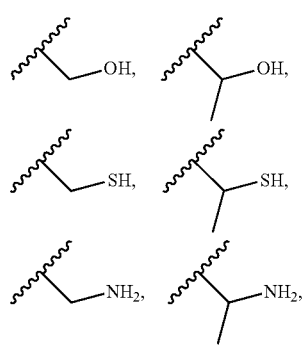

or a pharmaceutically acceptable salt and/or a stereoisomer thereof, wherein:

R$^1$ is selected from the group consisting of H, —C$_1$-C$_4$alkyl, —C$_1$-C$_4$alkyl-phenyl, and —CH(R$^8$)—C(O)—R$^9$; wherein phenyl is substituted by one, two or three substituents each independently selected from —C$_1$-C$_4$alkyl, C$_1$-C$_4$alkoxy, hydroxyl, and halogen; and R$^{5a}$ is selected from the group consisting of hydroxyl, halogen, cyano, —O—C$_1$-C$_4$ alkyl-phenyl, —C(O)—C$_1$-C$_4$alkyl, —NR$^a$—C(O)—C$_1$-C$_4$alkyl, —NR$^a$—C(O)—O—C$_1$-C$_4$alkyl, —NR$^a$R$^b$, and —NR$^a$CH(R$^{10}$)—C(O)—R$^{11}$; wherein C$_1$-C$_4$alkyl is optionally substituted by one, two or three substituents each independently selected from —COOH, —C(O)NH$_2$, —NR$^a$R$^b$, —SH, —C(O)—C$_1$-C$_4$alkyl, —C(O)—O—C$_1$-C$_4$alkyl, —O—C(O)—C$_1$-C$_4$alkyl, —C$_1$-C$_4$alkoxy, hydroxyl, and halogen; and phenyl is optionally substituted by one, two or three substituents each independently selected from —C$_1$-C$_4$alkyl, —C$_1$-C$_4$haloalkyl, —C$_1$-C$_4$alkoxy, —NR$^a$R$^b$, hydroxyl, and halogen;

R$^{5b}$ is selected from the group consisting of H, halogen, —C$_1$-C$_4$alkyl, and —C$_1$-C$_4$haloalkyl; or R$^{5a}$ and R$^{5b}$ taken together form an oxo group;

R$^8$ and R$^{10}$ are selected independently from the group consisting of H and —C$_1$-C$_4$alkyl, wherein C$_1$-C$_4$alkyl is optionally substituted by one, two or three substituents each independently selected from —C(O)NR$^a$R$^b$, —NR$^a$—C(O)—C$_1$-C$_4$alkyl, —NR$^a$R$^b$, —SH, —C(O)—C$_1$-C$_4$alkoxy, —COOH, hydroxyl, and halogen;

R$^9$ and R$^{11}$ are selected independently from the group consisting of hydroxyl, C$_1$-C$_4$alkoxy, and —NR$^a$R$^b$; and R$^a$ and R$^b$ are each independently selected for each occurrence from the group consisting of H, —C$_1$-C$_4$alkyl-C$_3$-C$_7$cycloalkyl, —C$_1$-C$_4$alkyl-heterocycloalkyl, and —C$_1$-C$_4$alkyl-heteroaryl, wherein heterocycloalkyl and heteroaryl include 1, 2, or 3 ring atoms independently selected from N, O and S, and phenyl is optionally substituted by one, two or three substituents selected from halogen, hydroxyl, —C(O)NH2, —C(O)NH(C$_1$-C$_4$alkyl), —C(O)N(C$_1$-C$_4$alkyl)$_2$, —C$_1$-C$_3$alkyl and —C$_1$-C$_3$alkoxy; or R$^a$ and R$^b$ taken together with the nitrogen to which they are attached form a 4-6-membered heterocycloalkyl or a 5-8-membered heteroaryl.

9. The compound of claim 8, wherein R$^1$ is H or —CH(R$^8$)—C(O)—R$^9$;

R$^8$ is selected from the group consisting of H and C$_1$-C$_4$alkyl, wherein —C$_1$-C$_4$alkyl is optionally substituted by one or two substituents each independently selected from —C(O)NH$_2$, —NH$_2$, —SH, —O—C(O)—C$_1$-C$_4$alkyl, —C$_1$-C$_4$alkoxy, —COOH, and hydroxyl; and R$^9$ is selected independently from the group consisting of hydroxyl, —C$_1$-C$_4$alkoxy, and —NR$^a$R$^b$.

10. The compound of claim 9, wherein R$^8$ is selected from the group consisting of H, methyl, -continued

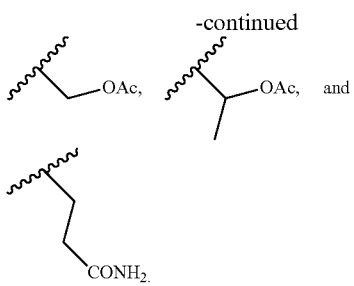

11. The compound of claim 8, wherein $R^{5a}$ is selected from the group consisting of hydroxyl, halogen, —O—CH$_2$-Ph, —NH$_2$, —NH—C$_1$-C$_4$alkyl, —NH—C(O)—C$_1$-C$_4$alkyl, —NH—C(O)—O—C$_1$-C$_4$alkyl, and —NR$^a$CH(R$^{10}$)—C(O)—R$^{11}$; wherein C$_1$-C$_4$alkyl is optionally substituted by one or two substituents each independently selected from —C(O)NH$_2$, —NH$_2$, —SH, —OC(O)CH$_3$, hydroxyl, and halogen; and
   $R^{5b}$ is H or halogen.

12. A compound having the formula:

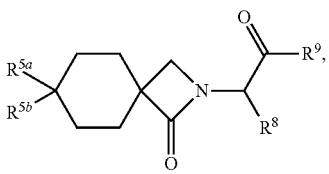

or a pharmaceutically acceptable salt and/or a stereoisomer thereof, wherein:
   $R^{5a}$ is selected from the group consisting of H, hydroxyl, halogen, —CH$_3$, —C(O)—C$_1$-C$_4$alkyl, —O—CH$_2$-Ph, —NH$_2$, —NH—C$_1$-C$_4$alkyl, —NH—C(O)—C$_1$-C$_4$alkyl, —NH—C(O)—O—C$_1$-C$_4$alkyl, and —NR$^a$CH(R$^{10}$)—C(O)—R$^{11}$; wherein C$_1$-C$_4$alkyl is optionally substituted by one or two substituents each independently selected from —C(O)NH$_2$, —NH$_2$, —SH, —OC(O)CH$_3$, hydroxyl, and halogen;
   $R^{5b}$ is H or halogen;
   $R^8$ and $R^{10}$ are selected independently from the group consisting of H and C$_1$-C$_4$alkyl, wherein the C$_1$-C$_4$alkyl may be optionally substituted by one, two or three substituents each independently selected from —C(O)NR$^a$R$^b$, —NR$^a$—C(O)—C$_1$-C$_4$alkyl, —NR$^a$R$^b$, —SH, —C(O)—C$_1$-C$_4$alkyl, —C(O)—O—C$_1$-C$_4$alkyl, —O—C(O)—C$_1$-C$_4$alkyl, C$_1$-C$_4$alkoxy, —COOH, hydroxyl, and halogen; and
   $R^9$ and $R^{11}$ are selected independently from the group consisting of hydroxyl, C$_1$-C$_4$alkoxy, and —NR$^a$R$^b$; and
   $R^a$ and $R^b$ are each independently selected for each occurrence from the group consisting of H, —C$_1$-C$_4$alkyl, C$_1$-C$_4$alkyl-phenyl, —C$_1$-C$_4$alkyl-C$_3$-C$_7$cycloalkyl, —C$_1$-C$_4$alkyl-heterocycloalkyl, and —C$_1$-C$_4$alkyl-heteroaryl, wherein heterocycloalkyl and heteroaryl include 1, 2, or 3 ring atoms independently selected from N, O and S, and phenyl is optionally substituted by one, two or three substituents selected from halogen, hydroxyl, —C(O)NH2, —C(O)NH(C$_1$-C$_4$alkyl), —C(O)N(C$_1$-C$_4$alkyl)$_2$, —C$_1$-C$_3$alkyl and —C$_1$-C$_3$alkoxy; or
   $R^a$ and $R^b$ taken together with the nitrogen to which they are attached form a 4-6-membered heterocycloalkyl or a 5-8-membered heteroaryl.

13. The compound of claim 12, wherein $R^{5a}$ is selected from the group consisting of H, hydroxyl, halogen, methyl, —O—CH$_2$-Ph, —NH$_2$, —NH—C$_1$-C$_4$alkyl, —NH—C(O)—C$_1$-C$_4$alkyl, and —NH—C(O)—O—C$_1$-C$_4$alkyl, wherein C$_1$-C$_4$alkyl is optionally substituted by one or two substituents each independently selected from —C(O)NH$_2$, —NH$_2$, —SH, —OC(O)CH$_3$, hydroxyl, and halogen.

14. The compound of claim 12, wherein $R^{5a}$ is selected from the group consisting of H, hydroxyl, halogen, methyl, —O—CH$_2$-Ph, —NH$_2$,

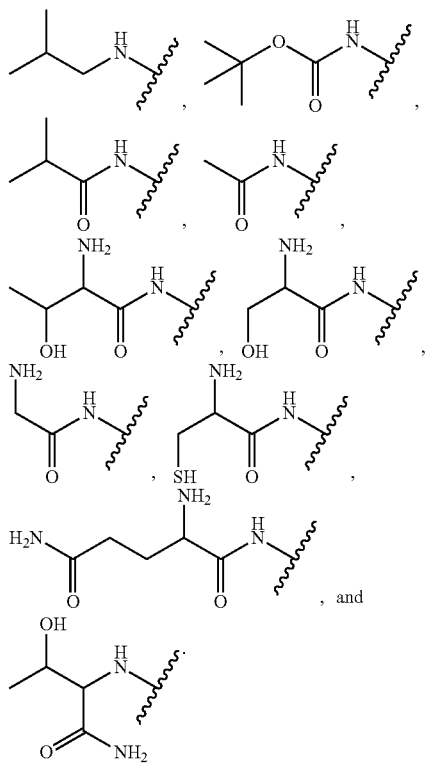

15. The compound of claim 12, wherein $R^{5b}$ is H or halogen; and
   $R^{5a}$ is selected from the group consisting of H, hydroxyl, halogen, methyl, —O—CH$_2$-Ph, —NH$_2$,

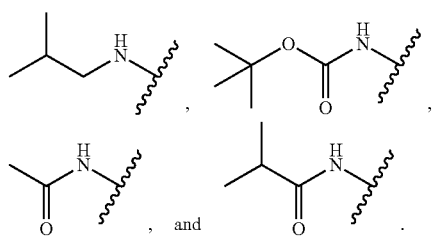

16. The compound of claim 12, wherein $R^8$ is selected from the group consisting of H, methyl,

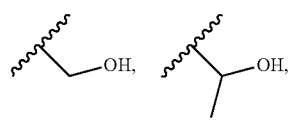

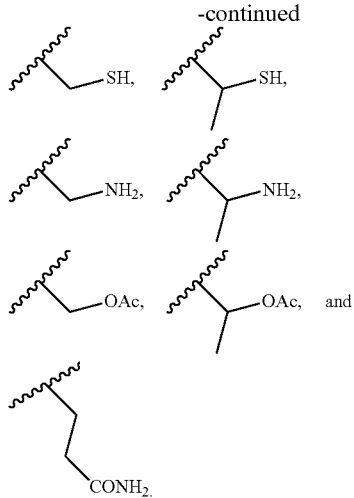

17. The compound of claim 12, wherein R⁹ is —NH₂).

18. A pharmaceutical composition comprising a compound of claim 1; and a pharmaceutically acceptable excipient.

19. A method of treating depression, attention deficit disorder, schizophrenia, anxiety, or a migraine, in a patient in need thereof, the method comprising administering to the patient an effective amount of the compound of claim 1.

20. A method of treating neuropathic pain, in a patient in need thereof, the method comprising administering to the patient an effective amount of the compound of claim 1.

21. A pharmaceutical composition comprising a compound of claim 12; and a pharmaceutically acceptable excipient.

22. A method of treating depression, attention deficit disorder, schizophrenia, anxiety, or a migraine, in a patient in need thereof, the method comprising administering to the patient an effective amount of the compound of claim 12.

23. A method of treating neuropathic pain, in a patient in need thereof, the method comprising administering to the patient an effective amount of the compound of claim 12.

24. The compound of claim 1, wherein the compound is selected from the group consisting of:

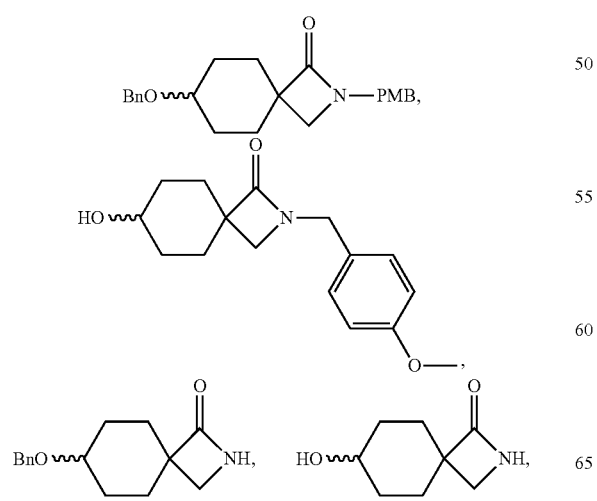

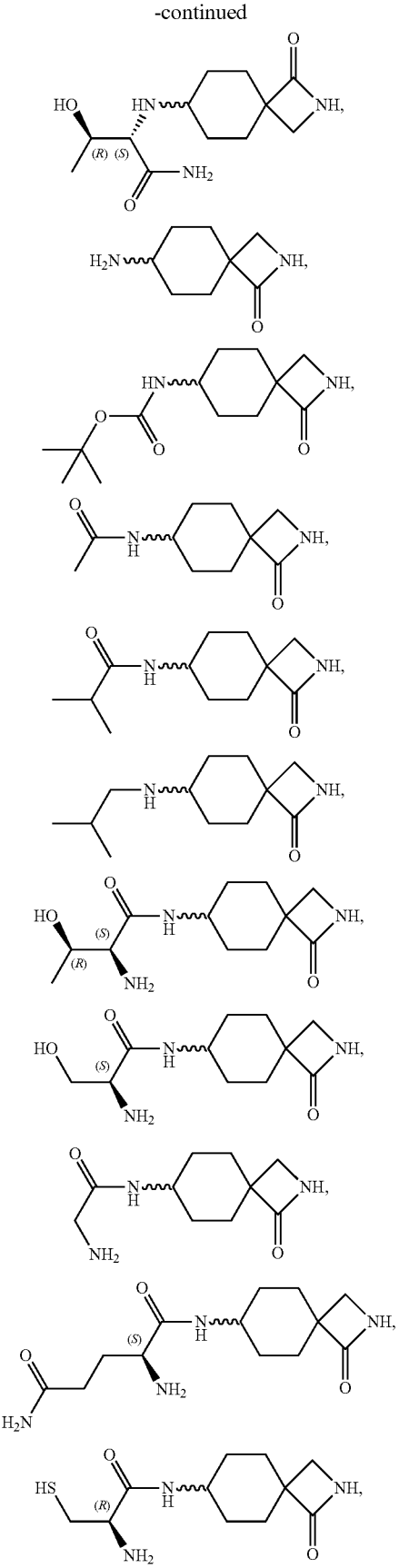

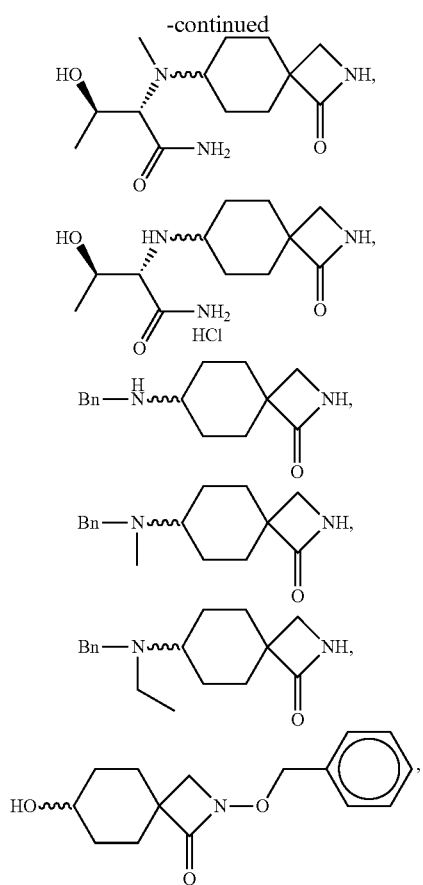
and a pharmaceutically acceptable salt and/or a stereoisomer thereof.
25. The compound of claim 12, wherein the compound is selected from:
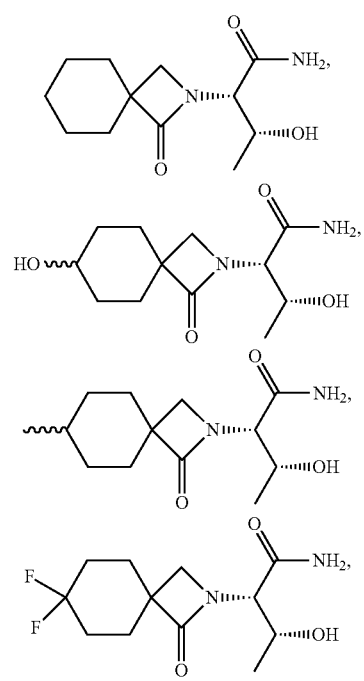
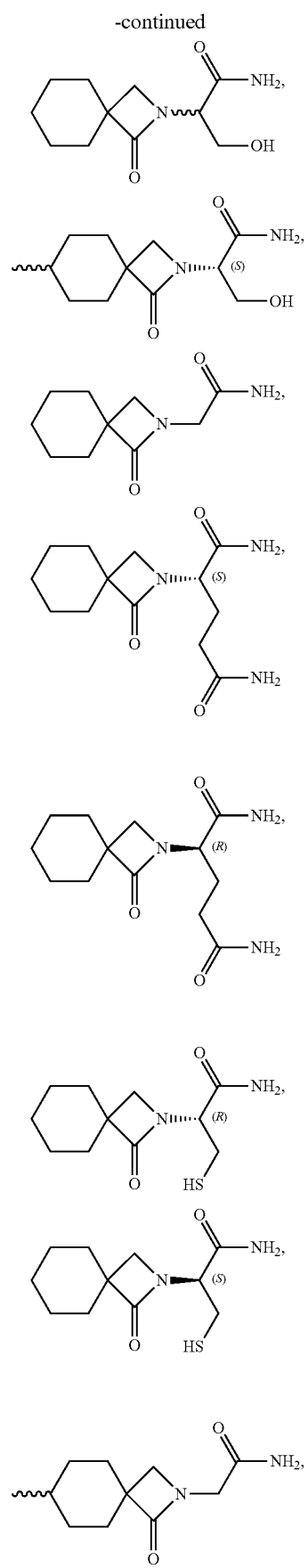

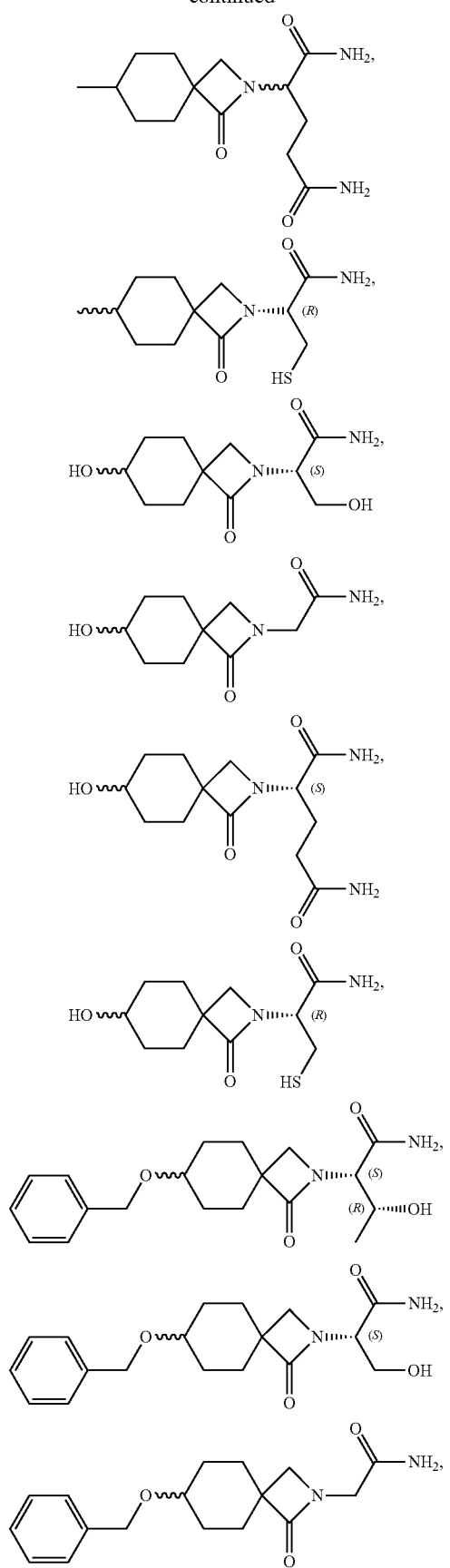
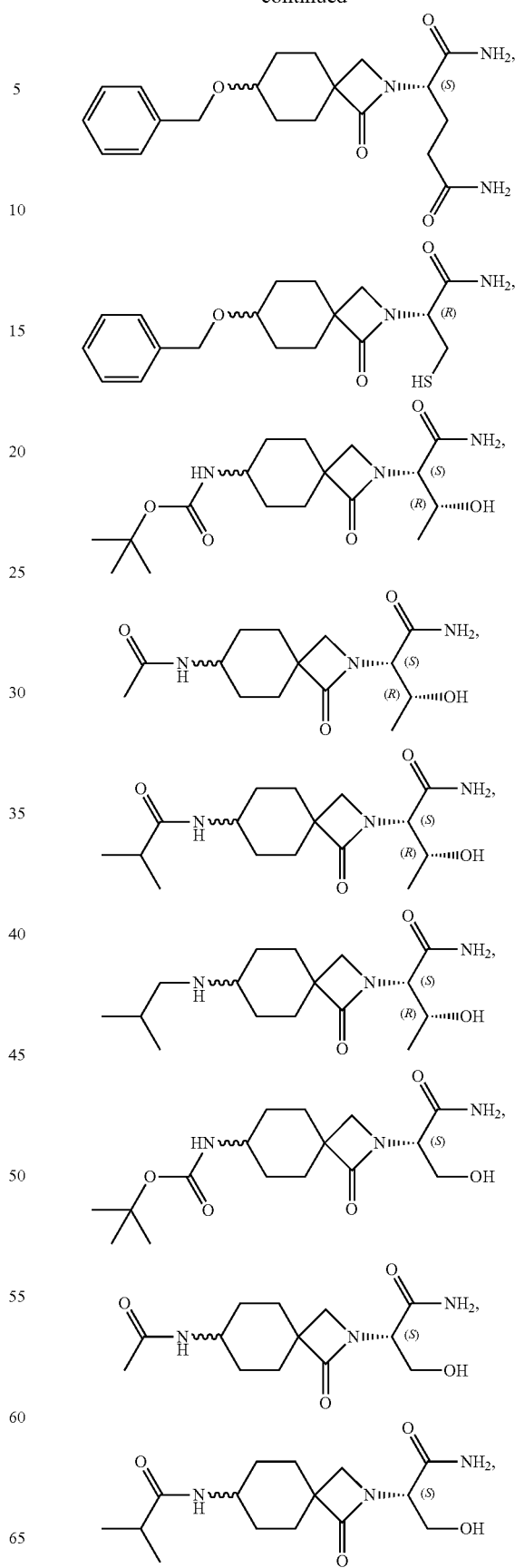

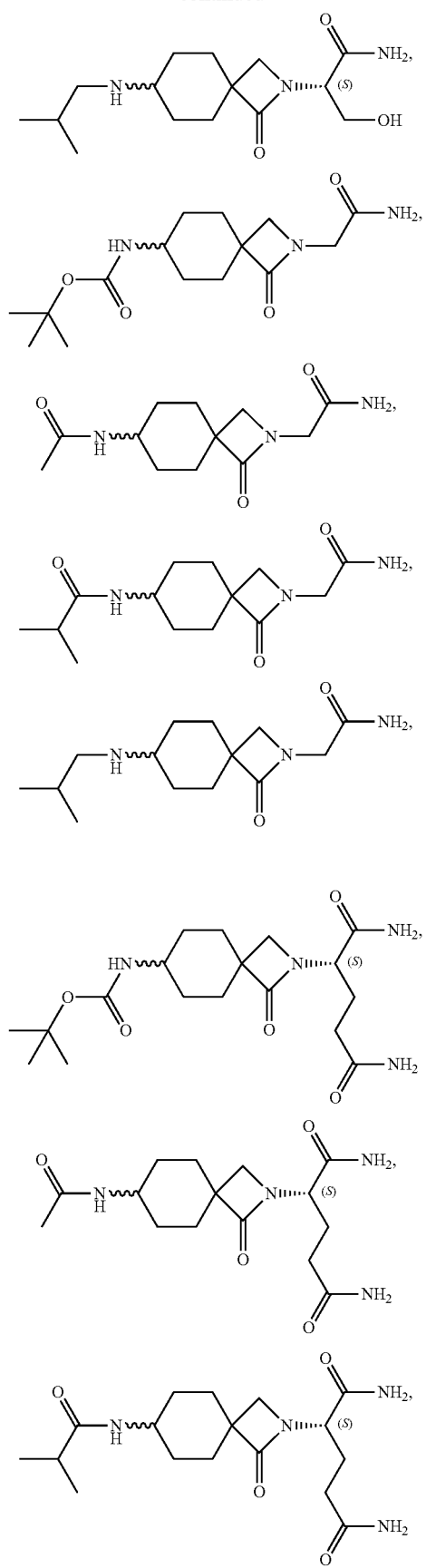
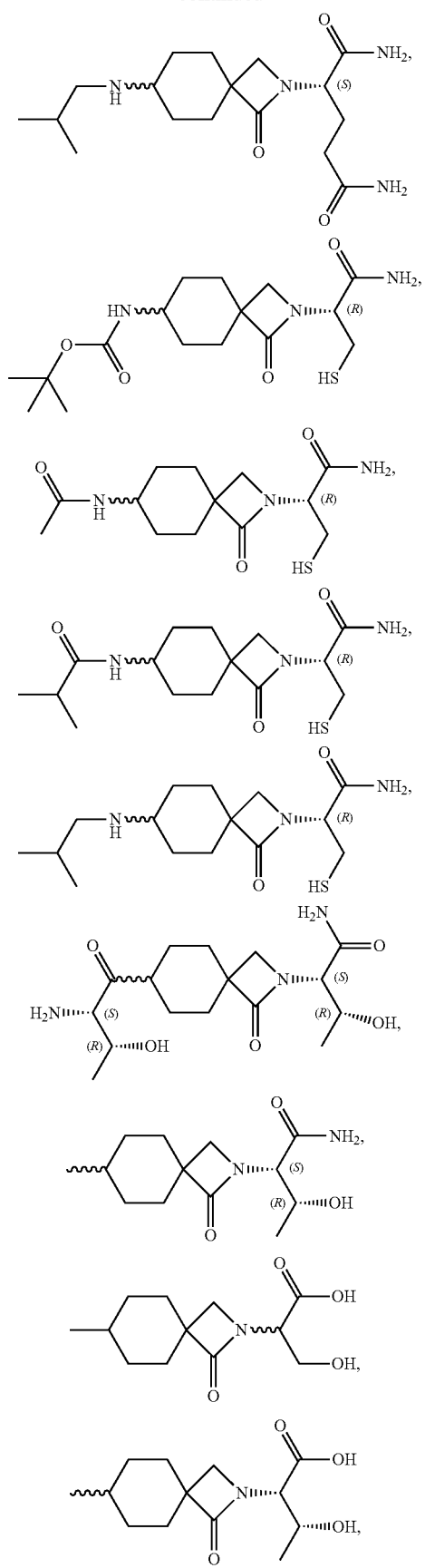

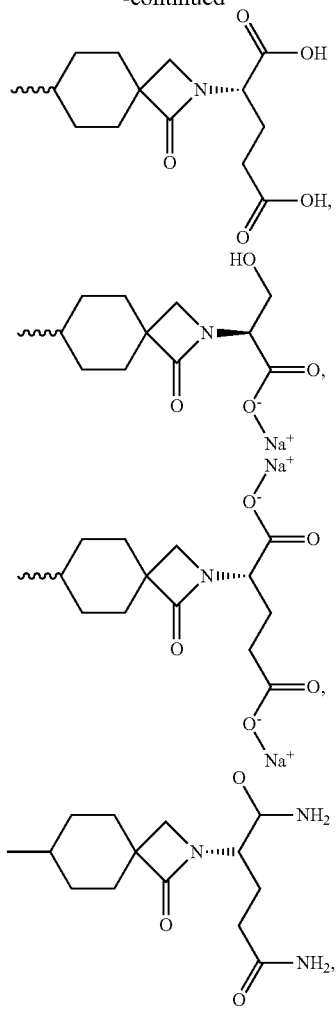
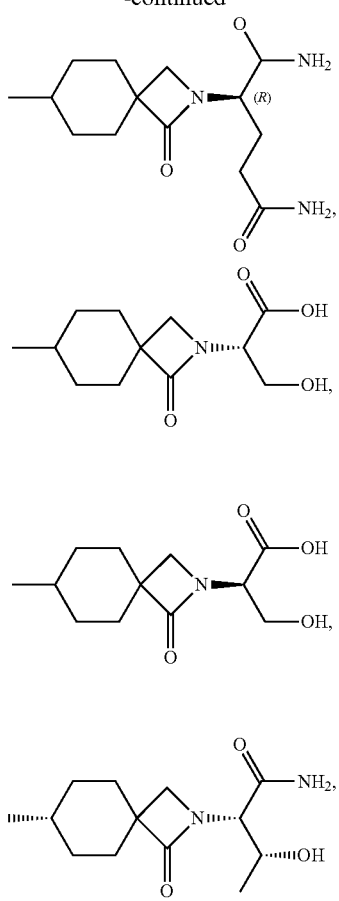
and a pharmaceutically acceptable salt and/or a stereoisomer thereof.
* * * * *